US012805600B2

(12) United States Patent
Perrault et al.

(10) Patent No.: US 12,805,600 B2
(45) **Date of Patent: *Nov. 24, 2026**

(54) FOOTWEAR MIDSOLE WITH WARPED LATTICE STRUCTURE AND METHOD OF MAKING THE SAME

(71) Applicant: adidas AG, Herzogenaurach (DE)

(72) Inventors: Jacques Perrault, Portland, OR (US); Derek Andrew Luther, Portland, OR (US); Berin Skye B, Portland, OR (US); Marco Florian Kormann, Fürth (DE)

(73) Assignee: adidas AG, Herzogenaurach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/901,965

(22) Filed: Sep. 30, 2024

(65) Prior Publication Data

US 2025/0017319 A1 Jan. 16, 2025

Related U.S. Application Data

(60) Continuation of application No. 17/187,304, filed on Feb. 26, 2021, now Pat. No. 12,102,172, which is a (Continued)

(51) Int. Cl.

| | |
|---|---|
| ***B29C 64/393*** | (2017.01) |
| ***A43B 1/00*** | (2006.01) |

(Continued)

(52) U.S. Cl.

CPC .............. *A43B 13/186* (2013.01); *A43B 1/00* (2013.01); *A43B 1/10* (2013.01); *A43B 13/04* (2013.01);

(Continued)

(58) Field of Classification Search

None

See application file for complete search history.

(56) References Cited

U.S. PATENT DOCUMENTS

| | | |
|---|---|---|
| 354,693 A | 12/1886 | Dick |
| D29,749 S | 11/1898 | Bunker |

(Continued)

FOREIGN PATENT DOCUMENTS

| | | |
|---|---|---|
| CN | 101611953 A | 12/2009 |
| CN | 102578760 A | 7/2012 |

(Continued)

OTHER PUBLICATIONS

"Adidas Breaks the Mould With 3D-Printed Performance Footwear," Adidas Group, [Retrieved on Oct. 7, 2015], Retrieved from the Internet: ( http://www.adidas-group.com/en/media/news-archive/press-releases/2015/adi-das-breaks-mould-3d-printed-performance-footwear/ ).

(Continued)

*Primary Examiner* — Yung-Sheng M Tsui
*Assistant Examiner* — Melody Tsui
(74) *Attorney, Agent, or Firm* — Sterne, Kessler, Goldstein & Fox P.L.L.C.

(57) ABSTRACT

A midsole for an article of footwear including a three-dimensional mesh including interconnected unit cells and methods of making the same. The interconnected unit cells each include a plurality of struts defining a three-dimensional shape. The interconnected unit cells are connected at nodes having a valence number defined by the number of struts connected at that node. The valence number of the nodes may vary to provide customized characteristics to zones or portions of the midsole. The plurality of interconnected unit cells may be organized in a warped cubic lattice structure. The warped cubic lattice structure and the size/

(Continued)

shape of interconnected unit cells may vary to provide customized characteristics to zones or portions of the midsole. The three-dimensional mesh may be customized based on a biometric data profile for an individual, or group of individuals. The midsole may be manufactured using an additive manufacturing process.

18 Claims, 39 Drawing Sheets

Related U.S. Application Data division of application No. 15/898,000, filed on Feb. 15, 2018, now Pat. No. 10,932,521, which is a continuation-in-part of application No. 15/470,570, filed on Mar. 27, 2017, now Pat. No. 10,575,588.

(51) Int. Cl.

| | |
|---|---|
| ***A43B 1/10*** | (2006.01) |
| ***A43B 13/04*** | (2006.01) |
| ***A43B 13/14*** | (2006.01) |
| ***A43B 13/18*** | (2006.01) |
| ***A43D 1/02*** | (2006.01) |
| ***A61B 5/00*** | (2006.01) |
| ***A61B 5/11*** | (2006.01) |
| ***B29C 64/124*** | (2017.01) |
| ***B33Y 10/00*** | (2015.01) |
| ***B33Y 50/00*** | (2015.01) |
| ***B33Y 50/02*** | (2015.01) |
| ***B33Y 80/00*** | (2015.01) |
| *A43B 5/00* | (2022.01) |
| *A43B 5/02* | (2006.01) |
| *A43B 5/06* | (2022.01) |
| *A43B 5/10* | (2006.01) |
| *A43B 5/12* | (2006.01) |
| *A43B 5/14* | (2006.01) |
| *A61B 5/0205* | (2006.01) |
| *A61B 5/024* | (2006.01) |
| *A61B 5/103* | (2006.01) |
| *B29L 31/50* | (2006.01) |

(52) U.S. Cl.

CPC .......... *A43B 13/141* (2013.01); *A43B 13/181* (2013.01); *A43B 13/187* (2013.01); *A43D 1/02* (2013.01); *A61B 5/112* (2013.01); *A61B 5/1121* (2013.01); *A61B 5/6807* (2013.01); *B29C 64/124* (2017.08); *B29C 64/393* (2017.08); *B33Y 10/00* (2014.12); *B33Y 50/00* (2014.12); *B33Y 50/02* (2014.12); *B33Y 80/00* (2014.12); *A43B 1/0063* (2013.01); *A43B 5/002* (2013.01); *A43B 5/025* (2013.01); *A43B 5/06* (2013.01); *A43B 5/10* (2013.01); *A43B 5/12* (2013.01); *A43B 5/14* (2013.01); *A43D 1/025* (2013.01); *A43D 2200/60* (2013.01); *A61B 5/02055* (2013.01); *A61B 5/024* (2013.01); *A61B 5/1038* (2013.01); *A61B 2503/10* (2013.01); *A61B 2503/12* (2013.01); *A61B 2562/0219* (2013.01); *A61B 2562/0223* (2013.01); *B29L 2031/504* (2013.01)

(56) References Cited

U.S. PATENT DOCUMENTS

| | | | |
|---|---|---|---|
| 1,111,437 | A | 9/1914 | Butterfield |
| D90,057 | S | 5/1933 | Cleef |
| D107,977 | S | 1/1938 | Tousley |
| D113,620 | S | 3/1939 | Cairns |
| D115,636 | S | 7/1939 | Sperry |
| 2,205,356 | A | 6/1940 | Rose et al. |
| D123,898 | S | 12/1940 | Tousley |
| D138,517 | S | 8/1944 | Meltzer |
| 2,853,809 | A | 9/1958 | Carlo |
| D196,491 | S | 10/1963 | Papoutsy |
| 3,253,601 | A | 5/1966 | Scholl |
| 3,416,174 | A | 12/1968 | Novitske |
| 3,793,750 | A | 2/1974 | Bowerman |
| D241,484 | S | 9/1976 | Castano |
| D241,688 | S | 10/1976 | Johnson |
| 4,012,855 | A | 3/1977 | Gardner |
| D254,818 | S | 4/1980 | Jones |
| D255,175 | S | 6/1980 | Iwakata |
| D255,177 | S | 6/1980 | Fuzita |
| D255,178 | S | 6/1980 | Fuzita |
| D257,075 | S | 9/1980 | Amicone et al. |
| 4,271,606 | A | 6/1981 | Rudy |
| 4,297,796 | A | 11/1981 | Stirtz et al. |
| 4,309,831 | A | 1/1982 | Pritt |
| D265,605 | S | 8/1982 | Batra |
| 4,378,643 | A | 4/1983 | Johnson |
| D272,963 | S | 3/1984 | Muller et al. |
| 4,439,936 | A | 4/1984 | Clarke et al. |
| D273,631 | S | 5/1984 | Ueda |
| D278,851 | S | 5/1985 | Austin |
| D279,620 | S | 7/1985 | Ueda |
| D281,459 | S | 11/1985 | Parker |
| 4,607,440 | A | 8/1986 | Roberts et al. |
| D288,621 | S | 3/1987 | Surpuriya et al. |
| D297,383 | S | 8/1988 | Mourad et al. |
| 4,774,774 | A | 10/1988 | Allen, Jr. |
| D299,681 | S | 2/1989 | Miller et al. |
| D301,184 | S | 5/1989 | Hase |
| D301,800 | S | 6/1989 | Mitsui |
| D302,352 | S | 7/1989 | Austin |
| D303,316 | S | 9/1989 | Crowley |
| D307,817 | S | 5/1990 | Schneider |
| D312,920 | S | 12/1990 | Aveni |
| D316,324 | S | 4/1991 | Rogers |
| D321,973 | S | 12/1991 | Hatfield |
| D326,181 | S | 5/1992 | Katz et al. |
| D333,555 | S | 3/1993 | Hatfield et al. |
| D335,385 | S | 5/1993 | Kawabata |
| D335,572 | S | 5/1993 | Peterson |
| D336,775 | S | 6/1993 | Smith |
| D337,428 | S | 7/1993 | Allen, III et al. |
| 5,236,637 | A | 8/1993 | Hull |
| D339,464 | S | 9/1993 | Teague |
| 5,337,492 | A | 8/1994 | Anderie et al. |
| 5,367,791 | A | 11/1994 | Gross et al. |
| D354,693 | S | 1/1995 | Miller |
| 5,391,072 | A | 2/1995 | Lawton et al. |
| 5,423,135 | A | 6/1995 | Poole et al. |
| D370,993 | S | 6/1996 | Mangee |
| 5,529,473 | A | 6/1996 | Lawton et al. |
| D384,795 | S | 10/1997 | Hudson |
| D384,796 | S | 10/1997 | Smith, III |
| D387,698 | S | 12/1997 | Hatfield et al. |
| D389,993 | S | 2/1998 | Ryan |
| D390,348 | S | 2/1998 | Meyer et al. |
| D390,690 | S | 2/1998 | Murai et al. |
| D391,747 | S | 3/1998 | Avar |
| D393,341 | S | 4/1998 | Marshall et al. |
| D394,342 | S | 5/1998 | Schneider |
| D394,741 | S | 6/1998 | Gaudio |
| D395,340 | S | 6/1998 | Tresser |
| D395,343 | S | 6/1998 | Lozano |
| D395,740 | S | 7/1998 | Cass |
| D395,743 | S | 7/1998 | Ryan |
| D397,546 | S | 9/1998 | Merceron |
| 5,799,417 | A | 9/1998 | Burke et al. |
| D400,345 | S | 11/1998 | Teaque |
| D401,745 | S | 12/1998 | Greenberg |
| D401,747 | S | 12/1998 | Cessor |
| D402,450 | S | 12/1998 | Munns |
| 5,862,614 | A | 1/1999 | Koh |
| D404,897 | S | 2/1999 | Marshall |

(56) References Cited

U.S. PATENT DOCUMENTS

D407,892 S 4/1999 Gaudio
D408,972 S 5/1999 Greenberg
D411,910 S 7/1999 Cessor
D412,050 S 7/1999 Chassaing
D412,239 S 7/1999 Sorofman
5,930,916 A 8/1999 Connor
5,983,529 A 11/1999 Serna
5,985,383 A 11/1999 Allen et al.
6,014,821 A 1/2000 Yaw
D420,208 S 2/2000 Birkenstock
6,021,588 A 2/2000 Alviso
6,076,283 A 6/2000 Boie
D432,762 S 10/2000 Weege
D432,763 S 10/2000 Smith, III
D433,215 S 11/2000 Smith, III
D442,768 S 5/2001 Matis
6,259,962 B1 7/2001 Gothait
6,367,172 B2 4/2002 Hernandez
D458,441 S 6/2002 Gillespie
D459,865 S 7/2002 Urie et al.
D461,040 S 8/2002 Urie et al.
D480,540 S 10/2003 Hoyt et al.
6,665,958 B2 12/2003 Goodwin
D485,662 S 1/2004 Magro
D488,916 S 4/2004 McClaskie
6,763,611 B1 7/2004 Fusco
D497,707 S 11/2004 Lee
D500,399 S 1/2005 Fuerst
D515,791 S 2/2006 McClaskie
D529,697 S 10/2006 Earle
D536,163 S 2/2007 McClaskie
D538,519 S 3/2007 McClaskie
D552,337 S 10/2007 Parekh et al.
D556,988 S 12/2007 Horne et al.
D561,438 S 2/2008 Belley
D561,439 S 2/2008 Schoenborn et al.
D561,443 S 2/2008 Robinson, Jr. et al.
7,383,647 B2 6/2008 Chan et al.
D572,462 S 7/2008 Hatfield et al.
D577,883 S 10/2008 Link
7,438,846 B2 10/2008 John
D586,994 S 2/2009 Chang
D593,741 S 6/2009 Vico et al.
D608,991 S 2/2010 Lamont
7,676,955 B2 3/2010 Dojan et al.
7,704,430 B2 4/2010 Johnson et al.
D616,640 S 6/2010 Werman
D621,143 S 8/2010 Lamont
7,892,474 B2 2/2011 Shkolnik et al.
D638,616 S 5/2011 Gibson
8,110,135 B2 2/2012 El-Siblani
D659,358 S 5/2012 Van Zyll De Jong et al.
8,191,284 B2 6/2012 Cho
D666,391 S 9/2012 Van Zyll De Jong et al.
D672,949 S 12/2012 Bramani et al.
D686,402 S 7/2013 Portzline
8,522,454 B2 9/2013 Schindler et al.
D691,359 S 10/2013 Della Valle et al.
D695,502 S 12/2013 Miner
D696,004 S 12/2013 Della Valle et al.
D696,505 S 12/2013 Miner
D697,294 S 1/2014 Miner
D702,028 S 4/2014 Truelsen
D702,428 S 4/2014 Hlavacs
D703,425 S 4/2014 Lee
8,739,639 B2 6/2014 Owings et al.
D707,933 S 7/2014 McCourt
D709,274 S 7/2014 Roulo
8,776,396 B2 7/2014 Huynh
D711,637 S 8/2014 Miner
D713,628 S 9/2014 Greenspan
D741,586 S 10/2015 Truelsen
D743,154 S 11/2015 Nethongkome
D744,212 S 12/2015 Boudreau et al.
9,205,601 B2 12/2015 DeSimone et al.
9,211,678 B2 12/2015 DeSimone et al.
9,216,546 B2 12/2015 DeSimone et al.
D747,860 S 1/2016 De Costa Pereira Machado
D751,797 S 3/2016 Slimane
9,320,316 B2 4/2016 Guyan et al.
9,453,142 B2 9/2016 Rolland et al.
D769,593 S 10/2016 Chang
D773,162 S 12/2016 Lane, III et al.
D779,174 S 2/2017 De Montgolfier
D783,973 S 4/2017 Anceresi
D784,666 S 4/2017 Lok
D789,060 S 6/2017 Guyan et al.
D790,821 S 7/2017 Beers et al.
D792,689 S 7/2017 Mokos
D796,170 S 9/2017 Raysse
D796,806 S 9/2017 Durand
D798,561 S 10/2017 Ford
D799,184 S 10/2017 Chang
D800,432 S 10/2017 Klein
D802,896 S 11/2017 Rademacher et al.
D804,792 S 12/2017 De Montgolfier et al.
D809,752 S 2/2018 Campbell
D812,882 S 3/2018 Jenkins et al.
9,930,929 B2 4/2018 Cooper et al.
D816,961 S 5/2018 Bardea
D819,310 S 6/2018 Lashmore
D822,351 S 7/2018 DeAlmeida
10,010,133 B2 7/2018 Guyan
10,010,134 B2 7/2018 Guyan
10,016,013 B2 7/2018 Kormann et al.
10,034,516 B2 7/2018 Gheorghian et al.
D825,163 S 8/2018 Montross et al.
D825,165 S 8/2018 Gibson et al.
10,039,343 B2 8/2018 Guyan
D829,425 S 10/2018 Albrecht et al.
D831,315 S 10/2018 Mahoney
D831,317 S 10/2018 Jenkins et al.
10,104,934 B2 10/2018 Guyan
D836,892 S 1/2019 Jenkins et al.
D841,299 S 2/2019 Nikolic
D841,300 S 2/2019 Albrecht et al.
D841,301 S 2/2019 Albrecht et al.
D841,964 S 3/2019 Kaiserswerth
10,231,511 B2 3/2019 Guyan et al.
D844,953 S 4/2019 Chen et al.
D845,610 S 4/2019 Mayden et al.
10,259,171 B2 4/2019 Robeson et al.
D847,481 S 5/2019 Albrecht et al.
D848,716 S 5/2019 Shyllon
D849,382 S 5/2019 Jenkins et al.
D850,083 S 6/2019 Jenkins et al.
D851,873 S 6/2019 Maier
D854,300 S 7/2019 Evans
D855,957 S 8/2019 Evans
D857,350 S 8/2019 Hardy
D857,360 S 8/2019 Hardy
D857,362 S 8/2019 Thompson
D858,066 S 9/2019 Hatfield
D859,801 S 9/2019 Jenkins et al.
D860,614 S 9/2019 Bishoff
D862,051 S 10/2019 Goussev et al.
D862,866 S 10/2019 Albrecht et al.
10,426,226 B2 10/2019 Guyan et al.
10,434,706 B2 10/2019 Robeson et al.
D869,830 S 12/2019 Lucas et al.
D871,033 S 12/2019 Nikolic
D872,426 S 1/2020 Taylor
D873,546 S 1/2020 Henrichot
D876,056 S 2/2020 Henrichot
D879,428 S 3/2020 Braun et al.
D879,434 S 3/2020 Fick et al.
10,575,588 B2 3/2020 Perrault et al.
D880,120 S 4/2020 Fick et al.
D880,122 S 4/2020 Fick et al.
D880,131 S 4/2020 Fick et al.
D882,227 S 4/2020 Braun et al.
10,639,861 B2 5/2020 Minh et al.
D890,485 S 7/2020 Perrault et al.
D907,904 S 1/2021 Perrault et al.

(56) References Cited

U.S. PATENT DOCUMENTS

| | | | | |
|---|---|---|---|---|
| 2002/0078598 | A1 | 6/2002 | Bell | |
| 2004/0087230 | A1 | 5/2004 | Wildeman | |
| 2006/0201028 | A1 | 9/2006 | Chan et al. | |
| 2007/0011914 | A1 | 1/2007 | Keen et al. | |
| 2007/0043582 | A1 | 2/2007 | Peveto et al. | |
| 2008/0289218 | A1 | 11/2008 | Nakano | |
| 2009/0126225 | A1 | 5/2009 | Jarvis | |
| 2009/0139112 | A1 | 6/2009 | Garneau | |
| 2009/0183392 | A1 | 7/2009 | Shane | |
| 2009/0293309 | A1 | 12/2009 | Keating et al. | |
| 2010/0122471 | A1 | 5/2010 | Edington et al. | |
| 2010/0170106 | A1 | 7/2010 | Brewer et al. | |
| 2010/0199520 | A1 | 8/2010 | Dua et al. | |
| 2010/0251565 | A1 | 10/2010 | Litchfield et al. | |
| 2010/0281714 | A1 | 11/2010 | Carboy et al. | |
| 2011/0099855 | A1 | 5/2011 | Cho | |
| 2012/0117825 | A9 | 5/2012 | Jarvis | |
| 2012/0178259 | A1 | 7/2012 | Miyazaki et al. | |
| 2012/0180335 | A1 | 7/2012 | Mahoney | |
| 2012/0186107 | A1 | 7/2012 | Crary et al. | |
| 2013/0118036 | A1 | 5/2013 | Gibson | |
| 2013/0145653 | A1 | 6/2013 | Bradford | |
| 2013/0171019 | A1 | 7/2013 | Gessler et al. | |
| 2013/0292862 | A1 | 11/2013 | Joyce | |
| 2013/0295212 | A1 | 11/2013 | Chen et al. | |
| 2014/0020191 | A1 | 1/2014 | Jones et al. | |
| 2014/0026773 | A1 | 1/2014 | Miller | |
| 2014/0029030 | A1 | 1/2014 | Miller | |
| 2014/0109441 | A1 | 4/2014 | McDowell et al. | |
| 2014/0150297 | A1 | 6/2014 | Holmes et al. | |
| 2014/0182170 | A1 | 7/2014 | Wawrousek et al. | |
| 2014/0223783 | A1 | 8/2014 | Wardlaw et al. | |
| 2014/0226773 | A1 | 8/2014 | Toth et al. | |
| 2014/0259779 | A1 | 9/2014 | Hashish et al. | |
| 2014/0259787 | A1 | 9/2014 | Guyan et al. | |
| 2014/0259788 | A1 | 9/2014 | Dojan et al. | |
| 2014/0259789 | A1 | 9/2014 | Dojan et al. | |
| 2014/0299009 | A1 | 10/2014 | Miller et al. | |
| 2014/0300675 | A1 | 10/2014 | Miller et al. | |
| 2014/0300676 | A1 | 10/2014 | Miller et al. | |
| 2014/0310991 | A1 | 10/2014 | Greene et al. | |
| 2015/0000161 | A1 | 1/2015 | Peyton et al. | |
| 2015/0033577 | A1 | 2/2015 | Dahl et al. | |
| 2015/0033579 | A1 | 2/2015 | Barnes et al. | |
| 2015/0033581 | A1 | 2/2015 | Barnes et al. | |
| 2015/0089841 | A1 | 4/2015 | Smaldone et al. | |
| 2015/0181976 | A1 | 7/2015 | Cooper et al. | |
| 2015/0223560 | A1 | 8/2015 | Wawrousek et al. | |
| 2015/0245686 | A1 | 9/2015 | Cross | |
| 2015/0331402 | A1 | 11/2015 | Lin et al. | |
| 2015/0351493 | A1* | 12/2015 | Ashcroft | A43B 13/18 36/132 |
| 2015/0360419 | A1 | 12/2015 | Willis et al. | |
| 2016/0051009 | A1 | 2/2016 | Kormann et al. | |
| 2016/0122493 | A1 | 5/2016 | Farris et al. | |
| 2016/0137839 | A1 | 5/2016 | Rolland et al. | |
| 2016/0160077 | A1 | 6/2016 | Rolland et al. | |
| 2016/0180440 | A1 | 6/2016 | Dibenedetto et al. | |
| 2016/0288376 | A1 | 10/2016 | Sun et al. | |
| 2016/0295971 | A1 | 10/2016 | Arnese et al. | |
| 2016/0324260 | A1 | 11/2016 | Guyan | |
| 2016/0324261 | A1 | 11/2016 | Guyan | |
| 2016/0360828 | A1 | 12/2016 | Guyan | |
| 2016/0374428 | A1 | 12/2016 | Kormann et al. | |
| 2017/0129167 | A1 | 5/2017 | Castanon | |
| 2017/0129169 | A1 | 5/2017 | Batchelder et al. | |
| 2017/0150778 | A1 | 6/2017 | Youngs et al. | |
| 2018/0014606 | A1 | 1/2018 | Mokos | |
| 2018/0070736 | A1 | 3/2018 | Achten et al. | |
| 2018/0103719 | A1 | 4/2018 | Chen | |
| 2018/0126630 | A1 | 5/2018 | Panzer et al. | |
| 2018/0243976 | A1 | 8/2018 | Feller | |
| 2018/0271211 | A1 | 9/2018 | Perrault et al. | |
| 2018/0271213 | A1 | 9/2018 | Perrault et al. | |
| 2018/0290374 | A1 | 10/2018 | Willis et al. | |
| 2018/0368518 | A1 | 12/2018 | Re et al. | |
| 2019/0069632 | A1 | 3/2019 | Meschter | |
| 2019/0098960 | A1 | 4/2019 | Weisskopf et al. | |
| 2019/0160733 | A1 | 5/2019 | Mirkin et al. | |
| 2019/0223543 | A1 | 7/2019 | Tamm et al. | |
| 2019/0223551 | A1 | 7/2019 | Hoffer et al. | |
| 2019/0269200 | A1 | 9/2019 | Tseng | |
| 2019/0289960 | A1 | 9/2019 | Loveder | |
| 2020/0156308 | A1 | 5/2020 | Ramos et al. | |

FOREIGN PATENT DOCUMENTS

| | | | |
|---|---|---|---|
| CN | 203378623 | U | 1/2014 |
| CN | 209391169 | U | 9/2019 |
| CN | 209403686 | U | 9/2019 |
| EP | 0526892 | A2 | 2/1993 |
| EP | 2564719 | A1 | 3/2013 |
| EP | 2424398 | B1 | 12/2015 |
| EP | 3013171 | A1 | 5/2016 |
| EP | 3165109 | A1 | 5/2017 |
| ES | 2442448 | A1 | 2/2014 |
| ES | 2578730 | A1 | 7/2016 |
| JP | 2002238609 | A | 8/2002 |
| JP | 2011251190 | A | 12/2011 |
| JP | 2014151201 | A | 8/2014 |
| JP | 3192899 | U | 9/2014 |
| WO | WO-2010126708 | A2 | 11/2010 |
| WO | WO-2014008331 | A2 | 1/2014 |
| WO | WO-2014009587 | A1 | 1/2014 |
| WO | WO-2014015037 | A2 | 1/2014 |
| WO | WO-2014100462 | A1 | 6/2014 |
| WO | WO-2015164234 | A1 | 10/2015 |
| WO | WO-2015169941 | A1 | 11/2015 |
| WO | WO-2015169942 | A1 | 11/2015 |
| WO | WO-2016066750 | A1 | 5/2016 |
| WO | WO-2017210298 | A1 | 12/2017 |

OTHER PUBLICATIONS

Green, D., Adidas is finally bringing 3D-printed shoes into the mainstream,Business Insider.com, Dennis Green, Retrieved from the Internet: (URL:https://www.businessinsider.com/adidas-releases-futurecraft-4d-shoe-2017-4/commerce-on-business-insider), (Year: 2017).

Janusziewicz, R., et al., "Layerless Fabrication With Continuous Liquid Interface Production," Proceedings of the National Academy of Sciences of the United States of America 113(42):11703-11708, National Academy of Sciences, United States (Oct. 2016).

Nikolic, I., Reebok Flexagon Training Shoes, Behance.net, Ilija Nikolic, Retrieved from the Internet (URL: https://www.behance.net/gallery/68953047/REEBOK-FLEXAGON-Training-Shoes?t- racking_source=curated_galleries_list) 2018, 10 pages.

Panetta., et al., "Elastic Textures for Additive Fabrication," ACM Transactions on Graphics 34(4), Article No. 135 (Aug. 2015).

Pearson, D., Adidas is giving Olympic athletes its first-ever 3D-printed shoes,Highsnobiety.com, Retrieved from the Internet: (URL:https://www.highsnobiety.com/2016/08/11/adidas-3d-printed-shoes-olympics/), (Year: 2016).

Reebok Flexagon, Retrieved from the Internet (URL: https://www.reebok.com/us/reebok-flexagon/CN2583.html), 2018.

Richard, B., Here's what 3D printed Future Craft adidas Yeezy boosts would look like Yeezys geared up for the future Retrieved from the Internet: (URL:https://solecollector.com/news/2015/11/adidas-yeezy-futurecraft-3d-print), (Year: 2015).

Tumbleston, J.R., et al., "Continuous Liquid Interface Production of 3d Objects," Science 347(6228):1349-1352, American Association for the Advancement of Science, United States (Mar. 2015).

Worman, C., Top Tennis Shoes Featuring a 6-Month Outsole Warranty, Retrieved from the Internet (URL: https://blogs.tennisexpress.com/blogs/top-tennis-shoes-featuring- -a-6-month-outsole-warranty/), (Year: 2018), 11 pages.

* cited by examiner

FOOTWEAR MIDSOLE WITH WARPED LATTICE STRUCTURE AND METHOD OF MAKING THE SAME

CROSS-REFERENCE TO RELATED APPLICATIONS

This application is a continuation of U.S. application Ser. No. 17/187,304, filed Feb. 26, 2021, which is a divisional of U.S. application Ser. No. 15/898,000, filed Feb. 15, 2018, which is a continuation-in-part of and claims priority to U.S. application Ser. No. 15/470,570, filed Mar. 27, 2017. Each of these applications is incorporated herein by reference in its entirety.

FIELD

The described embodiments generally relate to midsoles for articles of footwear. In particular, described embodiments relate to midsoles including a three-dimensional mesh constructed of interconnected unit cells arranged in a warped cubic lattice structure and methods of making the same.

BACKGROUND

Individuals are often concerned with the amount of cushioning an article of footwear provides. This is true for articles of footwear worn for non-performance activities, such as a leisurely stroll, and for performance activities, such as running, because throughout the course of an average day, the feet and legs of an individual are subjected to substantial impact forces. When an article of footwear contacts a surface, considerable forces may act on the article of footwear and, correspondingly, the wearer's foot. The sole of an article of footwear functions, in part, to provide cushioning to the wearer's foot and to protect it from these forces. In addition to cushioning, individuals may be concerned with the durability, weight, and/or comfort of an article of footwear. Durable footwear will properly function for an extended period of time. Lightweight footwear minimizes the weight an individual has to carry on his or her feet and may be comfortable for an individual. Customized footwear may increase comfort for an individual because it is tailored to the individual's needs and/or foot anatomy.

The human foot is a complex and remarkable piece of machinery, capable of withstanding and dissipating many impact forces. The natural padding of fat at the heel and forefoot, as well as the flexibility of the arch, help to cushion the foot. Although the human foot possesses natural cushioning and rebounding characteristics, the foot alone is incapable of effectively overcoming many of the forces encountered during every day activity. Unless an individual is wearing shoes that provide proper cushioning and support, the soreness and fatigue associated with every day activity is more acute, and its onset may be accelerated. This discomfort for the wearer may diminish the incentive for further activity. Equally important, inadequately cushioned footwear can lead to injuries such as blisters; muscle, tendon, and ligament damage; and bone stress fractures. Improper footwear can also lead to other ailments, including back pain.

Proper footwear should be durable, comfortable, and provide other beneficial characteristics for an individual. Therefore, a continuing need exists for innovations in footwear.

BRIEF SUMMARY OF THE INVENTION

Some embodiments are directed to a midsole for an article of footwear, the midsole including a three-dimensional mesh including a plurality of interconnected unit cells, each interconnected unit cell including a plurality of struts defining a three-dimensional shape and a plurality of nodes at which one or more struts are connected, where each node includes a valence number defined by the number of struts that are connected at that node and the valence number of the nodes varies in a longitudinal direction along the length of the midsole between a forefoot end of the midsole and a heel end of the midsole.

In some embodiments, the valence number of the nodes may vary in a transverse direction along the width of the midsole between a lateral side of the midsole and a medial side of the midsole.

In some embodiments, the average value for the valence numbers of nodes in a forefoot portion of the midsole may be greater than the average value for the valence numbers of nodes in a heel portion of the midsole.

In some embodiments, the size of the unit cells may vary in the midsole. In some embodiments, the average size of the unit cells positioned in a forefoot portion of the midsole may be less than the average size of the unit cells positioned in a heel portion of the midsole.

In some embodiments, the size of the unit cells may vary in the longitudinal direction along the length of the midsole between a forefoot end of the midsole and a heel end of the midsole. In some embodiments, the average size of the unit cells may increase in the longitudinal direction along the length of the midsole from the forefoot end of the midsole to the heel end of the midsole.

In some embodiments, the size of the unit cells may vary in a vertical direction between a top side of the midsole and a bottom side of the midsole. In some embodiments, the average size of the unit cells may increase in the vertical direction from the bottom side of the midsole to the top side of the midsole.

In some embodiments, each unit cell in a midsole may have the same base geometry.

In some embodiments, the unit cells may have a valence number in the range of 1 to 12.

In some embodiments, the midsole may include a plurality of unit cells having a first base geometry and a plurality unit cells having a second base geometry different from the first base geometry. In some embodiments, a plurality of unit cells having the first base geometry may be located in a forefoot portion of the midsole and a plurality of unit cells having the second base geometry may be located in a heel portion of the midsole. In some embodiments, a midfoot portion of the midsole may include a plurality of unit cells having the first base geometry and a plurality of unit cells having the second base geometry.

In some embodiments, 90% or more of all the unit cells in a midsole may be a complete unit cell.

In some embodiments, the variation in the valence number in the longitudinal direction along the length of the midsole may be based on a biometric data profile collected for an individual. In some embodiments, the biometric data profile may include information about the individual's gait collected from motion sensors coupled to the individual's foot during a test procedure.

In some embodiments, the variation in the size of the unit cells in a midsole may be based on a biometric data profile collected for an individual.

In some embodiments, the location of the plurality of unit cells having the first base geometry and the location of the plurality of unit cells having the second base geometry may be based on a biometric data profile collected for an individual.

Some embodiments are directed to a midsole for an article of footwear, the midsole including a three-dimensional mesh including a plurality of interconnected unit cells organized in a warped cubic lattice structure that defines a volume of the midsole, each interconnected unit cell including a plurality of struts defining a three-dimensional shape, and the warped cubic lattice structure including a plurality of warped cubic lattice cells having different volumes and cubic geometries, wherein the warped cubic lattice structure defines a plurality of nodes at which one or more struts are connected and the warped cubic lattice structure is warped in a longitudinal direction along the length of the midsole, in a transverse direction along the width of the midsole, and in a vertical direction along the height of the midsole.

In some embodiments, the size of the unit cells in the midsole may vary based on the volume of the cubic cell in which a unit cell is positioned. In some embodiments, the geometry of the unit cells in the midsole may vary based on the geometry of the cubic cell in which a unit cell is positioned.

In some embodiments, two or more interconnected unit cells may be positioned in a single warped cubic lattice cell. In some embodiments, the two or more interconnected unit cells positioned in a single warped cubic lattice cell may be unit cells having different base geometries.

In some embodiments, the volume and cubic geometry of the warped cubic lattice cells in the warped cubic lattice structure may be based on a biometric data profile collected for an individual.

Some embodiments are directed to a method of making a midsole for an article of footwear, the method including generating a warped cubic lattice structure based on a biometric data profile collected for an individual, the warped cubic lattice structure: defining a volume of the midsole, including a plurality of cubic lattice cells having different volumes and cubic geometries, and defining a plurality of nodes; populating each cubic lattice cell with one or more partial lattice unit cells based on the biometric data profile, the partial lattice unit cells forming a cell lattice including lattice unit cells connected to each other at one or more of the nodes; and forming a three-dimensional mesh based on the biometric data profile, the three-dimensional mesh including a plurality of interconnected unit cells, each unit cell including a plurality of struts defining a three-dimensional shape corresponding to the shape of a respective lattice unit cell, thereby forming the midsole.

In some embodiments, the biometric data profile may include information about the individual's gait collected from motion sensors coupled to the individual's foot during a testing procedure. In some embodiments, the motion sensors may include at least one of: acceleration sensors and magnetic field sensors. In some embodiments, the information about the individual's gait may include information about how the individual's foot rolls when it contacts the ground and information about how the individual's foot strikes the ground.

In some embodiments, forming the three-dimensional mesh may include an additive manufacturing process.

In some embodiments, forming the three-dimensional mesh may include a continuous liquid interface production process.

BRIEF DESCRIPTION OF THE DRAWINGS/FIGURES

DETAILED DESCRIPTION OF THE INVENTION

Figure 1:
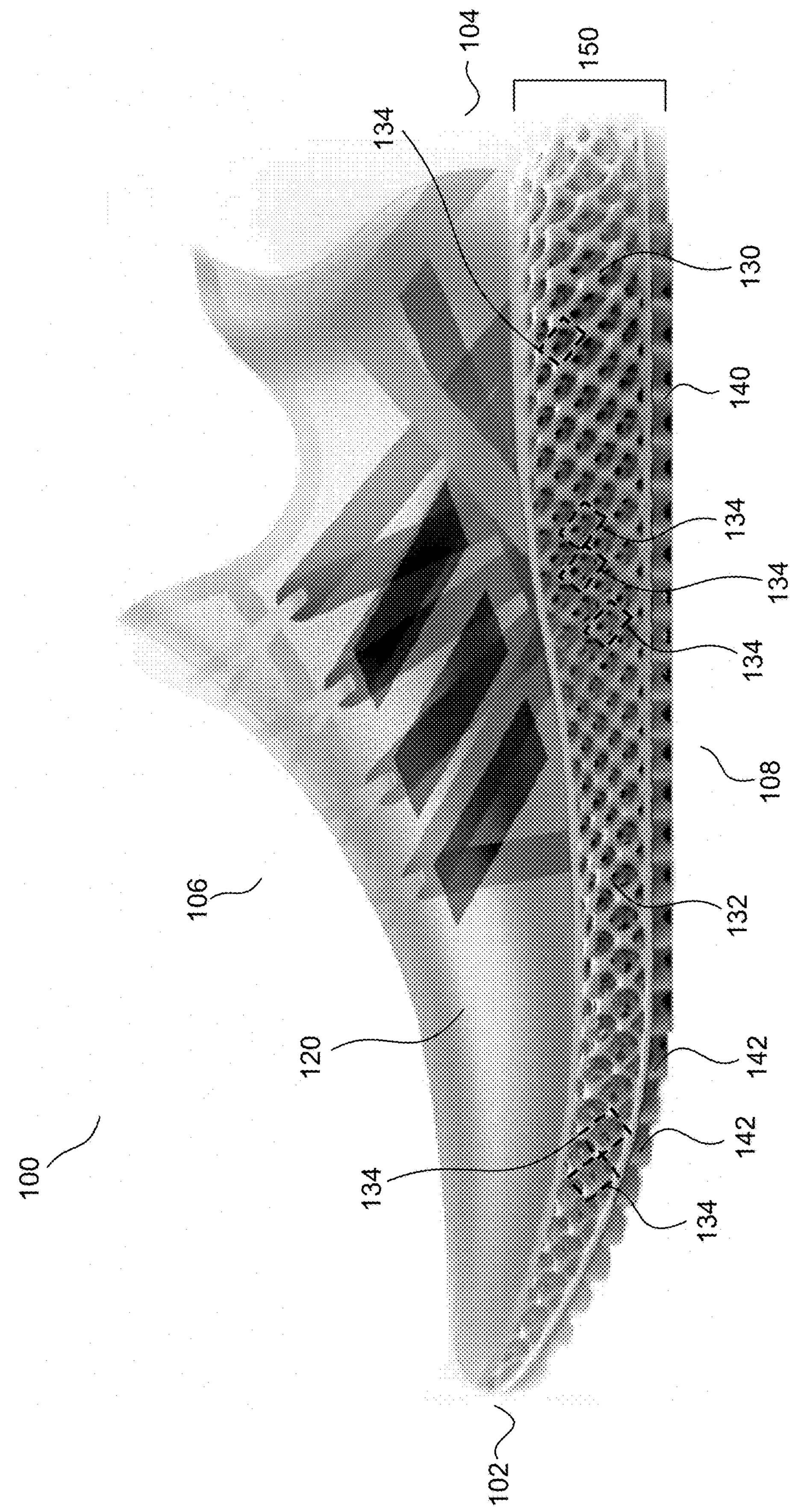
FIG. 1 is a medial side view of an article of footwear according to some embodiments.

The present invention(s) will now be described in detail with reference to embodiments thereof as illustrated in the accompanying drawings. References to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

An article of footwear has many purposes. Among other things, an article of footwear may cushion a wearer's foot, support a wearer's foot, protect a wearer's foot (e.g., from injury), and optimize the performance of a wearer's foot. Each of these purposes, alone or in combination, provides for a comfortable article of footwear suitable for use in a variety of scenarios (e.g., exercise and every day activities). The features of an article of footwear (e.g., shape, components, and materials used to make footwear) may be altered to produce desired characteristics, for example, cushioning, support, stability, ride, and propulsion characteristics.

Stability provided by an article of footwear may protect a wearer's foot from injury, such as spraining his or her ankle. Propulsion provided by an article of footwear may optimize the performance of a wearer's foot by, for example, maximizing the energy transfer from the individual's foot to the surface his or her foot is in contact with (e.g., the ground) via the article of footwear. Maximizing the energy transfer between the individual's foot and a surface (i.e., reducing energy lost via and/or absorbed by an article of footwear) may help an athlete, for example, accelerate faster, maintain a higher maximum speed, change directions faster, and jump higher. Cushioning and ride characteristics provided by an article of footwear may provide comfort for an individual during an athletic or everyday activity.

The anatomy of the human foot creates a shape and contour for the bottom of the foot that results in varying degrees of pressure (force) on the bottom of the foot when the foot is in contact with the ground (e.g., while standing still, walking, running, etc.). The varying degrees of pressure create areas on the foot subject various pressure forces and stresses. Some areas may be subject to relatively high pressures/stresses and others may be subject to relatively low pressures/stresses. To provide comfort, areas subject to relatively high degrees of pressure/stress may require additional cushioning or support compared to areas subject to relatively low degrees of pressure/stress.

Moreover, the shape and contour of the bottom of different individuals' feet create different pressure/stress profiles for different individuals' feet. This may also be true for the left and right foot of a single individual. Accordingly, the cushioning and/or support needs for one individual's feet (or the left and right feet of a single individual) may be different. The cushioning and/or support needs may be dependent not only on an individual's foot anatomy, but also the individual's natural gait.

In some embodiments, the midsoles and articles of footwear having midsoles discussed herein may include a three-dimensional mesh composed of interconnected unit cells. The geometry, interconnection, and arrangement of the interconnected unit cells may be customized for a particular individual, or group of individuals. The geometry, interconnection, and arrangement of the interconnected unit cells may be based, in whole or in part, on a biometric data profile for an individual's foot. The interconnected unit cells may be arranged in a warped cubic lattice structure, which may also be based on the biometric data profile for an individual's foot.

The geometry, interconnection, and arrangement of the unit cells within a three-dimensional mesh may offer a multitude of different options for customizing (tailoring) a midsole to an individual's, or group of individuals' needs. For example, one or more of the following may be tailored for an individual or group of individuals: (i) the volumetric shape of a midsole, (ii) the stiffness (including for example compressive strength, shear strength and/or bending strength and/or torsional stiffness) of struts defining interconnected unit cells, (iii) the number of unit cells per unit volume (i.e., the density of unit cells), (iv) the degree of interconnection between unit cells (referred to herein as "valence") and (v)

the base geometry of the unit cells. Each parameter (i)-(v) may vary between different zones or portions on a midsole to provide desired characteristics, for example cushioning, support, stability, ride, and/or propulsion characteristics for an individual, or group of individuals.

Midsoles including a three-dimensional mesh as discussed herein may be manufactured using one or more additive manufacturing methods. Additive manufacturing methods allow for fabrication of three-dimensional objects without the need for a mold. Instead, the objects may be manufactured layer by layer, e.g. from liquid material, or from a powder material. Additive manufacturing methods may reduce costs for a manufacturer, and in turn a consumer, of a product (e.g., a shoe) by reducing or eliminating the need for molds. Integral manufacturing of a midsole using additive manufacturing may make the assembly of separate elements of the midsole unnecessary. Similarly, an additively manufactured midsole may be fabricated from single material, which may facilitate easy recycling of the midsole.

Also, since molds are not required, additive manufacturing methods facilitate customization of products. For example, a midsole can be customized to a particular individual, or group of individuals, in a more cost effective way with an additive manufacturing method compared to a traditional molding method.

Due to the nature of additive manufacturing methods, additive manufacturing methods can be leveraged to provide customized and affordable footwear for individuals. Exemplary additive manufacturing techniques include for example, selective laser sintering, selective laser melting, selective heat sintering, stereo lithography, fused deposition modeling, or 3D printing in general. Various additive manufacturing techniques related to articles of footwear are described for example in US 2009/0126225, WO 2010/126708, US 2014/0300676, US 2014/0300675, US 2014/0299009, US 2014/0026773, US 2014/0029030, WO 2014/008331, WO 2014/015037, US 2014/0020191, EP 2 564 719, EP 2 424 398 and US 2012/0117825.

Using the additive manufacturing methods discussed herein, customized midsoles may be provided with short lead times. For example, a midsole may be customized for, among other things, the width and/or length of an individual's foot, the weight of an individual, an individual's gait, and/or the type of footwear with which a midsole is intended to be used. In some embodiments, a midsole may comprise at least two regions that have different physical properties, for example different unit cell densities, different stiffness, and/or different unit cell interconnection. In some embodiments, midsoles discussed herein may be formed using an additive manufacturing method that does not require post-formation processing steps, such as cutting away undesirable parts of a midsole. Eliminating post-formation processing steps facilitates manufacturing consistency and reproducibility.

In some embodiments, the physical properties of a three-dimensional mesh may be tailored by tailoring the volume, cell size, and/or warped geometry of a warped lattice structure in which unit cells of the three-dimensional mesh are arranged. In some embodiments, the physical properties of a three-dimensional mesh may be tailored by tailoring the thickness of struts defining the unit cells of the three-dimensional mesh. In some embodiments, the physical properties of a three-dimensional mesh may be tailored by tailoring the density of unit cells in the three-dimensional mesh. The density of unit cells may be tailored by tailoring at least one of: the size of the unit cells, the degree of interconnection between the unit cells, and the base geometry of the unit cells. In some embodiments, the physical properties of a three-dimensional mesh may be tailored by tailoring the material(s) used to form the three-dimensional mesh.

In some embodiments, the base geometry of unit cells may be approximately constant along the length and width of a midsole. For example, the base geometry (e.g., cubic, tetrahedral, dodecahedral, etc.) of unit cells may be approximately constant along the length and width of a midsole. In some embodiments, the base geometry of unit cells may vary in a three-dimensional mesh. In some embodiments, a three-dimensional mesh may include at least two unit cells with different base geometries. For example, a first base geometry (e.g. unit cells designed as rhombic dodecahedrons), may be combined with other unit cells including a second base geometry (e.g., pentagonal dodecahedrons, cubes, cuboids, prisms, parallelepipeds, etc.).

In some embodiments, a three-dimensional mesh may include a first region with a plurality of unit cells having a first base geometry and a second region with a plurality of unit cells having a second base geometry. The base geometries of the regions may be adapted to the specific requirements of that region. For example, a less dense unit cell geometry (e.g., cubic) may be used in a region with reduced density and/or stiffness requirements. Additionally or alternatively, one or more dimensions of the unit cells in the first region may differ from those of the unit cells in the second region.

Figure 2:
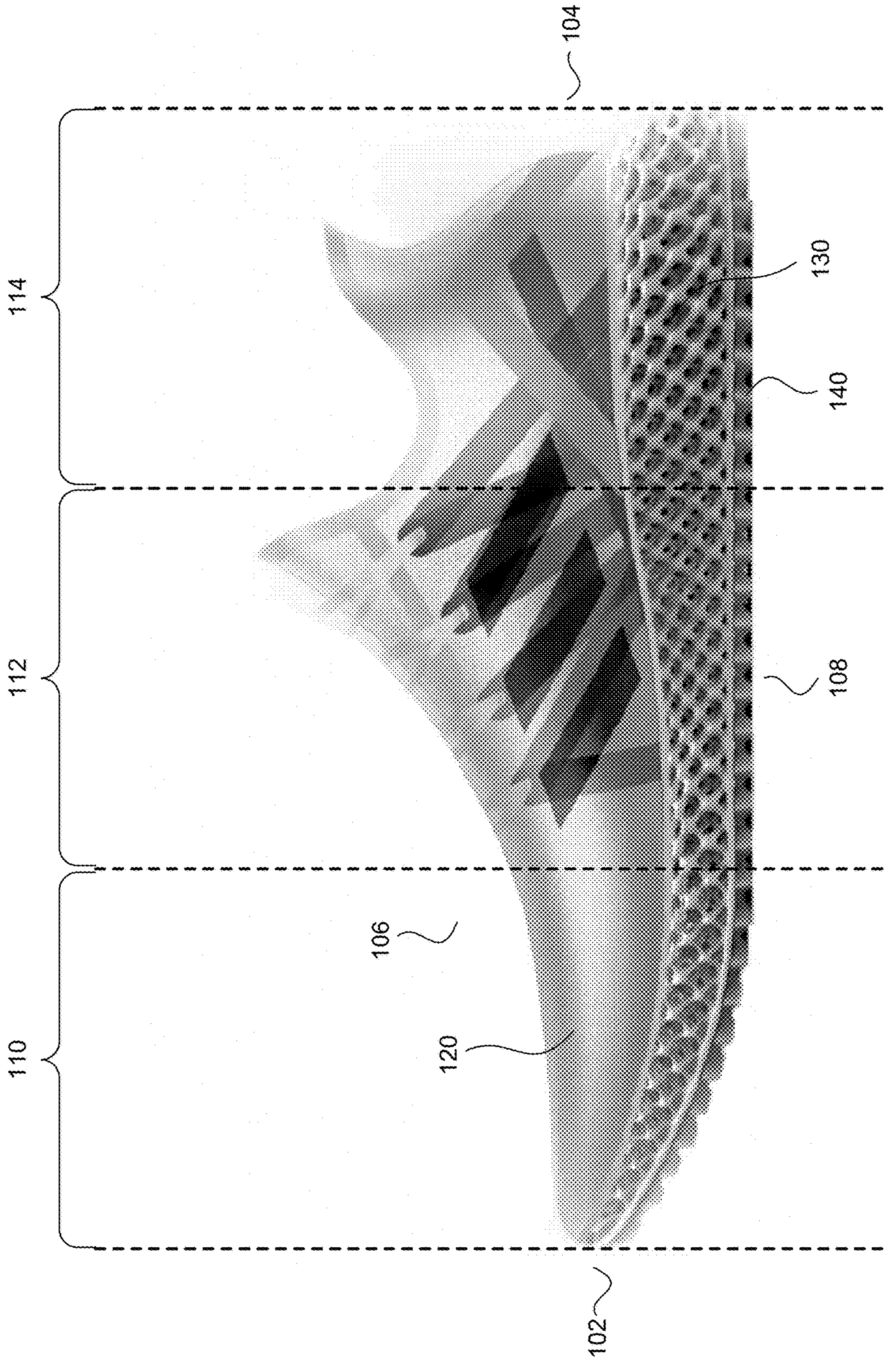
FIG. 2 is a medial side of an article of footwear according to some embodiments showing portions of the article of footwear.
Figure 3:
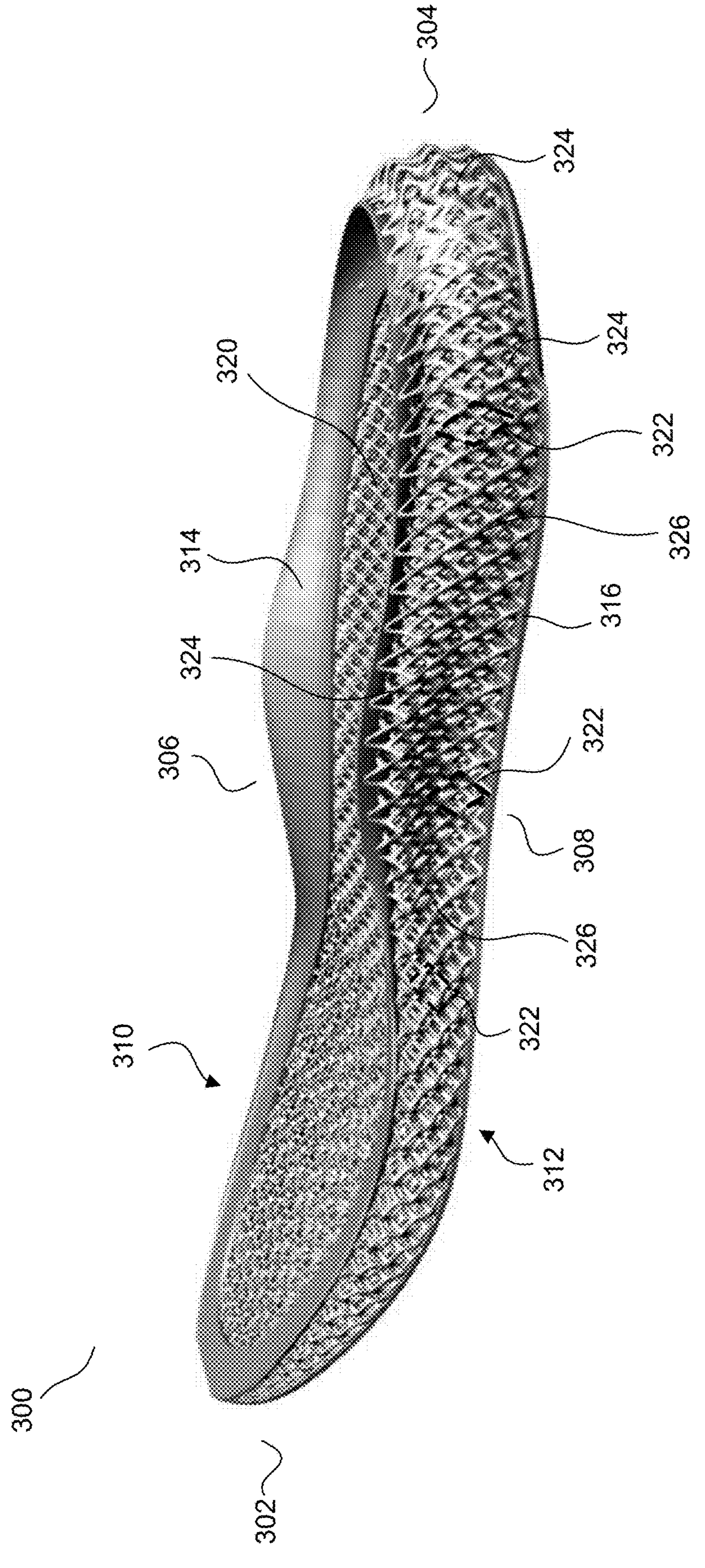
FIG. 3 is a perspective view of a midsole according to some embodiments.
Figure 4:
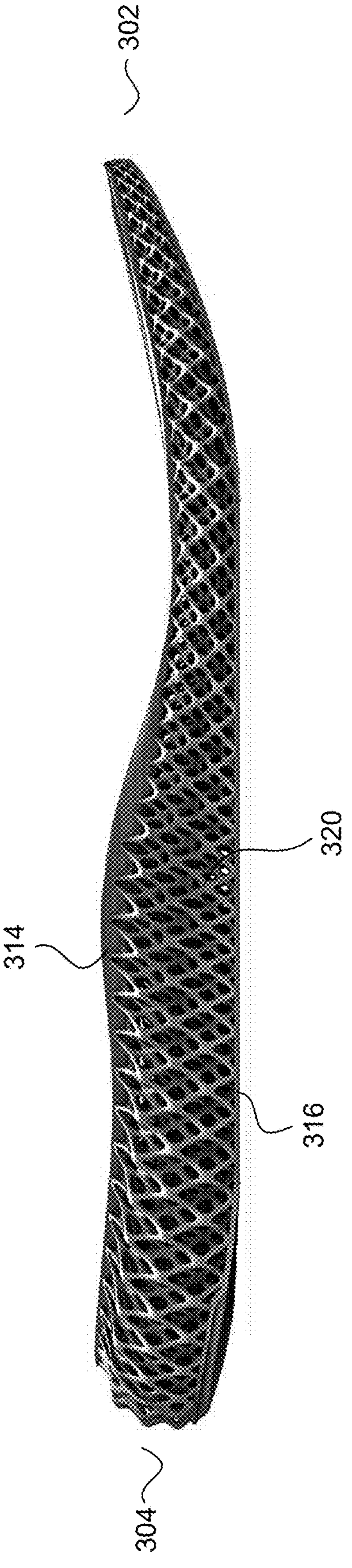
FIG. 4 is a side view of a midsole according to some embodiments.

FIGS. 1 and 2 show an article of footwear 100 according to some embodiments. Article of footwear 100 may include an upper 120 coupled to a midsole 130. Article of footwear 100 includes a forefoot end 102, a heel end 104, a medial side 106, and a lateral side 108 opposite medial side 106. Also, as shown for example in FIG. 2, article of footwear 100 includes a forefoot portion 110, a midfoot portion 112, and a heel portion 114. Portions 110, 112, and 114 are not intended to demarcate precise areas of article of footwear 100. Rather, portions 110, 112, and 114 are intended to represent general areas of article of footwear 100 that provide a frame of reference. Although portions 110, 112, and 114 apply generally to article of footwear 100, references to portions 110, 112, and 114 also may apply specifically to upper 120 or midsole 130, or individual components of upper 120 or midsole 130.

In some embodiments, article of footwear 100 may include an outsole 140 coupled to midsole 130. Together, midsole 130 and outsole 140 may define a sole 150 of article of footwear 100. In some embodiments, outsole 140 may be directly manufactured (e.g., 3-D printed) on the bottom side of midsole 130. In some embodiments, outsole 140 and midsole 130 may be manufactured in one manufacturing process (e.g., one 3-D printing process) and no bonding, e.g. via adhesives, may be necessary. In some embodiments, outsole 140 may include a plurality of protrusions 142 to provide traction for article of footwear 100. In some embodiments, midsole 130 may be the same as or similar to midsole, 300, midsole 2100 or midsole 2200.

As shown for example in FIG. 1, midsole 130 may include a three-dimensional mesh 132 composed of a plurality of interconnected unit cells 134. In some embodiments, midsole 130 may be customized for an individual, or a group of individuals. In such embodiments, an individual's gait may be analyzed using, for example, a Vicon® Motion Capture system with force plates, or a Run Genie® system. Such gait analysis systems may produce a biometric data profile for an individual that may be used to customize midsole 130 (see e.g., method 1000 described in connection with FIG. 10).

Based at least in part on the data collected, properties of midsole 130, three-dimensional mesh 132, and/or unit cells 134 may be customized to an individual's cushioning, support, stability, ride, and/or propulsion needs. In some embodiments, midsole 130, three-dimensional mesh 132, and/or unit cells 134 may also be customized based on an individual's athletic needs (e.g., the type of sport the individual plays and/or the amount of time the individual spends exercising).

Parameters of midsole 130 that may be customized to an individual's needs include, but are not limited to: i) the volumetric shape of midsole 130, ii) the stiffness (including for example compressive strength, shear strength and/or bending strength and/or torsional stiffness) of struts defining the interconnected unit cells 134, (iii) the number of unit cells 134 per unit volume (i.e., the density of unit cells), (iv) the degree of interconnection between unit cells 134 (referred to herein as "valence"), and (v) the base geometry of the unit cells 134. Parameters (i)-(v) may vary between different zones or portions of midsole 130 (e.g., forefoot portion 110, a midfoot portion 112, and a heel portion 114) to provide targeted characteristics in different zones or portions of midsole 130 based on an individual's needs.

In some embodiments, one or more of these parameters may be customized based on an individual's objective athletic goals. For example, a long distance runner may desire a midsole 130 that provides a high degree of cushioning for long distance runs. As another example, a football player may desire a relatively stiff midsole 130 that resists deformation when upper 120 acts on midsole 130, thereby providing a high degree of support for his or her feet (e.g., a high degree of support for his or her ankles). As a further example, a sprinter may desire a relative stiff and lightweight midsole 130 that provides a high a degree of propulsion (i.e., efficient energy transfer from the individual's foot to the ground).

In some embodiments, midsole 130 may be customized to a particular individual's foot or gait, or a particular group of individual's feet or gait. This customization may be based on unique user characteristics provided by, for example, a Run Genie® system. In some embodiments, midsole 130 may be customized for an individual to modify an irregularity in the individual's gait. In such embodiments, midsole 130 may provide stability and/or propulsion characteristics to modify the individual's gait (i.e., modify his or her gait to a preferred motion). Correcting/modifying an individual's gait to preferred motion may reduce discomfort for an individual during exercise.

In some embodiments, different zones or portions of midsole 130 (e.g., portions 110, 112, and 114) may be customized or tuned to a particular individual's foot or gait, or a particular group of individual's feet or gait. Different zones or portions of midsole 130 may customized to an individual's gait by i) adjusting the volumetric shape of midsole 130, ii) adjusting the stiffness (including for example compressive strength, shear strength and/or bending strength and/or torsional stiffness) of struts defining the interconnected unit cells 134, (iii) adjusting the number of unit cells 134 per unit volume (i.e., the density of unit cells), (iv) adjusting the degree of interconnection between unit cells 134 (referred to herein as "valence"), and/or (v) adjusting the base geometry of the unit cells 134.

For example, a heel striker may be best served by a midsole 130 having a heel portion 114 that provides a high degree of cushioning, but a forefoot striker may be best served by a midsole 130 having a forefoot portion 110 that provides a high degree of cushioning. As another example, a heel striker may be best served by a midsole 130 with a heel portion 114 having a perimeter zone with a large degree stability, but a forefoot striker may be best served by a forefoot portion 110 having a perimeter zone with a large degree of stability.

Upper 120 and sole 150 may be configured for a specific type of footwear, including, but not limited to, a running shoe, a hiking shoe, a water shoe, a training shoe, a fitness shoe, a dancing shoe, a biking shoe, a tennis shoe, a cleat (e.g., a baseball cleat, a soccer cleat, or a football cleat), a basketball shoe, a boot, a walking shoe, a casual shoe, or a dress shoc. Moreover, sole 150 may be sized and shaped to provide a desired combination of cushioning, stability, propulsion, and ride characteristics to article of footwear 100. The term "ride" may be used herein in describing some embodiments as an indication of the sense of smoothness or flow occurring during a gait cycle including heel strike, midfoot stance, toe off, and the transitions between these stages. In some embodiments, sole 150 may provide particular ride features including, but not limited to, appropriate control of pronation and supination, support of natural movement, support of unconstrained or less constrained movement, appropriate management of rates of change and transition, and combinations thereof.

Sole 150 and portions thereof (e.g., midsole 130 and outsole 140) may comprise material(s) for providing desired cushioning, ride, propulsion, support, and stability. Suitable materials for sole 150 (e.g., midsole 130 and/or outsole 140) include, but are not limited to, a foam, a rubber, ethyl vinyl acetate (EVA), thermoplastic polyurethane (TPU), expanded thermoplastic polyurethane (eTPU), polyether block amide (PEBA), expanded polyether block amide (cPEBA), thermoplastic rubber (TPR), and a thermoplastic polyurethane (PU). In some embodiments, the foam may comprise, for example, an EVA based foam or a PU based foam and the foam may be an open-cell foam or a closed-cell foam. In some embodiments, midsole 130 and/or outsole 140 may comprise elastomers, thermoplastic elastomers (TPE), foam-like plastics, gel-like plastics, and combinations thereof. In some embodiments, midsole 130 and/or outsole 140 may comprise polyolefins, for example polyethylene (PE), polystyrene (PS) and/or polypropylene (PP).

The above-mentioned materials for sole 150 may be recycled materials, which could be for example reclaimed polymer material, e.g. reclaimed from an ocean, especially from maritime waste. Reclaimed polymer material could be any suitable plastic material, for example TPU, PEBA, PE, PS, PP etc. In some embodiments, more than 50%, or more than 90% reclaimed material may be used for midsole 130 and/or outsole 140.

In some embodiments, midsole 130 and/or outsole 140 may comprise a plurality of different materials (from different classes of materials or from the same class of materials with slightly different properties). In some embodiments, portions of sole 150 (e.g., midsole 130 and outsole 140) may comprise different materials to provide different characteristics to different portions of sole 150. In some embodiments, portions of sole 150 (e.g., midsole 130 and outsole 140) may comprise the same material, but with different material properties. In some embodiments, midsole 130 and outsole 140 may have different hardness characteristics. In some embodiments, the material density of midsole 130 and outsole 140 may be different. In some embodiments, the moduli of the materials used to make midsole 130 and outsole 140 may be different. As a non-limiting example, the material of outsole 140 may have a higher modulus than the material of midsole 130.

Sole 150 and portions thereof (e.g., midsole 130 and outsole 140) may be formed using an additive manufacturing process, including, but not limited to, selective laser sintering, selective laser melting, selective heat sintering, stereo lithography, fused deposition modeling etc., or 3D-printing in general. In some embodiments, midsole 130 and/or outsole 140 may be formed using an additive manufacturing process including a continuous liquid interface production process. For example, the continuous liquid interface production process described in U.S. Pat. No. 9,453,142, issued on Sep. 27, 2016, which is hereby incorporated in its entirety by reference thereto. In some embodiments, midsole 130 and outsole 140 may be formed as a single piece via an additive manufacturing process. In such embodiments, midsole 130 and outsole 140 may be a single integrally formed piece.

In some embodiments, outsole 140 may be formed by injection molding, blow molding, compression molding, or rotational molding. In such embodiments, midsole 130 and outsole 140 may be discrete components that are formed separately and attached. In some embodiments, midsole 130 may be attached to outsole 140 via, for example, but not limited to, adhesive bonding, stitching, welding, or a combination thereof. In some embodiments, midsole 130 may be attached to outsole 140 via an adhesive disposed between midsole 130 and outsole 140. Similarly, midsole 130 may be attached to upper 120 via, for example, but not limited to, adhesive bonding, stitching, welding, or a combination thereof.

FIGS. 3-7 show a midsole 300 manufactured by an additive manufacturing process according to some embodiments. Midsole 300 includes a forefoot end 302, a heel end 304, a medial side 306, a lateral side 308, a top side 310, and a bottom side 312. Midsole 300 may be defined, in whole or in part, by a three-dimensional mesh 320. In some embodiments, at least 80% or at least 90% of the volume of midsole 300 may be defined by three-dimensional mesh 320. In some embodiments, midsole 300 may include a rim 314 disposed around all or a portion of the perimeter of top side 310 of midsole 300. In some embodiments, rim 314 may be disposed around all or a portion of the perimeter of medial and lateral sides 306/308 of midsole 300. In embodiments including rim 314, rim 314 may be provide stability for the perimeter of midsole 300 and/or may facilitate attachment of midsole 300 to an upper (e.g., upper 120).

Three-dimensional mesh 320 includes a plurality of interconnected unit cells 322. The interconnected unit cells 322 include a plurality of struts 324 defining a three-dimensional shape of a respective unit cell 322. The interconnection (valence) between unit cells 322 may be defined by a plurality of nodes 326 at which one or more struts are connected. Nodes 326 may have a valence number defined by the number of struts 324 that are connected at that node 326. In some embodiments, nodes 326 may have a valence number in the range of 1 to 12.

Each unit cell 322 may have a base geometry defined by the struts 324 of the unit cell 322. As used herein "base geometry" means the base three-dimensional shape, connection, and arrangement of the struts 324 defining a unit cell 322. A base geometry is the three-dimensional shape, connection, and arrangement of unit cell struts 324 in an unwarped state (e.g., before a unit cell 322 is conformed to a warped cubic lattice). The base geometry of a unit cell 322 may be, but is not limited to, a dodecahedron (e.g., rhombic), a tetrahedron, an icosahedron, a cube, a cuboid, a prism, or a parallelepiped. In some embodiments, unit cells 322 may be constructed by assembling partial unit cells (e.g., partial unit cells 800 and 810). Unit cells 322 may be the same as or similar to unit cells 900 or 920 shown in FIGS. 9A and 9B.

Three-dimensional mesh 320 may define a volume of midsole 300. In other words, three-dimensional mesh 320 may define all, or at least a significant portion of (e.g., at least 90% or 80% of), the length, width, and height of midsole 300. In some embodiments, three-dimensional mesh 320 may include interconnected unit cells 322 organized in a warped lattice structure that defines a volume of midsole 300. In such embodiments, interconnected unit cells 322 may be constructed of partial unit cells (e.g., partial unit cells 800 and 810) assembled and arranged within lattice cells of warped lattice structure. In such embodiments, respective unit cells 322 may occupy a plurality of lattice cells in a warped lattice structure. In some embodiments, the warped lattice structure may be a warped cubic lattice structure. In some embodiments, in a warped cubic lattice structure, each unit cell 322 may be arranged in a lattice cell having a purely cubic or warped cubic shape. In some embodiments, in a warped cubic lattice structure, one or more partial unit cells forming unit cells 322 may be arranged in a lattice cell having a purely cubic or warped cubic shape. As discussed below in connection with FIGS. 13-15B, a warped lattice structure (e.g., a cubic warped lattice structure) is an invisible lattice structure used to arrange unit cells, or partial unit cells, and construct a three-dimensional mesh. In some embodiments, the warped lattice structure may be a warped tetrahedron lattice or a warped dodecahedron lattice in which unit cells, or partial unit cells, may be arranged.

A purely cubic shaped lattice cell is a three-dimensional lattice cell bound by six identical square faces joined along their edges. Three edges join at each corner to form vertexes of the purely cubic shaped lattice cell. A warped cubic shaped lattice cell is a three-dimensional lattice cell bound by six faces joined along their edges with at least one face being different from the others. Three edges join at each corner to form vertexes of the warped cubic shaped lattice. The side faces of a warped cubic shaped lattice cell need not have the same shape or area, and the side faces need not be squares.

Organizing unit cells 322 in a warped lattice structure may result in midsole 300 including only, or a significant portion of, complete unit cells. As used herein a "complete unit cell" means a unit cell that includes all the struts that define the unit cell's base geometry. A complete unit cell is not missing all or a portion of any strut that defines the unit cell's base geometry. In some embodiments, 90% or more of the unit cells 322 defining three-dimensional mesh 320 may be complete unit cells. Complete unit cells may facilitate manufacturing consistency and reproducibility because complete unit cells may behave more consistently than incomplete unit cells. Also, complete unit cells may be more durable than incomplete unit cells. Incomplete unit cells may be a by-product of post-formation processes such as cutting or trimming of unit cells.

Unit cells 322 may be arranged in a warped lattice structure including a plurality of warped lattice cells having different volumes and geometries. In some embodiments, a portion of a warped lattice structure may include unwrapped lattice cells (i.e. purely cubic lattice cells). In some embodiments, unit cells 322 may be arranged in a warped cubic lattice structure including a plurality of unwarped cubic lattice cells having different volumes and cubic geometries. The volume and geometry of the warped lattice cells, or unwarped lattice cells, may be based on a biometric data profile for an individual, or group of individuals. The warped lattice structure may define the plurality of nodes 326 at which one or more struts 324 are connected. The number and location of nodes 326, and the valence of nodes 326, may be based on a biometric data profile for an individual, or group of individuals.

In some embodiments, interconnected unit cells 322 may be arranged in a warped lattice structure that is warped in a longitudinal direction along the length of midsole 300 (i.e. between forefoot end 302 and heel end 304 of midsole 300). In some embodiments, interconnected unit cells 322 may be arranged in a warped lattice structure that is warped in a transverse direction along the width of midsole 300 (i.e., between medial side 306 and lateral side 308 of midsole 300). In some embodiments, interconnected unit cells 322 may be arranged in a warped lattice structure that is warped in a vertical direction along the height of midsole 300 (i.e., between top side 310 and bottom side 312 of midsole 300). In some embodiments, interconnected unit cells 322 may be arranged in a warped lattice structure that is warped in at least two of the longitudinal direction, the transverse direction, and the vertical direction. In some embodiments, interconnected unit cells 322 may be arranged in a warped lattice structure that is warped in the longitudinal direction, the transverse direction, and the vertical direction. A lattice structure that is warped in longitudinal, transverse, and/or vertical direction includes at least one lattice cell having a geometry warped in that direction (e.g., a side face warped in that direction).

In some embodiments, the valence number of nodes 326 in three-dimensional mesh 320 may vary. In some embodiments, the variation in the valence number of nodes may be based on a biometric data profile collected for an individual, or group of individuals. In some embodiments, the valence number of nodes 326 in three-dimensional mesh 320 may vary in a longitudinal direction along the length of midsole 300 between forefoot end 302 of midsole 300 and heel end 304 of midsole 300. In some embodiments, the valence number of nodes 326 may vary in a transverse direction along the width of midsole 300 between lateral side 308 of midsole 300 and medial side 306 of midsole 300. In some embodiments, the valence number of nodes 326 may vary in a vertical direction along the height of midsole 300 between top side 310 of midsole 300 and medial side 306 of midsole 300. The variation in the valence number of nodes 326 in the longitudinal, transverse, and/or vertical direction may be based on a biometric data profile collected for an individual, or group of individuals.

In some embodiments, the average value for the valence numbers of nodes 326 in forefoot portion 110 of midsole 300 may be greater than the average value for the valence numbers of nodes 326 in heel portion 114 of midsole 300. In such embodiments, forefoot portion 110 of midsole 300 may be stiffer than heel portion 114 and heel portion 114 of midsole 300 may provide a higher degree of cushioning. In some embodiments, the average value for the valence numbers of nodes 326 in forefoot portion 110 of midsole 300 may be less than the average value for the valence numbers of nodes 326 in heel portion 114 of midsole 300. In some embodiments, the average value for the valence numbers of nodes 326 in midfoot portion 112 of midsole 300 may be less than the average value for the valence numbers of nodes in forefoot portion 110 and heel portion 114 of midsole 300. In such embodiments, midfoot portion 112 of midsole 300 may provide a higher degree of cushioning than forefoot portion 110 and heel portion 114.

In some embodiments, the average value for the valence numbers of nodes 326 in forefoot portion 110 may be X, the average value for the valence numbers of nodes 326 in midfoot portion 112 may be Y, and the average value for the valence numbers of nodes 326 in heel portion 114 may be Z, where X, Y, and Z have a value in the range from 2 to 12. In some embodiments, X may be greater than Y and Y may be greater than Z. In such embodiments, X may be in the range from 5 to 12, Y may be in the range from 4 to 8, and Z may be in the range from 3 to 7. In some embodiments, Z may be greater than Y and Y may be greater than X. In such embodiments, X may be in the range from 3 to 7, Y may be in the range from 4 to 8, and Z may be in the range from 5 to 12. In some embodiments, Y may be less than Z and X. In such embodiments, X may be in the range from 3 to 12, Y may be in the range from 2 to 7, and Z may be in the range from 3 to 8.

In some embodiments, the size of unit cells 322 may vary in three-dimensional mesh 320. In some embodiments, the size of unit cells 322 may vary based a biometric data profile for an individual, or group of individuals. In some embodiments, the size of unit cells 322 may vary based on the volume of the lattice cell (e.g., warped cubic lattice cell) in which a unit cell 322 is positioned. In some embodiments, the volume of lattice cells may be based on a biometric data profile for an individual, or group of individuals.

In some embodiments, the size of unit cells 322 may vary in the longitudinal direction along the length of midsole 300 between forefoot end 302 of midsole 300 and heel end 304 of the midsole 300. In some embodiments, the average size of unit cells 322 may increase in the longitudinal direction along the length of midsole 300 from the forefoot end 302 of midsole to heel end 304 of midsole 300. In some embodiments, the average size of unit cells 322 positioned in forefoot portion 110 of midsole 300 may be less than the average size of unit cells 322 positioned in heel portion 114 of midsole 300. In such embodiments, forefoot portion 110 of midsole 300 may be stiffer than heel portion 114 and heel portion 114 of midsole 300 may provide a higher degree of cushioning.

In some embodiments, the size of the unit cells 322 may vary in a vertical direction between top side 310 of midsole 300 and bottom side 312 of midsole 300. In some embodiments, the average size of unit cells 322 may increase in the vertical direction from bottom side 312 of midsole 300 to top side 310 of midsole 300. In some embodiments, the size of unit cells 322 may vary in a transverse direction between medial side 306 of midsole 300 and lateral side 308 of midsole 300. Variations in the size of unit cells 322 in the longitudinal, transverse, and/or vertical direction may be based on a biometric data profile collected for an individual, or group of individuals.

In some embodiments, the thickness of struts 324 defining the unit cells 322 may vary in a vertical direction between top side 310 of midsole 300 and bottom side 312 of midsole 300. In some embodiments, the thickness of struts 324 defining unit cells 322 may decrease in the vertical direction from bottom side 312 of midsole 300 to top side 310 of midsole 300. In some embodiments, the thickness of struts 324 defining unit cells 322 may vary in a transverse direction between medial side 306 of midsole 300 and lateral side 308 of midsole 300. In some embodiments, the thickness of struts 324 defining unit cells 322 may vary in a longitudinal direction between forefoot end 302 of midsole 300 and heel end 304 of midsole 300. Variations in the thickness of struts 324 in the longitudinal, transverse, and/or vertical direction may be based on a biometric data profile collected for an individual, or group of individuals.

In some embodiments, the geometry of unit cells 322 may vary in three-dimensional mesh 320. In some embodiments, the geometry of unit cells 322 may vary based on a biometric data profile for an individual, or group of individuals. In some embodiments, the geometry of unit cells 322 may vary based on the geometry of the lattice cell (e.g., warped/unwarped cubic lattice cell) in which a unit cell 322 is positioned, which may be based on a biometric data profile for an individual, or group of individuals. In some embodiments, all unit cells 322 in three-dimensional mesh 320 may have the same base geometry that is unwarped or warped differently depending on the unwarped or warped geometry of the lattice cell in which a unit cell 322 is positioned.

Figure 5A:
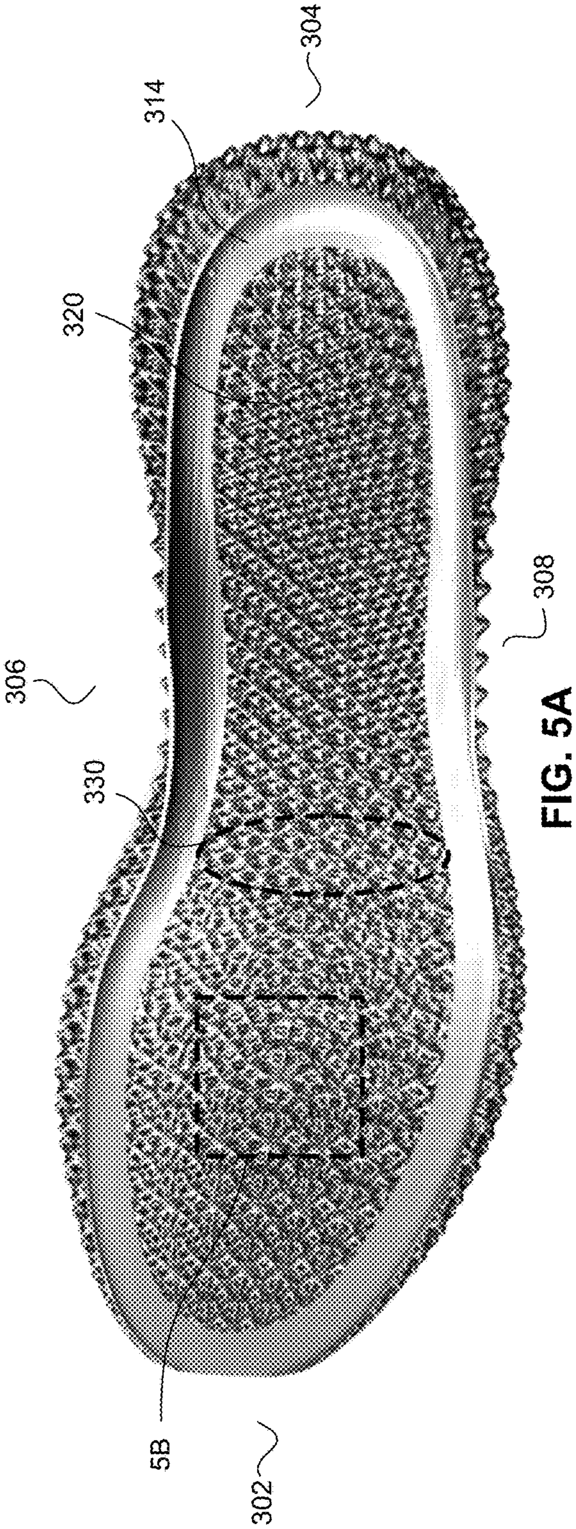
FIG. 5A is a top view of a midsole according to some embodiments.
Figure 5B:
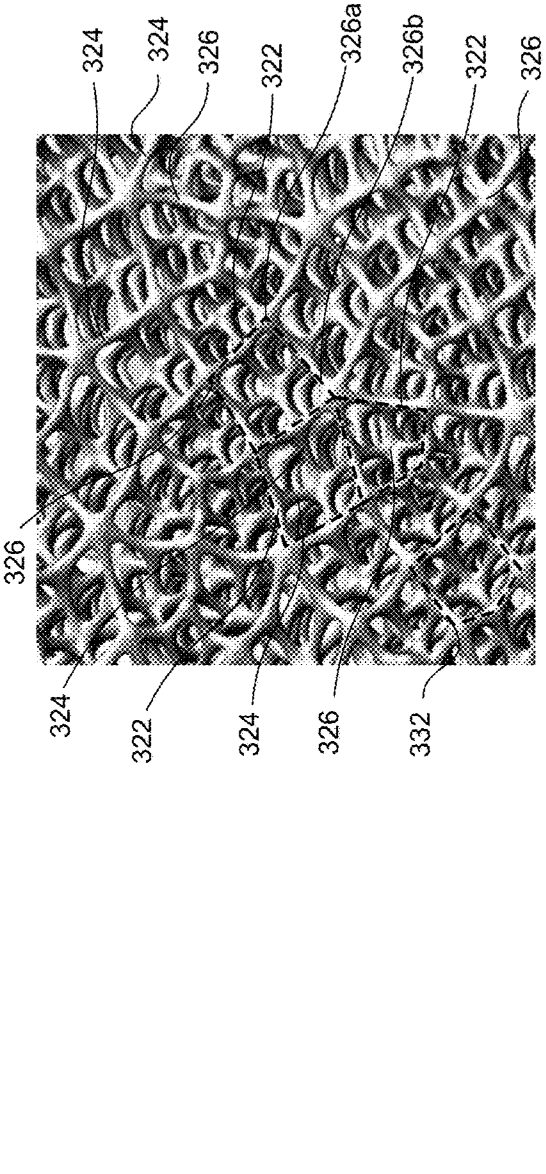
FIG. 5B is an enlarged view of a portion of FIG. 5A.

FIG. 5B shows interconnected unit cells 322 having the same base geometry arranged in a warped cubic lattice according to some embodiments. The labeled unit cells 322 have different sizes and warped geometry due to the different lattice cells in which they are positioned. Further, the valence of nodes 326 varies due to the different lattice cells in which the labeled unit cells 322 are positioned. FIG. 5B shows a first node 326*a* having a valence number of 4 and a second node 326*b* having a valence number of 5.

In some embodiments, unit cells 322 in three-dimensional mesh 320 may have different base geometries. In some embodiments, the geometry of unit cells 322, and their respective positions in three-dimensional mesh 320, may be based on a biometric data profile for an individual, or group of individuals. In some embodiments, three-dimensional mesh 320 may include a plurality of unit cells 322 having a first base geometry and a plurality of unit cells 322 having a second base geometry different from the first base geometry. In such embodiments, the location of the plurality of unit cells 322 having the first base geometry and the location of the plurality of unit cells 322 having the second base geometry may be based on a biometric data profile collected for an individual, or group of individuals.

In some embodiments, three-dimensional mesh 320 may include one or more transition zones 330 to provide for a gradual change in characteristics for midsole 300. In some embodiments, a transition zone 330 may include unit cells having the first base geometry interspersed with unit cells having the second base geometry. In such embodiments, a transition zone 330 may provide for gradual change in from a relatively stiff characteristic provided by a first base geometry to a relatively flexible characteristic provided by a second base geometry. In some embodiments, a transition zone 330 may include unit cells having a first size interspersed with unit cells having a second size to provide for gradual change in unit cell size, and thus a gradual change in characteristics of midsole 300. In some embodiments, a transition zone 330 may include unit cells having a first strut thickness interspersed with unit cells having a second strut thickness to provide for gradual change in characteristics of midsole 300. In some embodiments, the strut thickness of struts in a transition zone 330 may gradually change in a longitudinal direction, lateral direction, and/or vertical direction to provide for a gradual change in characteristics of midsole 300. A transition zone 330 may be located in forefoot portion 110, midfoot portion 112, and/or heel portion 114 of midsole 300.

In some embodiments, three-dimensional mesh 320 may include a plurality of unit cells 322 having two or more, three or more, four or more, or five or more different base geometries. In some embodiments, a plurality of unit cells 322 having a first base geometry may be located in forefoot portion 110 of midsole 300 and a plurality of unit cells 322 having a second base geometry may be located in a heel portion 114 of midsole 300. In such embodiments, the first base geometry and the second base geometry may be selected to provide desired characteristics for forefoot portion 110 and heel portion 114. For example, a first base geometry may be selected to provide a high degree of stiffness and/or propulsion in forefoot portion 110 and a second base geometry may be selected to provide a high degree of cushioning in heel portion 114.

In some embodiments, midfoot portion 112 of midsole 130 may include a plurality of unit cells 322 having the first base geometry and a plurality of unit cells 322 having the second base geometry. In some embodiments, midfoot portion 112 of midsole 300 may include a transition zone 330 including unit cells having the first base geometry interspersed with unit cells having the second base geometry. In some embodiments, midfoot portion 112 may include a plurality of unit cells 322 having a third base geometry different from the first base geometry and the second base geometry.

Figure 6:
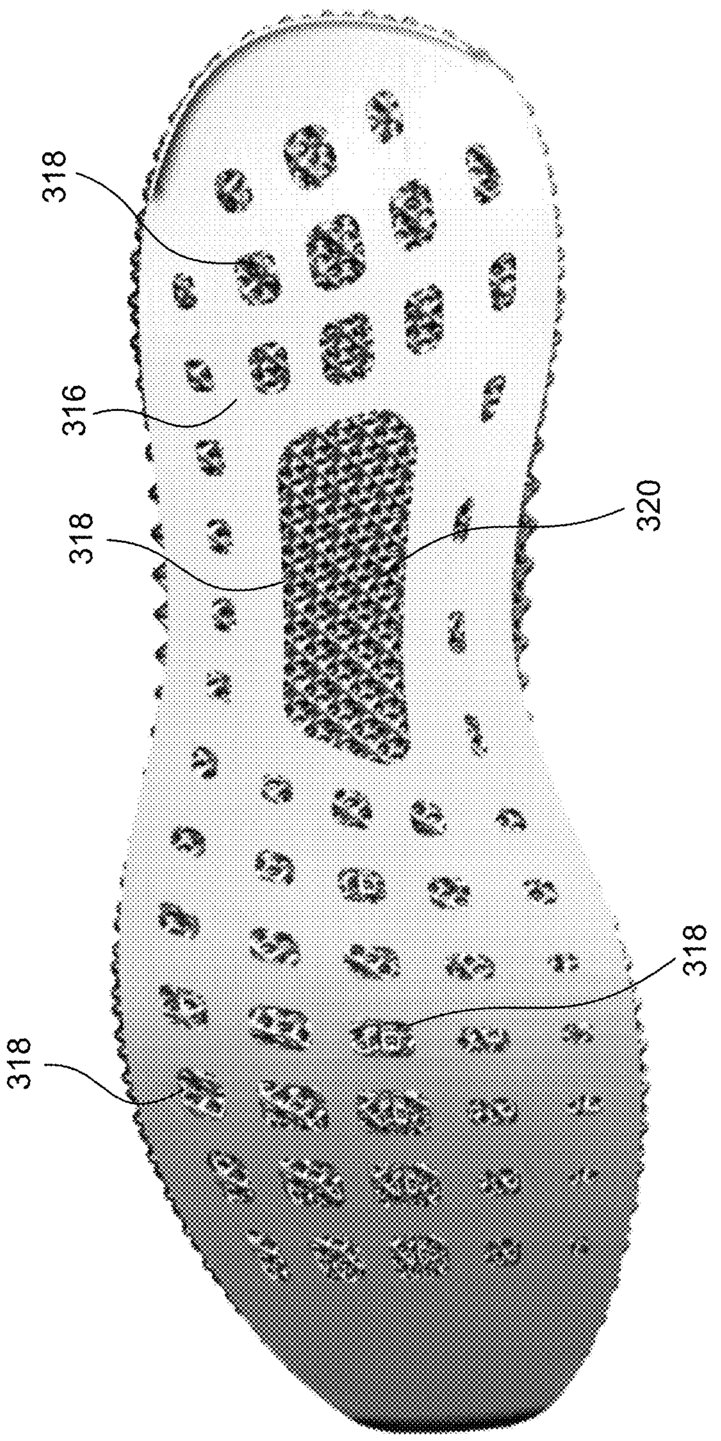
FIG. 6 is a bottom view of a midsole according to some embodiments.
Figure 7:
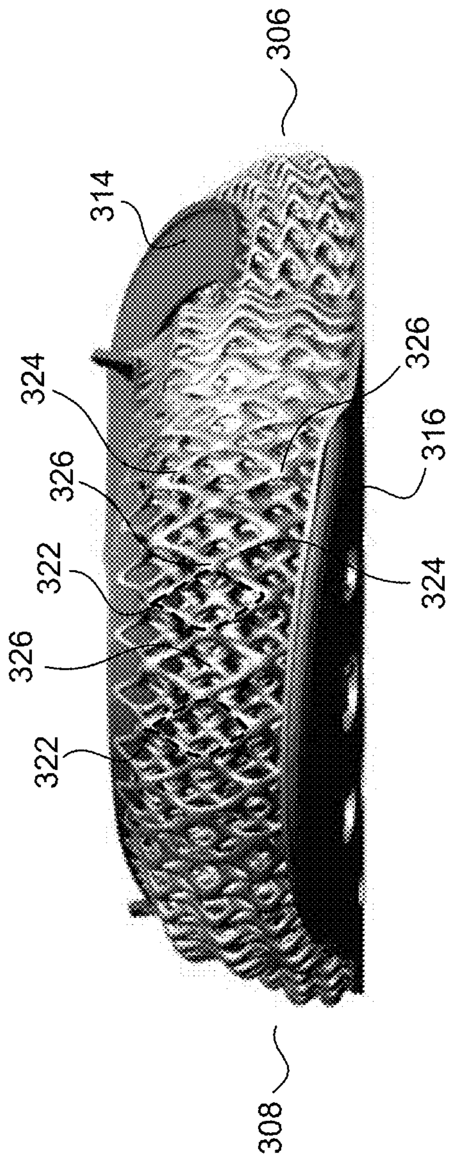
FIG. 7 is a rear view of a midsole according to some embodiments.

As shown for example in FIGS. 6 and 7, in some embodiments, an outsole 316 may be coupled to bottom side 312 of midsole 300. Outsole 316 may include or more or more openings 318. Openings 318 may provide desired ventilation and/or stiffness to different zones or portions of midsole 300. Openings 318 may vary in size and shape to provide various degrees of ventilation and/or stiffness to different zones or portions of midsole 300.

In some embodiments, midsole 300 and outsole 316 may be formed as a single piece via an additive manufacturing technique. In such embodiments, midsole 300 and outsole 316 may be a single integrally formed piece. In some embodiments, midsole 300 and outsole 316 may be manufactured separately attached, e.g., with an adhesive. In some embodiments, outsole 316 may include a plurality of protrusions the same as or similar to protrusions 142 to provide traction for midsole 300.

Figure 8B:
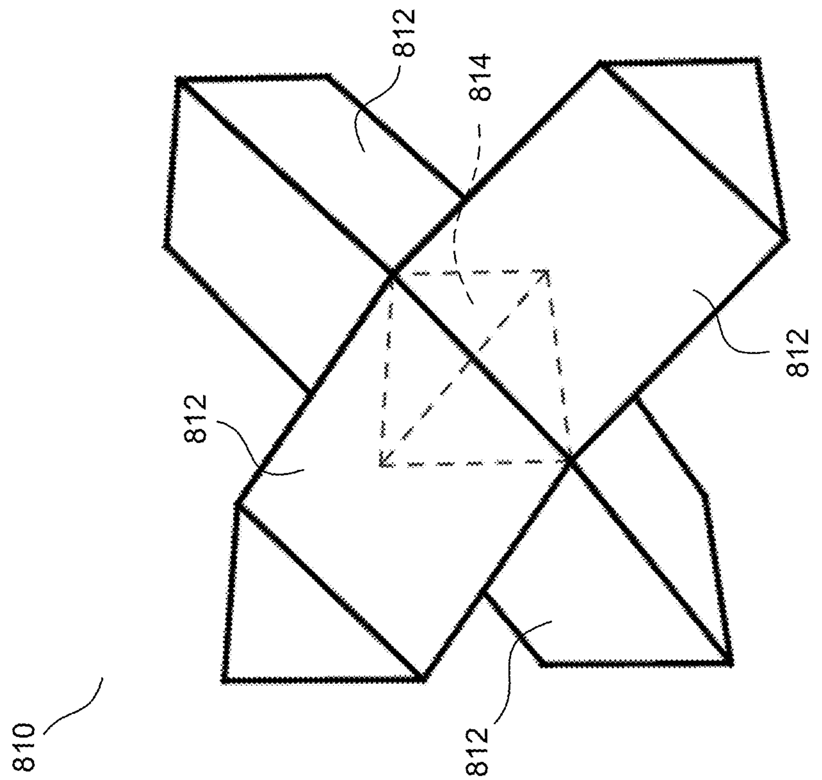
FIGS. 8A and 8B are partial unit cells according to some embodiments.
Figure 8A:
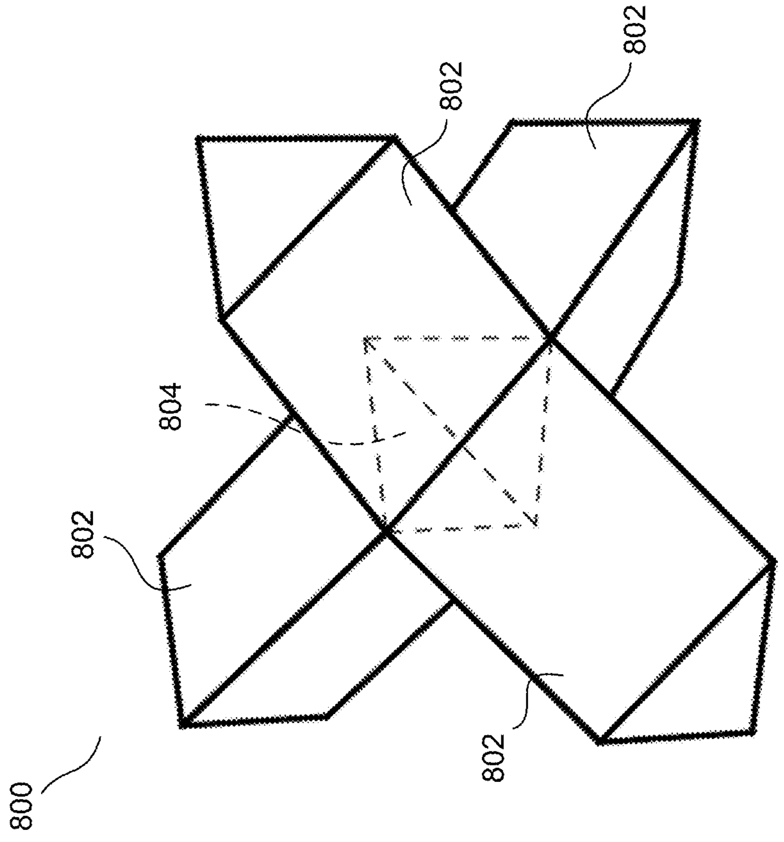

FIG. 8A shows a partial unit cell 800 according to some embodiments. Partial unit cell 800 includes a plurality of struts 802 connected at a node 804. In some embodiments, for example as shown in FIG. 8A, partial unit cell 800 may include four struts 802 connected at a node. In some embodiments, partial unit cell 800 may be a partial corner center lattice unit cell. In such embodiments, partial unit cell 800 may be used to build unit cells modeled after the chemical lattice structure of a face center cubic unit cell geometry of a solid crystalline material.

Struts 802 may include any suitable cross-sectional shape, such as but not limited to a triangular shape (e.g., as shown in FIG. 8A), a square shape, a hexagonal shape, a circular shape, or an oval shape. In some embodiments, struts 802 may be solid bar-like or tube-like elements. In some embodiments, struts 802 may be hollow bar-like or tube-like elements.

FIG. 8B shows a partial unit cell 810 according to some embodiments. Partial unit cell 810 may be a mirror image of partial unit cell 800. Similar to partial unit cell 800, partial unit cell 810 includes a plurality of struts 812 connected at a node 814. Partial unit cells 800 and 810 may be used to construct unit cells within a lattice structure (e.g., warped cubic lattice structure 1300). For example, FIGS. 9A and 9B show partial unit cells 914 and 934 (illustrated with cross-hatching for illustration purposes only) defining a portion of unit cells 900 and 920, respectively.

Figure 9A:
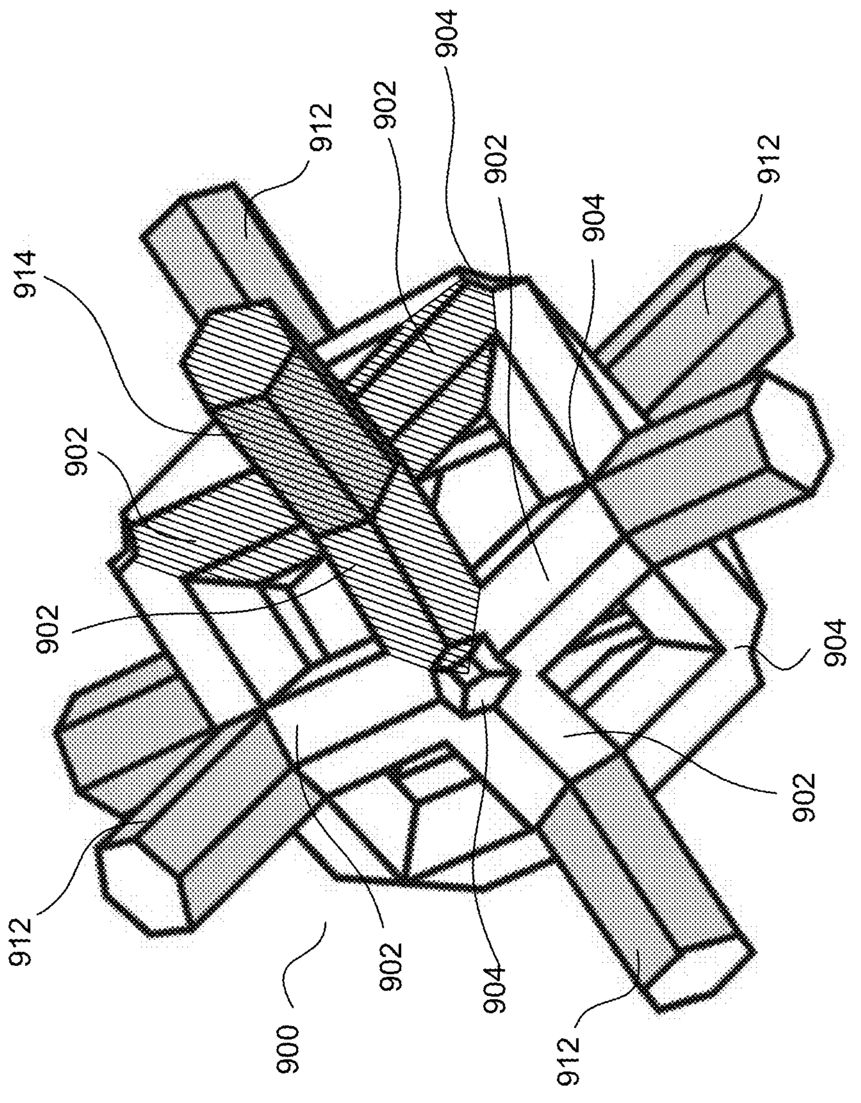
FIGS. 9A and 9B are unit cells according to some embodiments.

FIG. 9A shows a single unwarped unit cell 900 according to some embodiments. Unit cell 900 includes a plurality of struts 902 connected at nodes 904. In some embodiments, struts 902 may be solid bar-like or tube-like elements. In some embodiments, struts 902 may be hollow bar-like or tube-like elements. Struts 902 shown in FIG. 9A are arranged in a dodecahedron shape, however struts 902 may be arranged to form different shapes, such as but not limited to, a tetrahedron, an icosahedron, a cube, a cuboid, a prism, and a parallelepiped. Struts 912 from adjacent unit cells (shaded gray for illustration purposes) are shown connected to some nodes 904 of unit cell 900. The volume occupied by unit cell 900 may be for example 3 $mm^3$ to 30 $mm^3$, 5 $mm^3$ to 20 $mm^3$, 7 $mm^3$ to 15 $mm^3$, or 8 $mm^3$ to 12 $mm^3$.

Figure 9B:
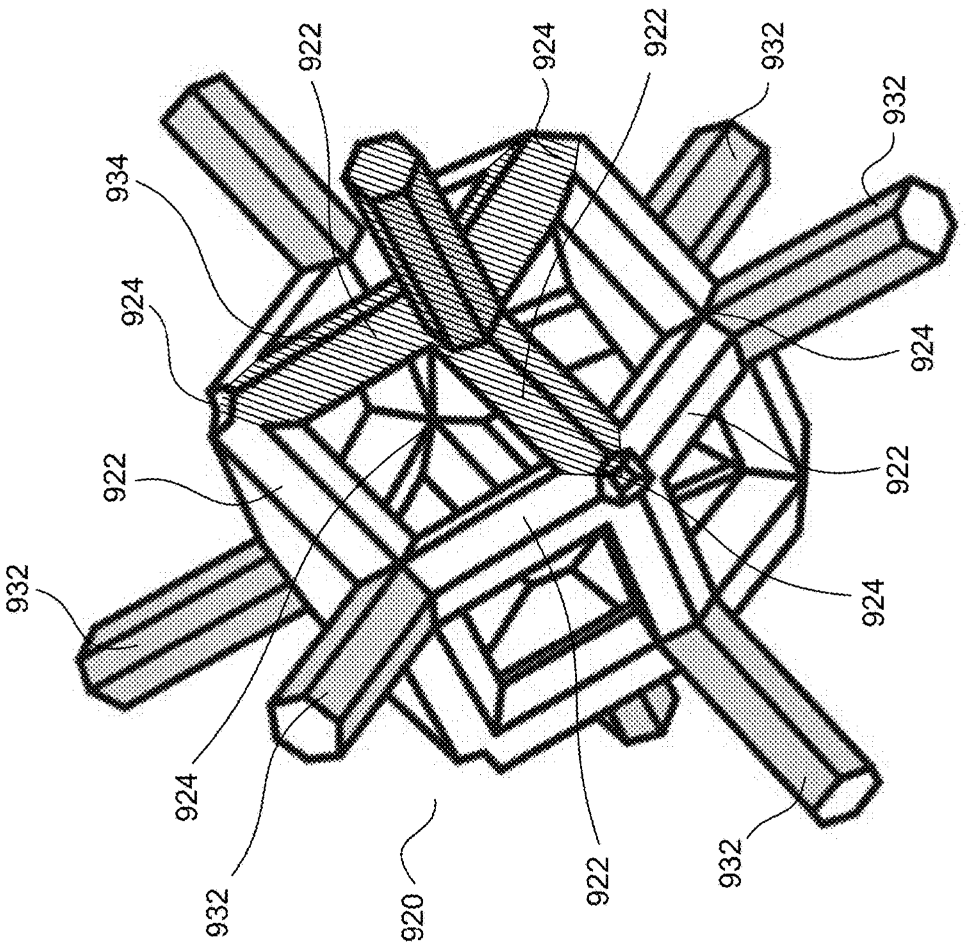

FIG. 9B shows another single unwarped unit cell 920 according to some embodiments. Similar to unit cell 900, unit cell 920 includes a plurality of struts 922 connected at nodes 924. However, the thickness of struts 922 may be less than struts 902. In some embodiments, the thickness of struts 922 may be reduced by approximately 75% to 85%. In such embodiments, the weight, stiffness and cushioning provided by unit cell 920 may be different from unit cell 900. Struts 932 from adjacent unit cells (shaded gray for illustration purposes) are shown connected to some nodes 924 of unit cell 920. As discussed herein, unit cells 900 and 920 may be arranged in a warped lattice to produce a three-dimensional mesh (e.g., three-dimensional mesh 320) for a midsole.

Figure 10:
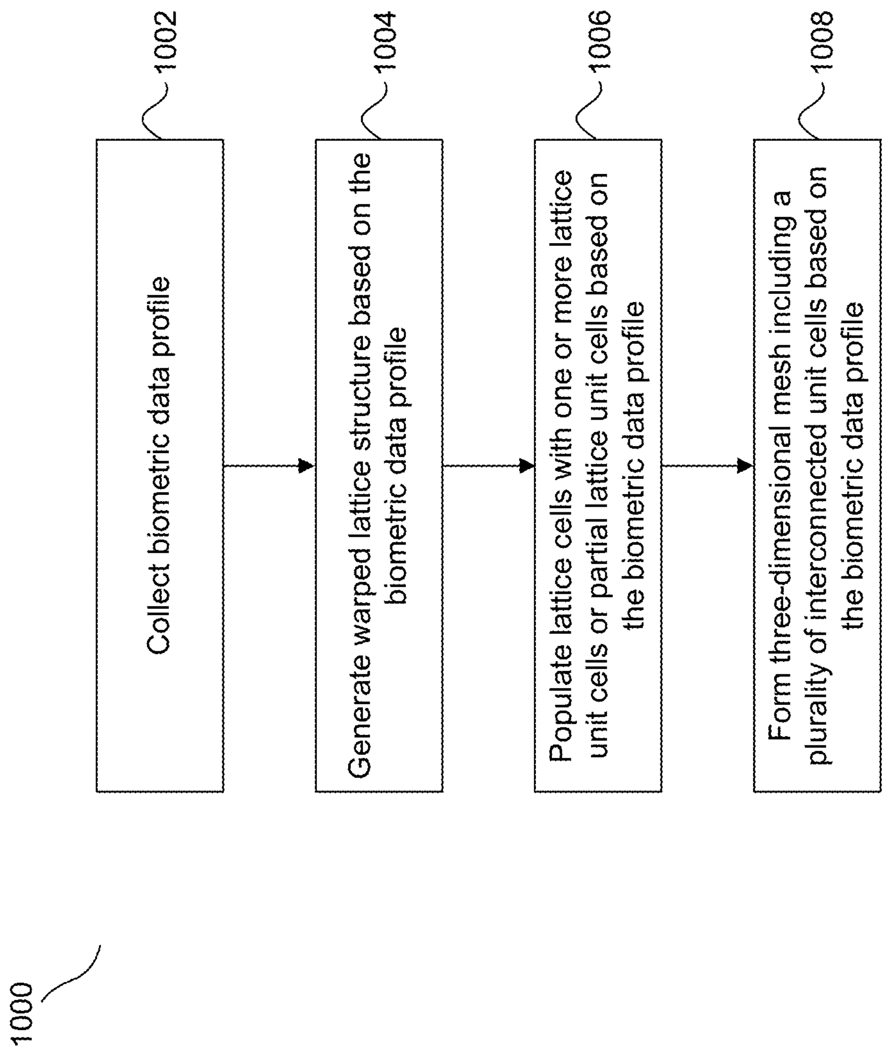
FIG. 10 is a method of making a three-dimensional mesh according to some embodiments.
Figure 11:
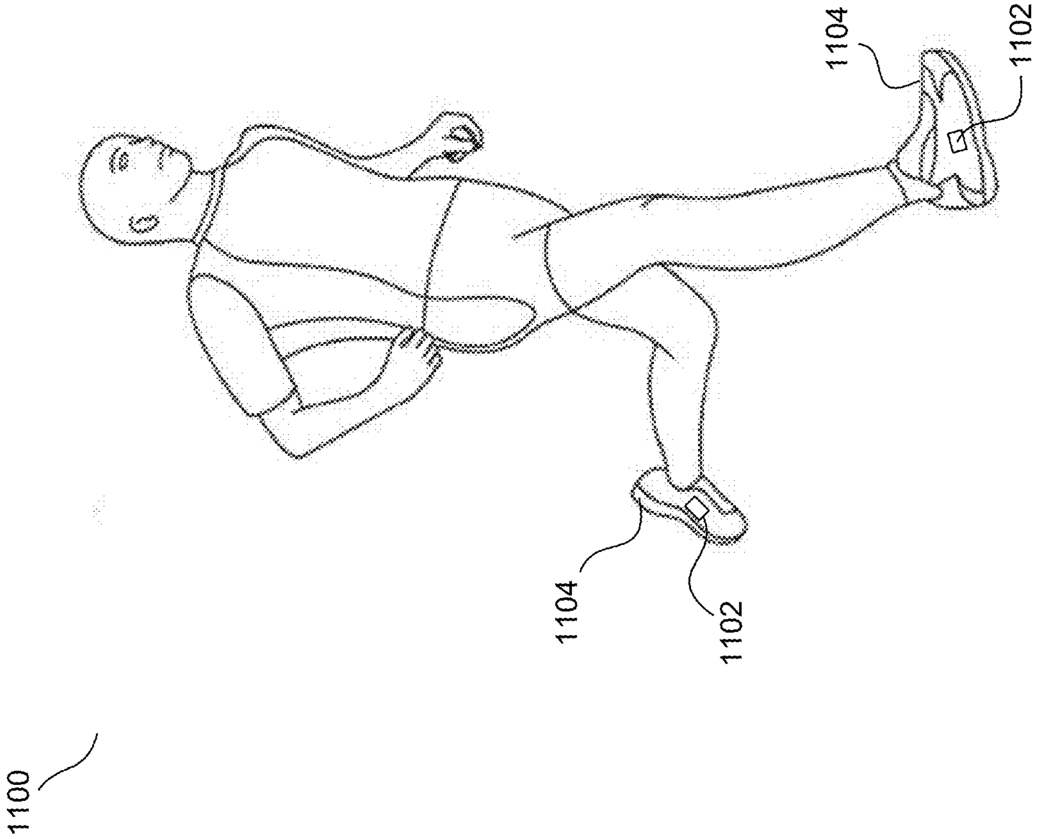
FIG. 11 is an illustration of an individual having sensor modules coupled to articles of footwear.

FIG. 10 shows a method 1000 of making a midsole (e.g. midsole 300) according to some embodiments. In step 1002 a biometric data profile for an individual (e.g., individual 1100 shown in FIG. 11) may be collected. In some embodiments, a biometric data profile may be collected using a physiological and personal characteristic collection and analysis system, such as a Run Genie® system. In some embodiments, the biometric data profile may be collected using the data collection and analysis system described in U.S. patent application Ser. No. 14/579,226, filed on Dec. 22, 2014 and published as US 2016/0180440, which is hereby incorporated by reference in its entirety by reference thereto.

The physiological characteristics collected may in step 1002 may include, but are not limited to, gait characteristics, such as foot strike type (e.g. heel, midfoot, forefoot, etc.), rate of pronation or supination, and degree of pronation and supination. In some embodiments, step 1002 may include receiving personal information about the individual before or after receiving physiological characteristics data about the individual. Personal information may include information such as their name, prior injury information, height, weight, gender, shoc size, an athletic goal, intended athletic environment or terrain, intended athletic activity duration, intended athletic activity frequency, intended athletic activity distance, quantitative or qualitative preferences about athletic equipment or footwear (such as level of cushion, preference of weight, materials and the like), and current athletic footwear.

In some embodiments, step 1002 may include receiving biometric data via a local wired or wireless connection. In some embodiments step 1002 may include monitoring individual 1100 in real time during an athletic activity, such as jogging.

Physiological characteristics may be collected using one or more sensor modules 1102. A sensor module 1102 may include one or more sensors, and may be physically coupled to an object (e.g., article of footwear 1104) during an everyday or athletic activity conducted by individual 1100. A sensor module 1102 may be used to monitor changes in the spatial orientation of an individual's body or a piece of the individual's athletic equipment or article of footwear in some embodiments. Sensor module 1102 may be used in combination with predetermined correlation data stored in a data structure to determine a correlation between body or equipment or article of footwear movement data and a characteristic such as a gait characteristic in some embodiments.

In some embodiments, a sensor module 1102 is placed and/or built into article of footwear 1104 to measure, for example, a runner's running form and gait cycle (e.g., sensor is placed on, removably attached to, or built into the heel, midsole, or toe of article of footwear 1104). Additional sensors/motion monitors can also be placed on the runner's knee and hip, for example, to obtain more information about the runner's running form.

Sensor module 1102 may include a plurality of sensors, including but not limited to, one or more motion sensors, such as acceleration sensors and magnetic field sensors, or angular momentum sensors. In some embodiments, sensor module 1102 may include one or more temperature sensors, a heart rate monitoring device, a pedometer, and/or an accelerometer-based monitoring device. Sensors of sensor module 1102 may be capable of measuring a variety of athletic performance parameters. The term "performance parameters" may include physical parameters and/or physiological parameters associated with the individual's 1100 athletic activity. Physical parameters measured may include, but are not limited to, time, distance, speed, pace, pedal count, wheel rotation count, rotation generally, stride count, stride length, airtime, stride rate, altitude, temperature, strain, impact force, jump force, force generally, and jump height. Physiological parameters measured may include, but are not limited to, heart rate, respiration rate, blood oxygen level, blood lactate level, blood flow, hydration level, calories burned, or body temperature.

An acceleration sensor may be adapted to measure the acceleration of the sensor module 1102. Accordingly, when the sensor module 1102 is physically coupled to an object (such as an individual's 1100 body, article of footwear 1104, or other a piece of athletic equipment), the acceleration sensor may be capable of measuring the acceleration of the object, including the acceleration due to the earth's gravitational field. In some embodiments, an acceleration sensor may include a tri-axial accelerometer that is capable of measuring acceleration in three orthogonal directions. In some embodiments one, two, three, or more separate accelerometers may be used.

A magnetic field sensor may be adapted to measure the strength and direction of magnetic fields in the vicinity of sensor module 1102. Accordingly, when sensor module 1102 is physically coupled to an object (such as an individual's 1100 body, article of footwear 1104, or other a piece of athletic equipment), a magnetic field sensor may be capable of measuring the strength and direction of magnetic fields in the vicinity of the object, including the earth's magnetic field. In some embodiments, a magnetic field sensor may be a vector magnetometer. In some embodiments, a magnetic field sensor may be a tri-axial magnetometer that is capable of measuring the magnitude and direction of a resultant magnetic vector for the total local magnetic field in three dimensions. In some embodiments one, two, three, or more separate magnetometers may be used.

In some embodiments, an acceleration sensor and a magnetic field sensor may be contained within a single accelerometer-magnetometer module bearing model number LSM303DLHC made by STMicroelectronics of Geneva, Switzerland.

An angular momentum sensor, which may be, for example, a gyroscope, may be adapted to measure the angular momentum or orientation of sensor module 1102. Accordingly, when the sensor module 1102 is physically coupled to an object (such as an individual's 1100 body, article of footwear 1104, or other athletic equipment), the angular momentum sensor may be capable of measuring the angular momentum or orientation of the object. In some embodiments, an angular momentum sensor may be a triaxial gyroscope that is capable of measuring angular rotation about three orthogonal axes. In some embodiments one, two, three, or more separate gyroscopes may be used. In some embodiments, angular momentum sensor may be used to calibrate measurements made by one or more of an acceleration sensor and a magnetic field sensor.

A heart rate sensor may be adapted to measure individual's 1100 heart rate. A heart rate sensor may be placed in contact with the individual's 1100 skin, such as the skin of the individual's chest, and secured with a strap. A heart rate sensor may be capable of reading the electrical activity the individual's 1100 heart.

A temperature sensor may be, for example, a thermometer, a thermistor, or a thermocouple that measures changes in the temperature. In some embodiments, a temperature sensor may primarily be used for calibration other sensors, such as, for example, an acceleration sensor and a magnetic field sensor.

In some embodiments, sensor module 1102 may include a position receiver, such as an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In some embodiments, a position receiver may be an antenna that is capable of communicating with local or remote base stations or radio transmission transceivers such that the location of sensor module 1102 may be determined using radio signal triangulation or other similar principles. In some embodiments, position receiver data may allow sensor module 1102 to detect information that may be used to measure and/or calculate position waypoints, time, location, distance traveled, speed, pace, or altitude.

Data collected by sensor module 1102 may classify individuals based on their running style, utilizing data analysis such as an anterior-posterior plot angle vs. time; medial-lateral plot angle vs. time; and the like. Calculations of these characteristic many be used to group individuals into different categories (groups), such as a heel striker, a mid foot striker, a forefoot striker, a pronator, supinator, a neutral individual, or some combination of characteristics. In some embodiments, gait analysis may utilize personal information of individual 1100, such a gender, shoe size, height, weight, running habits, and prior injuries.

In some embodiments, a regression analysis can be used to determine gait characteristics such as foot strike type, rate of pronation, degree of pronation, and the like based on acceleration data obtained from sensor module 1102. In some embodiments, the regression analysis can be used to determine gait characteristics such as foot strike type, rate of pronation, degree of pronation, and the like based on other data such as magnetometer data, angular momentum sensor data, or multiple types of data. In some embodiments, the analysis can include other user-input information such as prior injury information, an athletic goal, intended athletic environment or terrain, intended athletic duration, and current athletic footwear.

Athletic goals may be, for example, training for a race, to stay healthy, to lose weight, and training for sports. Other examples of athletic goals may include training for a race, or other sporting event, improving individual fitness, simply enjoy running, or the like. Frequency intervals may include for example about 1 to 2 times per week, about 3 to 4 times per week, about 5 to 7 times per week, or the individual doesn't know. Length intervals may include for example about less than about 5 miles per week, about 5 to 10 miles per week, about 10 to 20 miles per week, greater than about 20 miles per week, or the individual doesn't know. Examples of intended athletic terrain environments may include roads, track, treadmill, trail, gym, or particular athletic fields designed for a specific sport. Examples of athletic equipment preferences may include for example more cushioning, less weight, better fit, strength, durability, intended athletic activity range, balance, weight balance, more color choices, and the like.

Figure 12A:
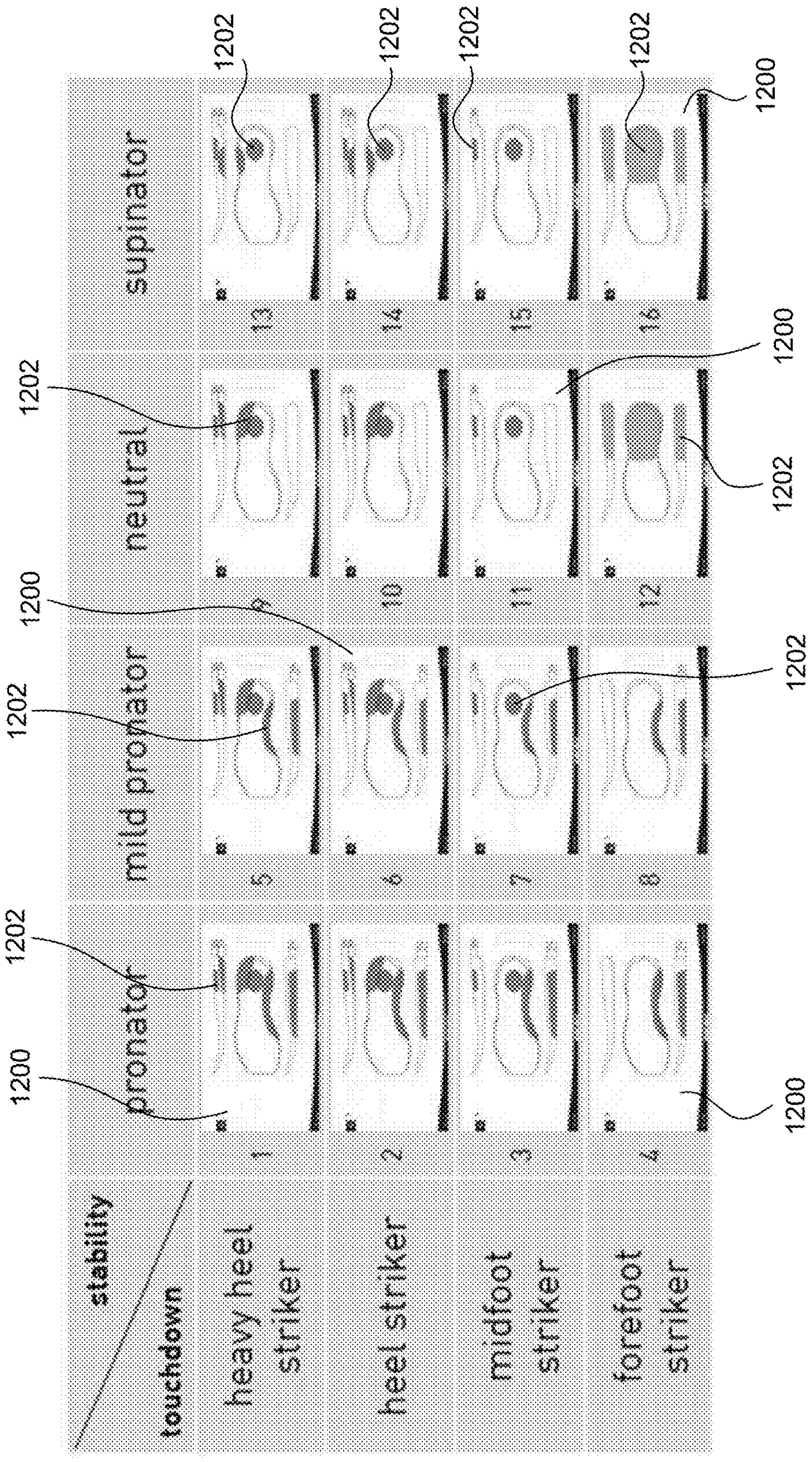
FIG. 12A is a collection of data maps according to some embodiments.

Information from sensor module(s) 1102 may be used to map areas of an individual's foot subject to different pressures or stresses. And information from sensor module(s) 1102 may be used to generate a biometric date profile map. For example, high stress areas may be associated with a heel portion, areas corresponding to the location of the ball of an individual's foot (i.e., at a position corresponding to a location near the anterior end of metatarsals), and a medial most portion of the individual's arch. Mild stress areas may be associated with a medial portion of the individual's arch and areas corresponding to the location of an individual's phalanges. And low stress areas may be associated with a lateral portion of the individual's arch. The size, location, and degree of stress areas for an individual will depend on, among other things, the anatomy of the individual's foot and the individual's gait. FIG. 12A illustrates sixteen different exemplary data profile maps that may be generated based on information from sensor module(s) 1102.

In some embodiments, collecting a biometric data profile in step 1002 may include obtaining previously collected and stored data for an individual. In some embodiments, collecting biometric data may include obtaining a standard biometric data profile for a group of individuals. For example, a standard profile for individuals having a certain shoe size, weight, height, arch shape, stability characteristic, and/or touchdown characteristic may be retrieved in step 1002.

FIG. 12A shows sixteen exemplary biometric data profile maps 1200. In some embodiments, biometric data profile maps 1200 may be one or more maps generated based on biometric profile collected for an individual. In some embodiments, biometric data profile maps 1200 may be standard biometric data profile maps for a group of individuals. For example, biometric data profile maps 1200 shown in FIG. 12A may be standard biometric profile maps for groups of individuals classified based on four stability characteristics (pronator, mild pronator, neutral, and supinator) and four touchdown characteristics (heavy heel striker, heel striker, midfoot striker, and forefoot striker), which results in sixteen classification groups. As used herein a "stability characteristic" refers to how an individual's foot rolls when it contacts the ground and a "touchdown characteristic" refers to how an individual's foot strikes the ground.

In embodiments including a biometric data profile map for an individual, map 1200 may include various stress areas 1202 associated with a particular individual. In embodiments including standard biometric data profile maps, maps 1200 may include various stress areas 1202 associated with different groups of individuals, based on information from sensor module(s) 1102. For example, as shown in FIG. 12A, certain combinations of stress areas 1202 may be associated with a heavy heel striker/pronator, a certain combination of stress areas 1202 may be associated with a heavy heel striker/mild pronator, a certain combination of stress areas 1202 may be associated with a heavy heel striker/neutral foot roll, and so on. Stress areas 1202 may be high stress areas, mild stress areas, or low stress areas typically associated groups of individual. And each of the sixteen classification groups may be associated with a particular combination of stress areas 1202. In some embodiments, data collected from sensor module(s) 1102 for a particular individual may be utilized to assign the individual a standard biometric data profile map best suited to that individual.

Figure 12B:
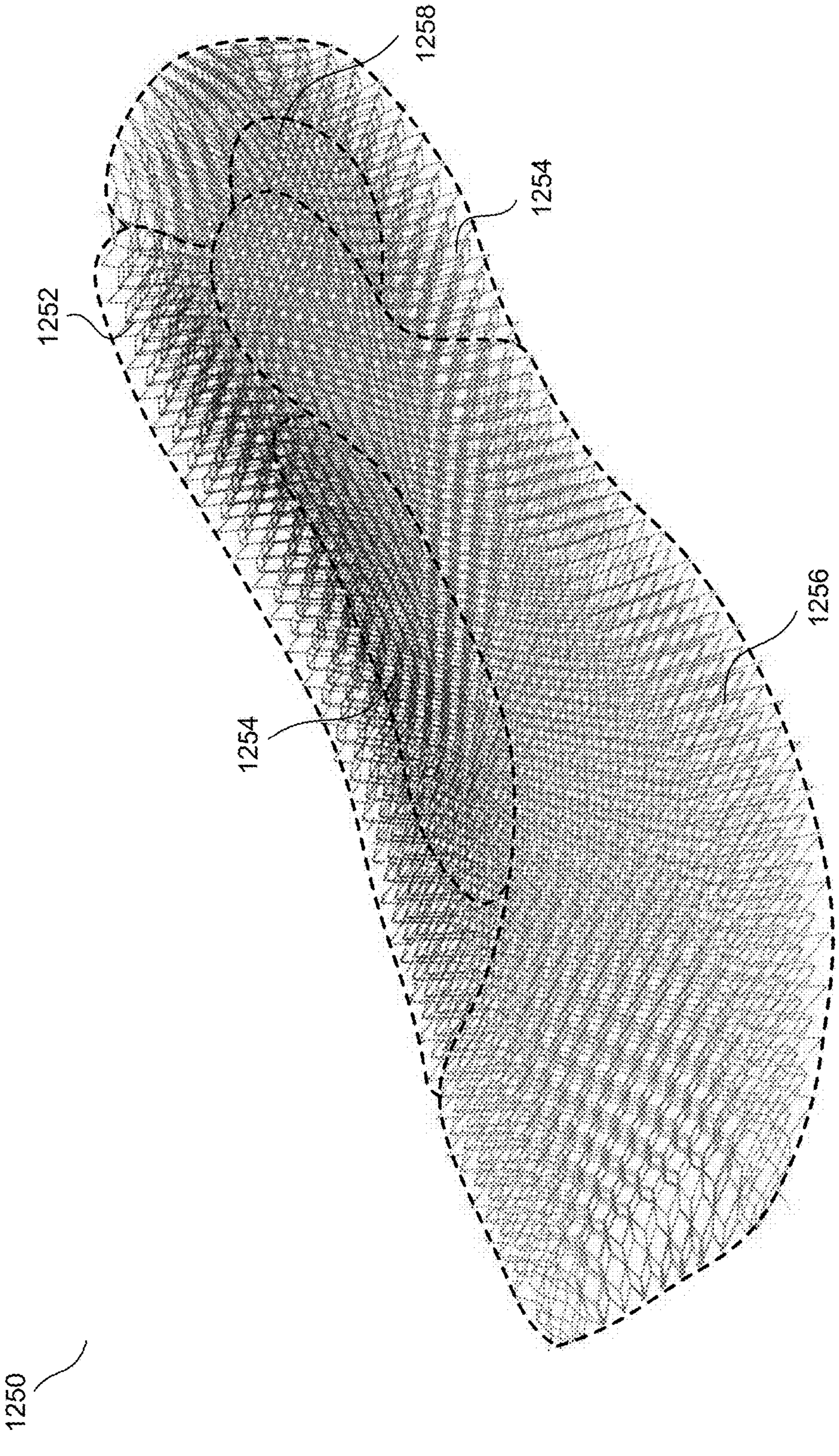
FIG. 12B is a lattice map according to some embodiments.
Figure 13:
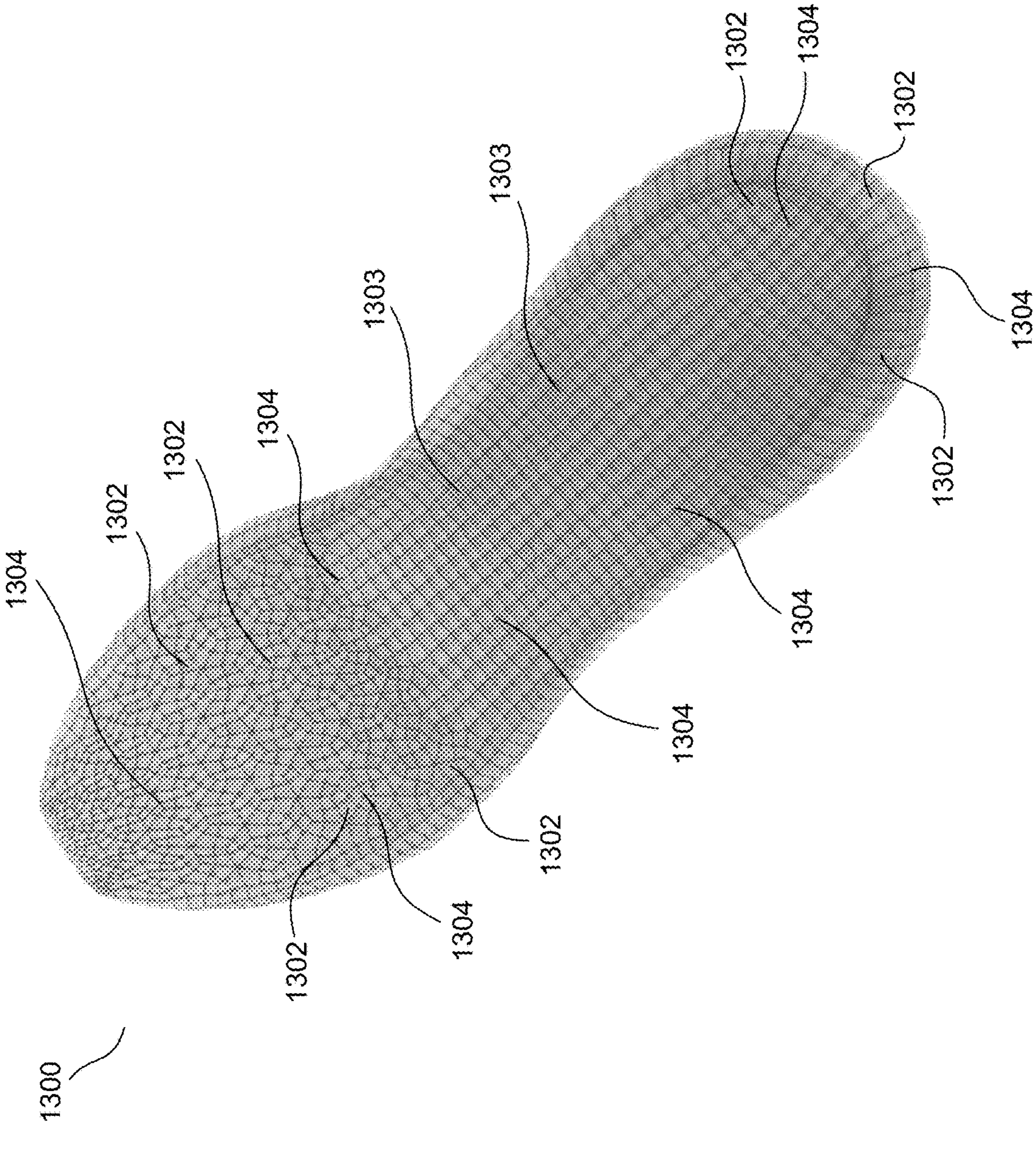
FIG. 13 is a warped cubic lattice structure according to some embodiments.
Figure 14:
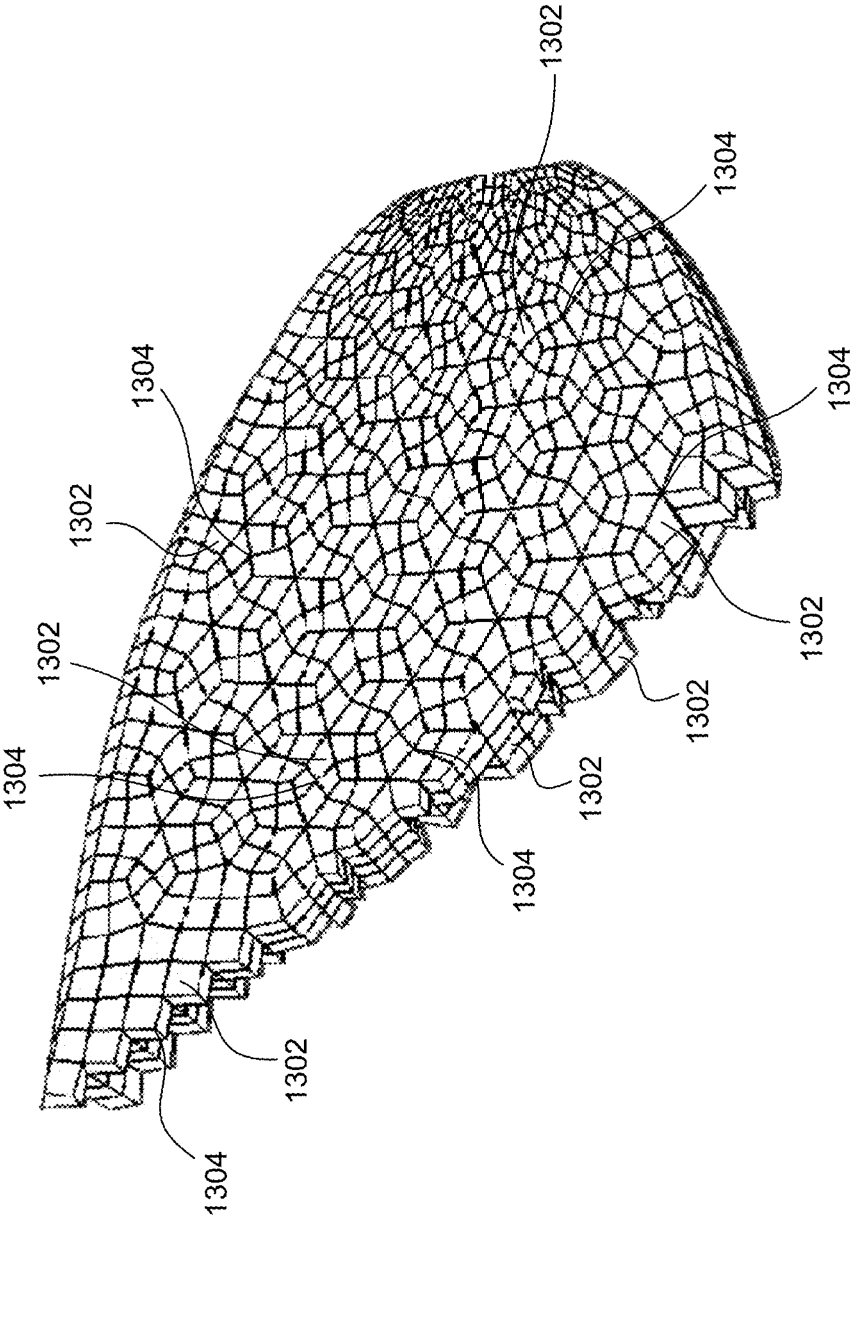
FIG. 14 is an enlarged sectional view of a portion of FIG. 13.
Figure 15A:
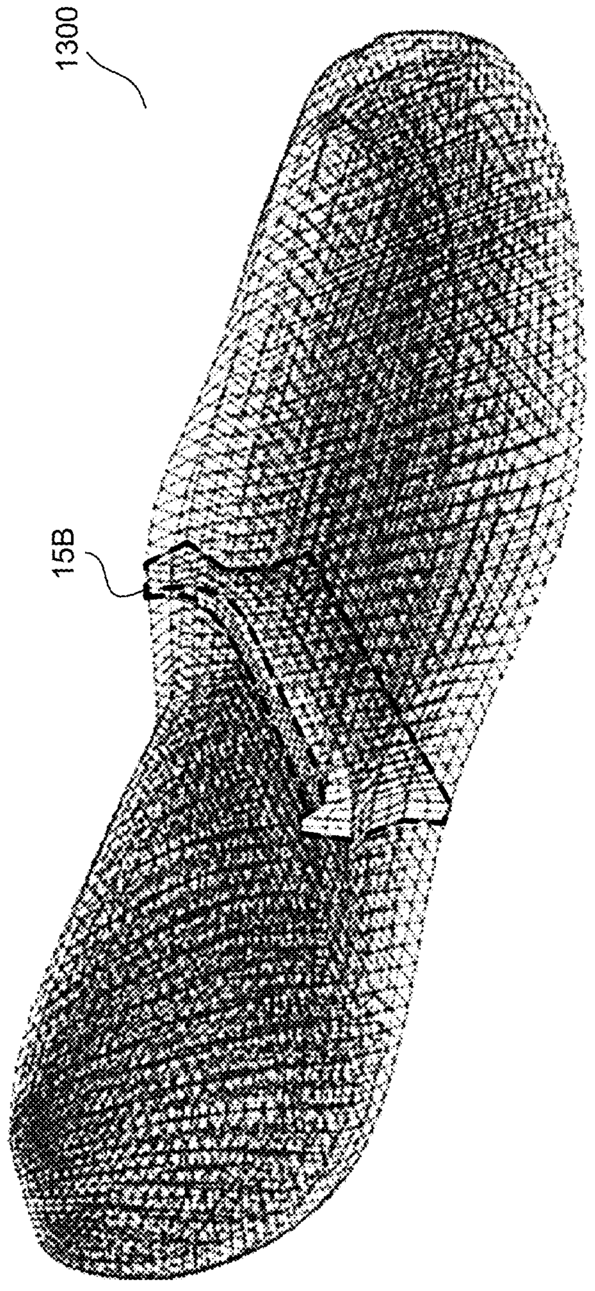
FIG. 15A is a perspective view a warped cubic lattice structure according to some embodiments.
Figure 15B:
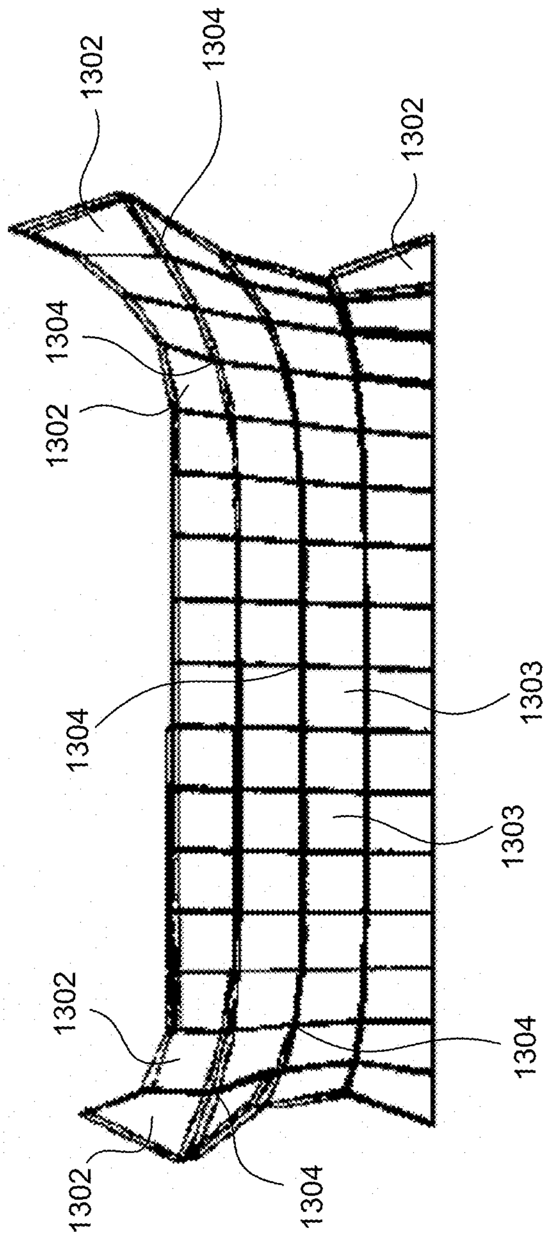
FIG. 15B is a cross-sectional segment taken from FIG. 15A.

A biometric data profile map 1200, along with another information collected about an individual (e.g., athletic goals), may be used to create a lattice map, for example the lattice map 1250 shown in FIG. 12B. Lattice map 1250 includes a plurality of different zones located, sized, and shaped to provide desired characteristics. For example, lattice map 1250 may include one or more of the following zones. A first zone type 1252 located in a medial side of lattice map 1250. A second zone type 1254 located in a lateral heel portion and medial arch portion of lattice map 1250. And a third zone type 1256 located in primarily a forefoot area and a lateral arch area of lattice map. And a fourth zone type 1258 located in a central heel area of lattice map 1250.

Different zones of lattice map 1250 (e.g., zones 1252/1254/1256/1258) may designate different geometries, interconnections, and/or arrangements of the unit cells at different locations within a three-dimensional mesh. For example, a zone may designate: (i) that unit cells within that zone have a particular strut stiffness (e.g., thickness), (ii) the number of unit cells per unit volume, (iii) the valence of nodes within that zone, (iv) the base geometry (ies) of unit cells within the zone, and/or (v) the material(s) used to make unit cells within the zone. In some embodiments, zones of lattice map 1250 may occupy a volume that extends from a bottom side of lattice map 1250 to a top side of lattice map 1250 (i.e., the entire height of lattice map). In some embodiments, zones of a lattice map 1250 may occupy a volume having a height less than the height of lattice map 1250. For example, a first zone may occupy a bottom half of a portion of lattice map 1250 and a second zone may occupy the top half of that portion of lattice map 1250. As another example, a first zone may occupy a middle third of a portion of lattice map 1250 and a second zone may occupy the top and bottom thirds of that portion of lattice map 1250 (i.e. all or a portion of first zone may be sandwiched between the second zone). In some embodiments, a zone may designate a transition zone, such as a transition zone including unit cells having a first geometry interspersed with unit cells having a second geometry.

Once a biometric data profile is collected in step 1002, a warped lattice structure may be generated based on the biometric data profile in step 1004. A warped lattice structure maybe generated using computer modeling program such, as but not limited to Grasshopper 3D and/or Rhinoceros 3D CAD software. FIGS. 13-15B show a warped cubic lattice structure 1300 according to some embodiments. Warped cubic lattice structure 1300 defines a volume of a three-dimensional mesh (e.g., three-dimensional mesh 320) and an invisible lattice in which unit cells of a three-dimensional mesh (e.g., unit cells 322 of three-dimensional mesh 320) are populated and tailored for an individual, or group of individuals.

In some embodiments, the volume of warped cubic lattice structure 1300 may be defined by a plurality of warped cubic lattice cells 1302 and a plurality of unwarped cubic lattice cells 1303. In some embodiments, the volume of warped cubic lattice structure 1300 may be defined by only warped cubic lattice cells 1302 (i.e., every cubic lattice cell in warped cubic lattice structure is warped). Nodes 1304 in warped cubic lattice structure 1300 are located at connection points of vertexes of one or more cubic lattice cells (warped or unwarped lattice cells). Nodes 1304 of warped cubic lattice structure 1300 may define the location of nodes in a three-dimensional mesh (e.g., nodes 326 in three-dimensional mesh 320). Warped cubic lattice cells 1302 may be warped in a longitudinal direction along the length of warped cubic lattice structure 1300, a transverse direction along the width of warped cubic lattice structure 1300, and/or in a vertical direction along the height of warped cubic lattice structure 1300. In some embodiments, the degree of warping for warped cubic lattice cells 1302 may decrease when moving from a forefoot portion of warped cubic lattice structure 1300 to a heel portion of warped cubic lattice structure 1300.

In some embodiments, warping cubic lattice cells increases the valence number of nodes 1304 in warped cubic lattice structure 1300. In such embodiments, warping the cubic lattice cells increases the number of lattice cells having vertexes connected at a node 1304. In some embodiments, warping cubic lattice cells increases the cubic lattice density in a warped cubic lattice structure 1300. Increasing the valence number and the cell density in zones/portions of warped cubic lattice structure 1300 may result in zones/portions of a three-dimensional mesh with a higher degree of stiffness. In some embodiments, as shown for example in FIGS. 13 and 14, a forefoot portion of warped cubic lattice structure 1300 may include more warped cubic lattice cells 1302 than a midfoot portion and heel portion. In such embodiments, the midfoot and heel portions of a resulting three-dimensional mesh may provide a higher degree of cushioning compared to the forefoot portion.

In some embodiments, a perimeter region of warped cubic lattice structure 1300 may be defined warped cubic lattice cells 1302 to provide support and stability for a perimeter zone of a three-dimensional mesh. As shown for example in FIGS. 15A and 15B, a perimeter zone of warped cubic lattice structure 1300 in a midfoot portion of warped cubic lattice structure 1300 may include a plurality of columns of warped cubic lattice cells 1302 disposed on opposite sides of a central zone including a plurality of unwarped cubic lattice cells 1303. In some embodiments, a heel portion of warped cubic lattice structure 1300 may include a cross section similar to the one shown in FIG. 15B. In some embodiments, a forefoot portion of warped cubic lattice structure 1300 may include a cross section similar to the one shown in FIG. 15B.

In some embodiments, the average volume of individual warped/unwarped cubic lattice cells 1302/1303 located in a forefoot portion of warped cubic lattice structure 1300 may be less than the average volume of individual warped/unwarped cubic lattice cells 1302/1303 located in a heel portion of warped cubic lattice structure. In such embodiments, individual warped/unwarped cubic lattice cells 1302/1303 located in the forefoot portion may have a smaller vertical dimension (i.e., may be thinner) than warped/unwarped cubic lattice cells 1302/1303 located in the heel portion. Smaller individual warped/unwarped cubic lattice cells 1302/1303 located in a forefoot portion of warped cubic lattice structure 1300 may result in a three-dimensional mesh having a forefoot portion that is stiffer and provides a higher degree of propulsion compared to a heel portion of the three-dimensional mesh.

The volume of warped cubic lattice structure 1300 may be customized to the shape of an individual's foot, or group of individuals' feet. The location and number of warped or unwarped cubic lattice cells 1302/1303 may be determined based on the biometric data profile collected in step 1002. For example, warped cubic lattice cells 1302 may have different volumes and cubic geometries to accommodate the shape of an individual's foot, or a group of individuals' feet. The volume and cubic geometries of warped cubic lattice cells may be based on the biometric data profile collected in step 1002. And the volumes and cubic geometries of warped cubic lattice cells may dictate the volumetric characteristics of warped cubic lattice structure 1300.

For example, the volume of individual warped cubic lattice cells 1302 located in a midfoot portion of warped cubic lattice structure 1300 may be larger for an individual having a relatively large midfoot arch compared to an individual having a relatively small midfoot arch (e.g., a flat-footed individual). As another example, the volume of individual warped cubic lattice cells 1302 located in a forefoot portion of warped cubic lattice structure 1300 may be larger for a forefoot striker compared to a heel striker. As another example, the volume of individual warped cubic lattice cells 1302 located in a forefoot portion of warped cubic lattice structure 1300 may be smaller for a sprinter compared to a casual jogger. In such embodiments, smaller volume warped cubic lattice cells 1302 may result in smaller unit cells for a forefoot portion of a three-dimensional mesh, which may provide increased propulsion for a sprinter. And the larger warped cubic lattice cells 1302 in the forefoot portion for the casual jogger may provide a higher degree of cushioning for the jogger, which may increase comfort.

In some embodiments, unwarped cubic lattice cells 1303 may have different volumes. As a non-limiting example, the volume of unwarped cubic lattice cells 1303 in a heel portion of warped cubic lattice structure 1300 may be larger for a heel striker compared to a forefoot striker. As another example, the volume of unwarped cubic lattice cells 1303 in a heel portion of warped cubic lattice structure 1300 may be smaller for a sprinter compared to a casual jogger. In such embodiments, smaller volume unwarped lattice cells 1303 may result in smaller unit cells for a heel portion of a three-dimensional mesh, which may reduce the weight of a midsole for the sprinter.

In some embodiments, the relative amount of warped and unwarped cubic lattice cells may be tailored for an individual, or group of individuals. For example, a larger percentage of lattice cells located at a perimeter of warped cubic lattice structure 1300 may be warped unit cells for a narrow-footed individual compared to the percentage for a wide-footed individual. In such embodiments, the added warped lattice cells may serve conform a three-dimensional mesh the perimeter of an individual's foot and thus provide desired support and stability for perimeter portions of the foot. As another example, a larger percentage of lattice cells located at a perimeter of warped cubic lattice structure 1300 for a football player may be warped unit cells compared to the percentage for a casual jogger. In such embodiments, the added warped lattice cells may serve to provide a higher degree of perimeter support and stability for the football player to help avoid injury to the individual's foot, such as spraining his or her ankle As shown for example in FIGS. 14 and 15B, warped and unwarped cubic lattice cells 1302/1302 may be arranged in layers. The number of layers, the volume, and the cubic geometry of the lattice cells may be customized to the shape an individual's foot, or group of individual's feet. In some embodiments, the number of layers of lattice cells 1302/1303 may be smaller in a forefoot portion of warped cubic lattice structure 1300 than in a midfoot and/or a heel portion of warped cubic lattice structure 1300. For example, a forefoot portion of warped cubic lattice structure 1300 may include three layers and a midfoot portion and a heel portion of warped cubic lattice structure 1300 may include four layers of lattice cells. In some embodiments, the number of layers of lattice cells 1302/1303 may be the same in the forefoot, midfoot, and heel portions of warped cubic lattice structure 1300.

In some embodiments, generating a warped cubic lattice structure in step 1004 may include obtaining a previously generated warped cubic lattice structure for an individual. In some embodiments, generating a warped cubic lattice structure may include obtaining a standard warped cubic lattice structure for a group of individuals. For example, a standard warped cubic lattice structure for individuals having a certain shoe size, weight, height, stability characteristic, arch shape, and/or touchdown characteristic may be retrieved in step 1004.

In some embodiments, the generation of a warped cubic lattice in step 1004 may be based on a lattice map (e.g., lattice map 1250). In such embodiments, zones of a lattice map may influence the volume, size, and location of warped and unwarped cells within a warped cubic lattice. Customizing a warped cubic lattice structure as discussed herein may facilitate manufacturing consistency and reproducibility by reducing or eliminating incomplete unit cells in a midsole. Customizing a warped cubic lattice structure may result in only complete unit cells being located in a three-dimensional mesh because the warped/unwarped cells define the full volume needed to manufacture a midsole for an individual, or group of individuals. And thus reduce or eliminate post-formation processing steps, such as cutting or trimming, needed to produce a midsole with the desired volumetric characteristics.

Additionally, customizing a warped a lattice structure may help equally distribute loads (e.g., pressures, stress, and stains) across all unit cells populated into a warped lattice structure like warped cubic lattice structure 1300. Equally distributing loads may help provide desired cushioning, support, stability, ride, and/or propulsion characteristics for a midsole. Also, equally distributing loads may be prevent uneven wear across a midsole, which may maximize the lifetime of a midsole.

Figure 16:
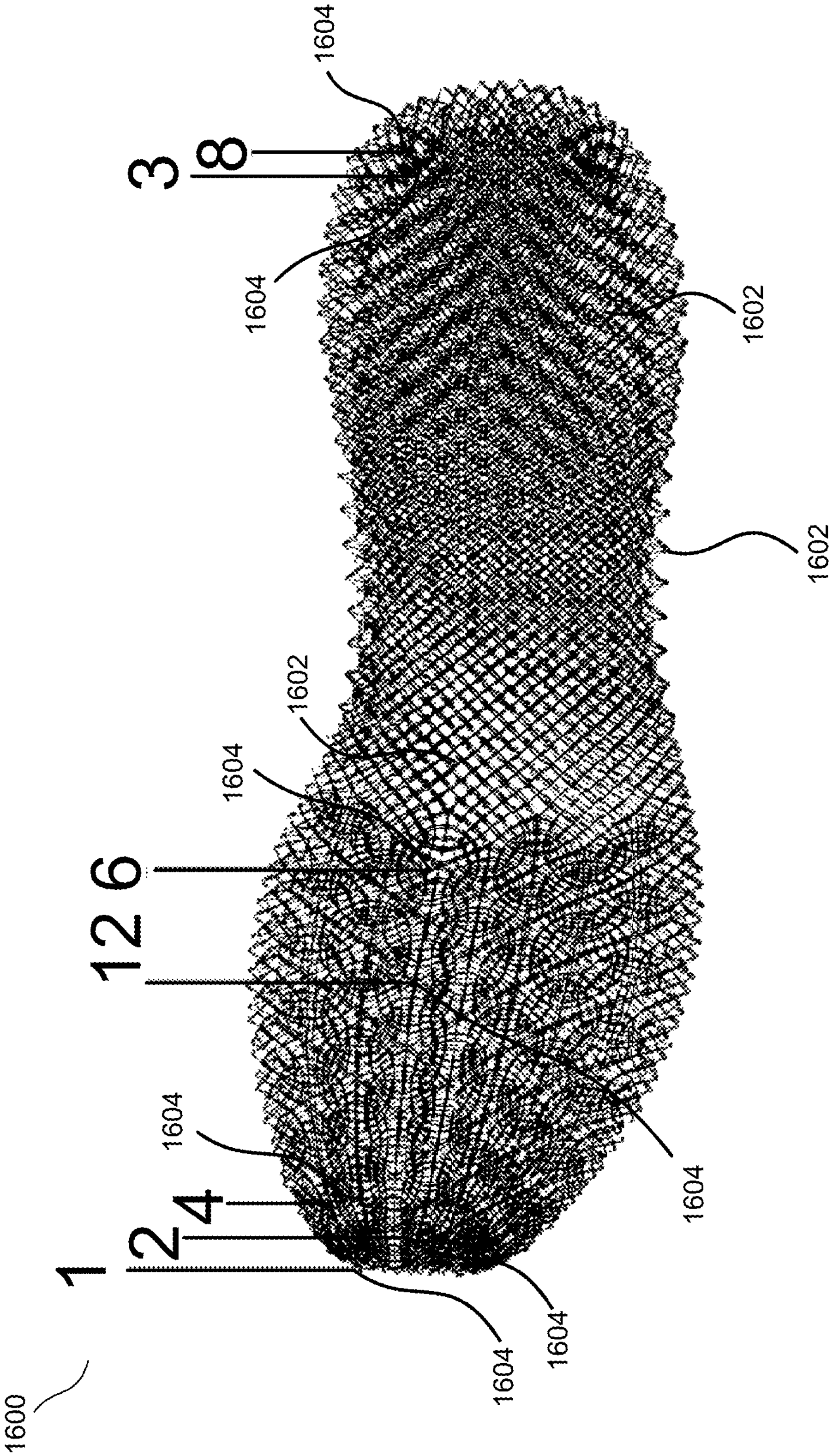
FIG. 16 is a cell lattice according to some embodiments.

After a warped lattice structure is created in step 1004, lattice unit cells may be populated into the warped lattice structure in step 1006. Population of lattice unit cells may be based on the biometric data profile collected in step 1002. FIG. 16 shows a cell lattice 1600 with lattice unit cells 1602 populated into a warped cubic lattice structure according to some embodiments. In some embodiments, the warped cubic lattice structure may be warped cubic lattice structure 1300. For purposes of illustration, the warped cubic lattice structure in which lattice unit cells 1602 are populated is not shown in FIG. 16.

In some embodiments, partial lattice unit cells may be populated into cubic lattice cells (e.g., warped and unwarped cubic lattice cells 1302/1303) to construct lattice unit cells 1602. For example, partial lattice unit cells having a geometry the same as or similar to partial unit cells 800 and 810 may be populated into cubic lattice cells to construct lattice unit cells 1602. In such embodiments, respective lattice unit cells 1602 may occupy a plurality of cubic lattice cells. In some embodiments, entire lattice unit cells 1602 may be populated into cubic lattice cells. Partial lattice unit cells or lattice unit cells may be populated into a warped lattice structure using a computer modeling program such as, but not limited to, Grasshopper 3D.

Populating partial lattice unit cells into lattice cells of warped lattice structure may increase the ability to customize a midsole for an individual, or group of individuals, by increasing the level of control in making a midsole. Since partial lattice unit cells are smaller than complete lattice unit cells, strut stiffness (e.g., thickness), the number of unit cells per unit volume, the valence of nodes, the geometry (ies) of unit cells, and/or the material(s) used to make a midsole may be more precisely controlled.

The cell lattice 1600 created in step 1006 will define the location unit cells, struts, and nodes in a three-dimensional mesh (e.g., unit cells 322, struts 324, and nodes 326 in three-dimensional mesh 320). The location of at least a portion of nodes 1604 in cell lattice 1600 may correspond to the location of nodes 1304 in warped cubic lattice structure 1300. In this manner, the base geometry of lattice unit cells 1602 may be warped based on warped cubic lattice structure 1300. In some embodiments, the valence number of at least a portion of nodes 1604 of lattice unit cells 1602 may correspond to the valence number of nodes 1304 in warped cubic lattice structure 1300. FIG. 16 shows the valence number for six different nodes 1604 within cell lattice 1600. In some embodiments, the creation of cell lattice 1600 in step 1006 may be based on a lattice map (e.g., lattice map 1250). Since cell lattice 1600 corresponds to the location of unit cells in a three-dimensional mesh, the size, volume, location, and interconnection between lattice unit cells 1602 influences: (i) the number of unit cells per unit volume (i.e., the density of unit cells), (ii) the degree of interconnection between unit cells (referred to herein as "valence") and (iii) the base geometry of the unit cells.

In some embodiments, more than one partial lattice unit cell, or lattice unit cell 1602, may be populated into a single warped or unwarped cubic lattice cell 1302/1303. In such embodiments, those cell sites will have an increased unit cell density to provide, for example, a higher degree of stiffness and/or stability for portions or zones of a three-dimensional mesh. In some embodiments, two partial lattice unit cells, or two lattice unit cells 1602, may be populated into a single warped or unwarped cubic lattice cell 1302/1303. In such embodiments, the two partial lattice unit cells, or the two lattice unit cells 1602, may be mirror images of each other. In some embodiments, more than two partial lattice unit cells or, more than two lattice unit cells 1602, may be populated into a single warped or unwarped cubic lattice cell 1302/1303.

In some embodiments, creating a cell lattice in step 1006 may include obtaining a previously generated cell lattice for an individual. In some embodiments, creating a cell lattice may include obtaining a standard cell lattice for a group of individuals. For example, a standard cell lattice for an individual having a certain shoe size, weight, height, stability characteristic, arch shape, and/or touchdown characteristic may be retrieved in step 1006.

In step 1008, a three-dimensional mesh (e.g., three-dimensional meshes 300, 1700, 1800, 1900, or 2000) may be formed based on the cell lattice 1600 created in step 1006. Characteristics of three-dimensional mesh formed in step 1008 may be based on the biometric data profile collected in step 1002. In step 1008, the lines of lattice unit cells 1602 are transformed into struts of a three-dimensional mesh. In this manner, the stiffness (including for example compressive strength, shear strength and/or bending strength and/or torsional stiffness) of struts defining interconnected unit cells may tailored based on a biometric data profile. The stiffness of struts may be tailored by at least one of: adjusting the thickness of struts, adjusting the thickness of the nodes where one or more struts are connected, and adjusting the material of struts. In some embodiments, the transformation of lattice unit cells 1602 to struts in step 1008 may be based on a lattice map (e.g., lattice map 1250).

In some embodiments, additional components of a midsole, or sole, may be formed in step 1008. For example, a rim (e.g., rim 314) or an outsole (e.g., outsole 140) may be formed in step 1008. Three-dimensional mesh and any other components formed in step 1008 may be formed using an additive manufacturing process, such as but not limited to, a continuous liquid interface production process, selective laser sintering, selective laser melting, selective heat sintering, stereo lithography, fused deposition modeling, or 3D-printing in general. FIGS. 17A-20E shoe various exemplary three-dimensional meshes that may be produced with method 1000.

Figure 17A:
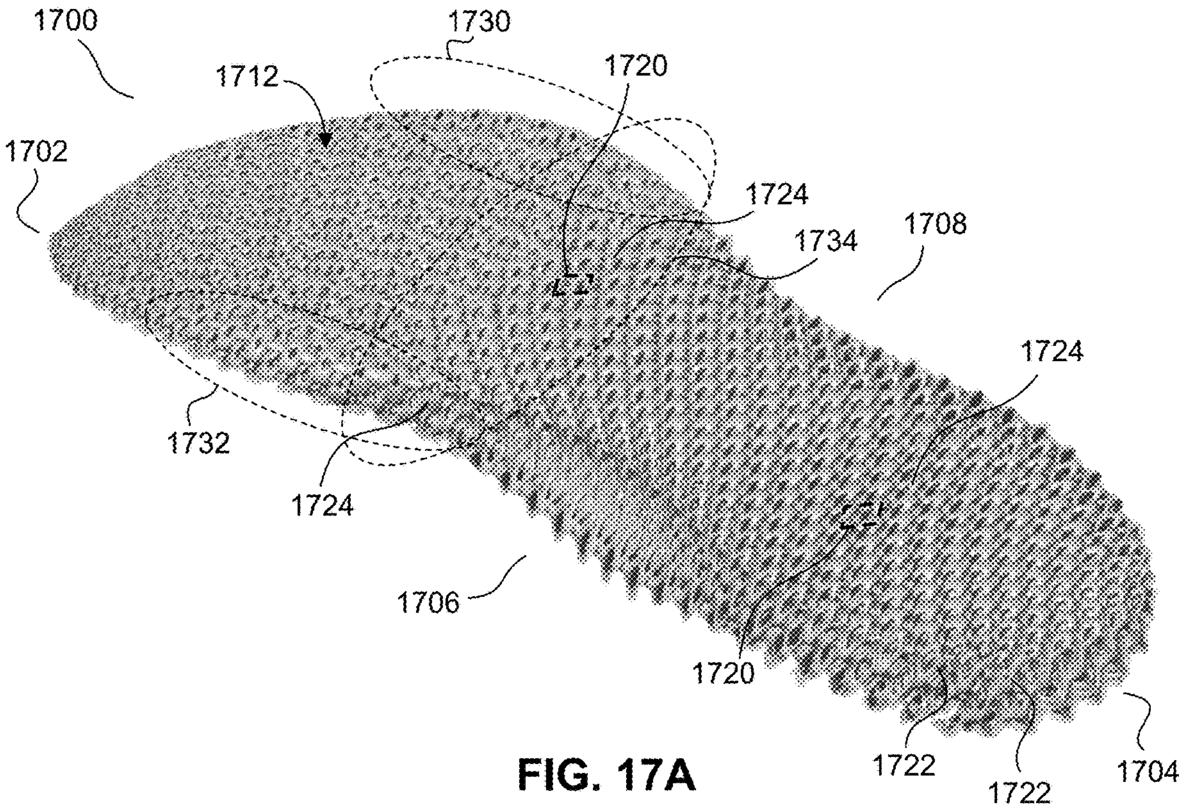
FIG. 17A is a medial perspective view of a three-dimensional mesh customized for a forefoot striker according to some embodiments.
Figure 17B:
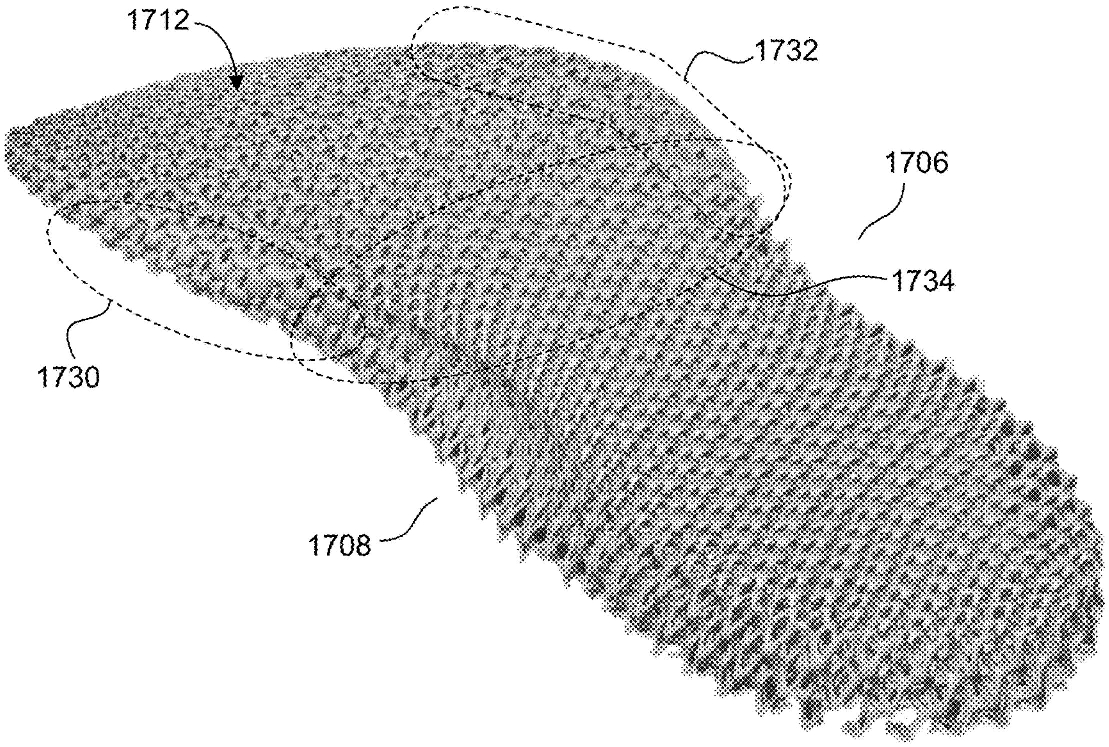
FIG. 17B is a lateral perspective view of a three-dimensional mesh customized for a forefoot striker according to some embodiments.
Figure 17C:
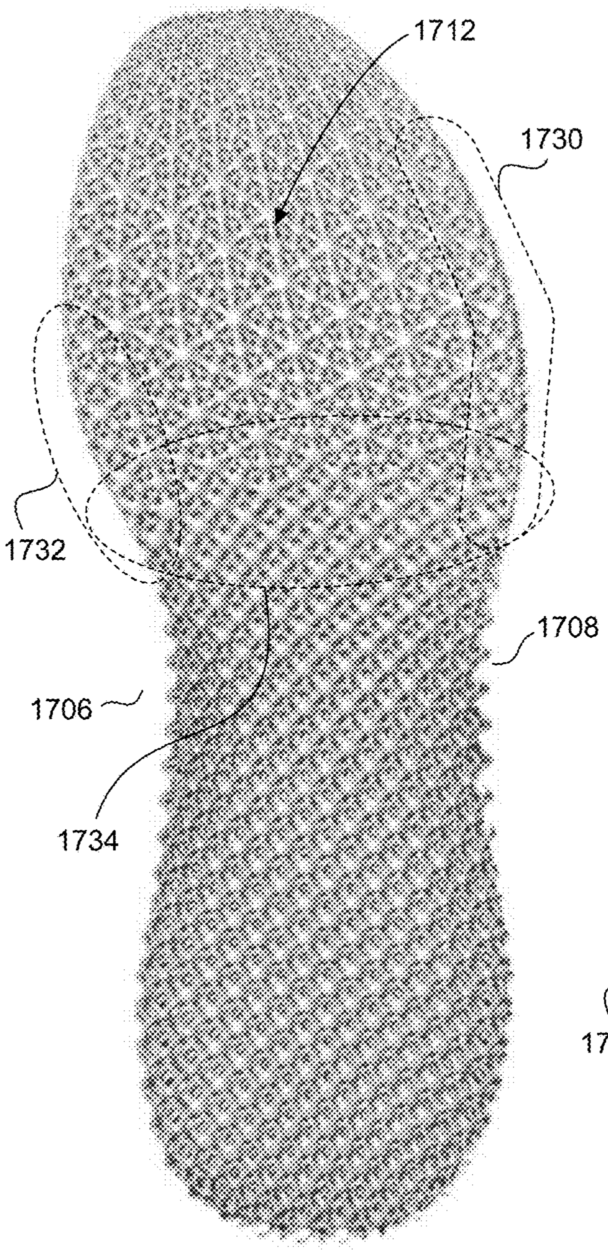
FIG. 17C is a bottom side view of a three-dimensional mesh customized for a forefoot striker according to some embodiments.
Figure 17D:
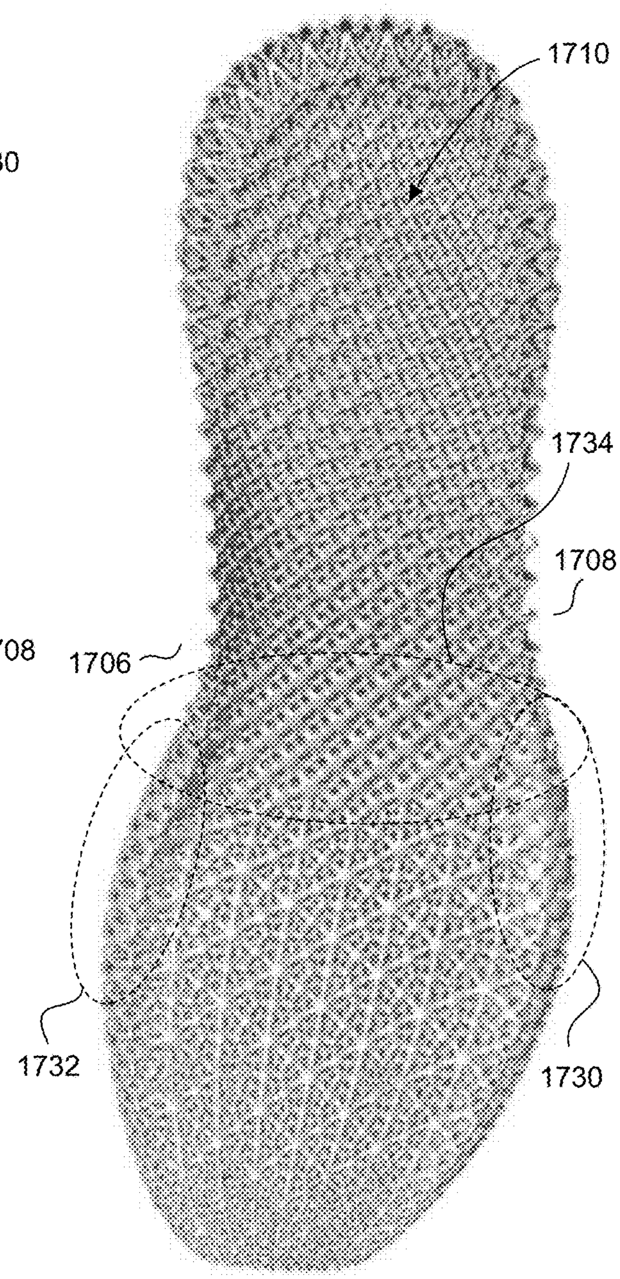
FIG. 17D is a top side view of a three-dimensional mesh customized for a forefoot striker according to some embodiments.
Figure 17E:
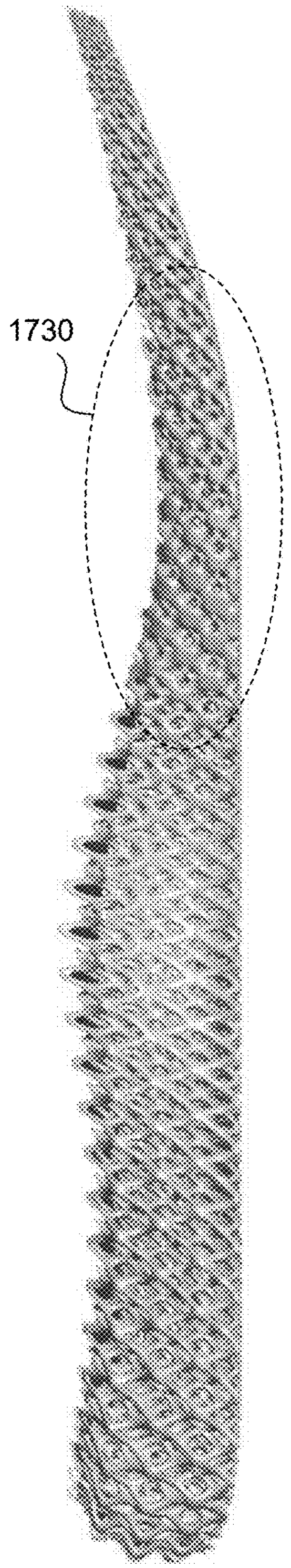
FIG. 17E is a lateral side view of a three-dimensional mesh customized for a forefoot striker according to some embodiments.
Figure 17F:
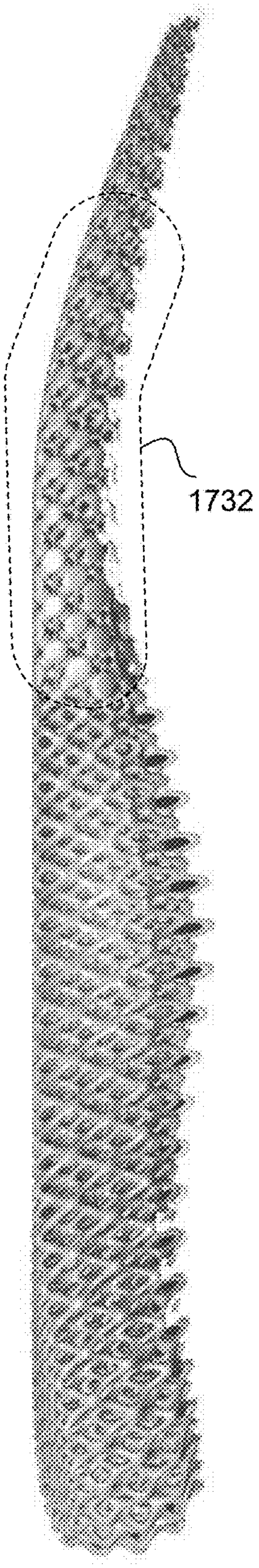
FIG. 17F is a medial side view of a three-dimensional mesh customized for a forefoot striker according to some embodiments.

FIGS. 17A-17F show an exemplary three-dimensional mesh 1700 customized for a forefoot striker according to some embodiments. FIG. 17A shows a medial bottom perspective view, FIG. 17B shows a lateral bottom perspective view, FIG. 17C shows a bottom side view, FIG. 17D shows a top side view, FIG. 17E shows a lateral side view, and FIG. 17F shows a medial side view of three-dimensional mesh 1700.

Three-dimensional mesh 1700 includes a forefoot end 1702, a heel end 1704, a medial side 1706, a lateral side 1708, a top side 1710, and a bottom side 1712. And three-dimensional mesh 1700 is defined by a plurality of interconnected unit cells 1720 including struts 1722 connected at nodes 1724.

As shown in FIGS. 17A-17F, three-dimensional mesh 1700 includes a first zone 1730, second zone 1732, and third zone 1734 having struts 1722 with relatively large thickness. Nodes 1724 within zones 1730, 1732, and 1734 also have a relatively large thickness. Zones 1730, 1732, and 1734 provide a high degree of support for zones of three-dimensional mesh 1700 associated with areas typically subject to large stresses for a forefoot striker. In some embodiments, third zone 1734 may be a transition zone having unit cells 1720 with varying strut 1722 and node 1724 thickness to gradually transition from relatively thicker unit cells 1720 in a forefoot portion of three-dimensional mesh 1700 to relatively thinner unit cells 1720 in midfoot and heel portions of three-dimensional mesh 1700.

While FIGS. 17A-17F show zones 1730, 1732, and 1734 as having struts 1722 and nodes 1724 within increased thickness, increased support in these zones may be alternatively or additionally be provided by relatively high valence numbers in the zones, making unit cells 1720 in these zones with a different material, increasing the unit cell density within the zone (e.g., by populating two unit cells 1720 in a single warped or unwarped lattice cell), or a combination thereof.

Figure 18A:
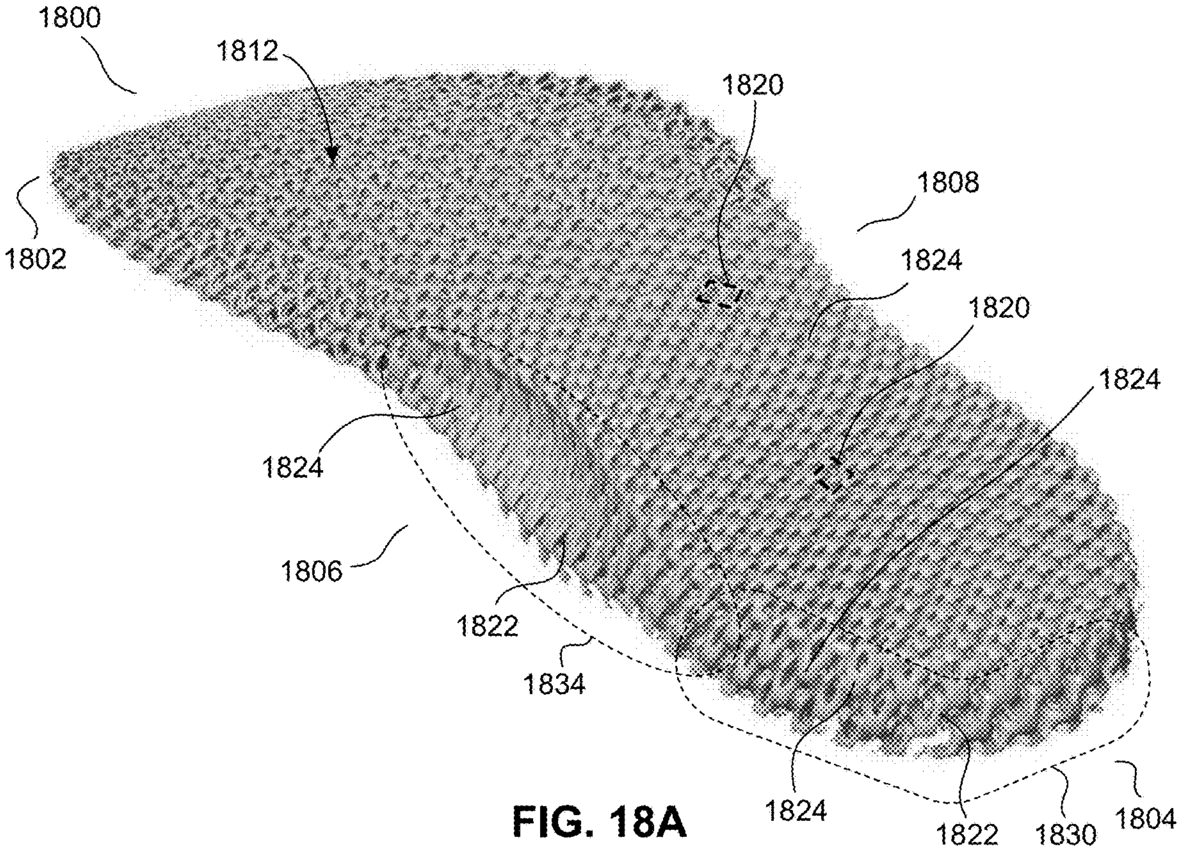
FIG. 18A is a medial perspective view of a three-dimensional mesh customized for a rearfoot striker according to some embodiments.
Figure 18B:
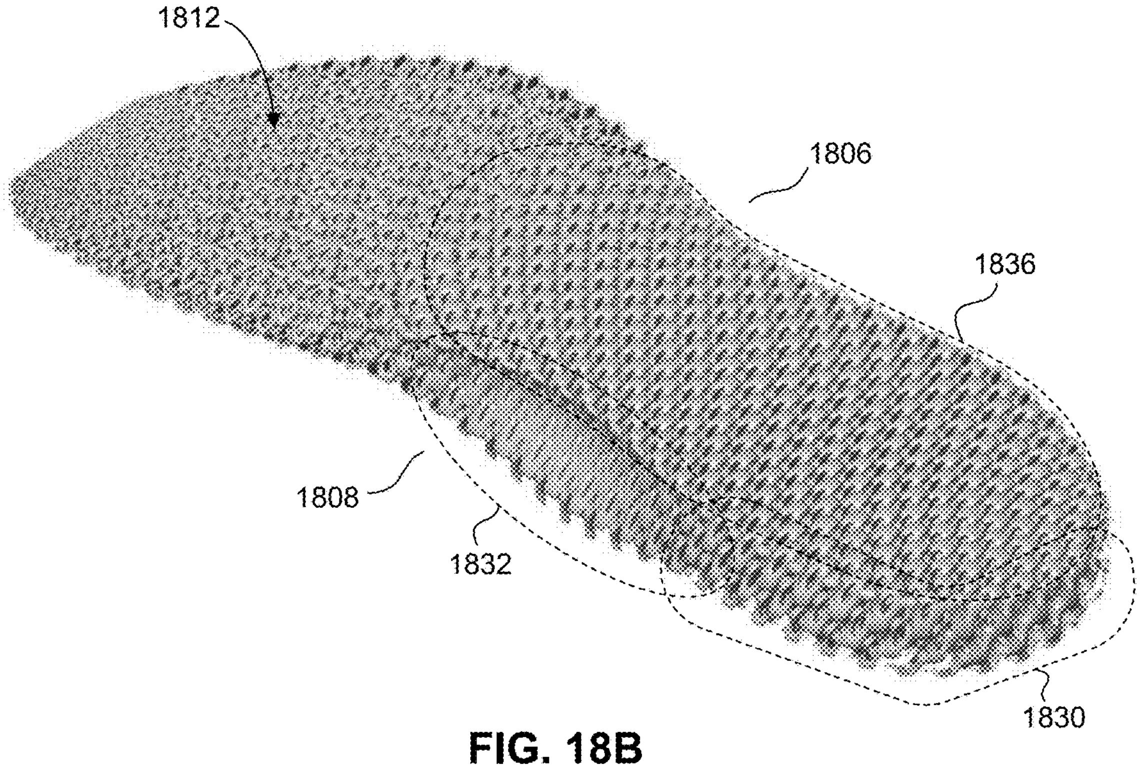
FIG. 18B is a lateral perspective view of a three-dimensional mesh customized for a rearfoot striker according to some embodiments.
Figure 18C:
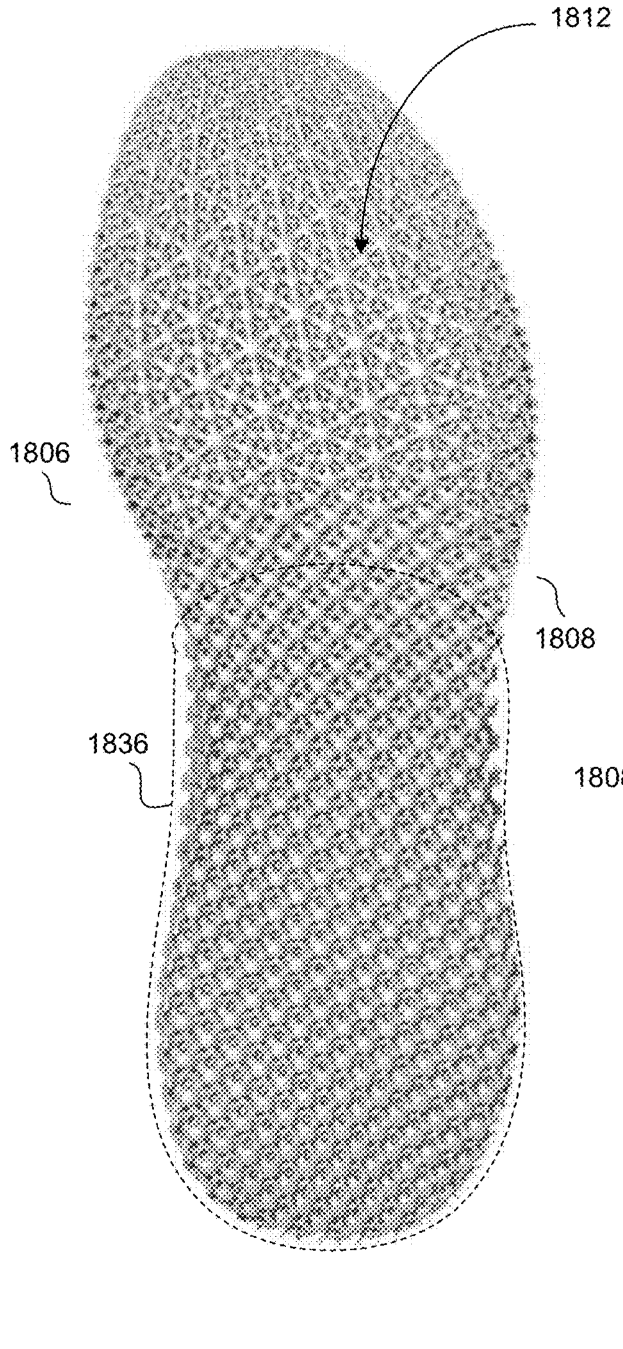
FIG. 18C is a bottom side view of a three-dimensional mesh customized for a rearfoot striker according to some embodiments.
Figure 18D:
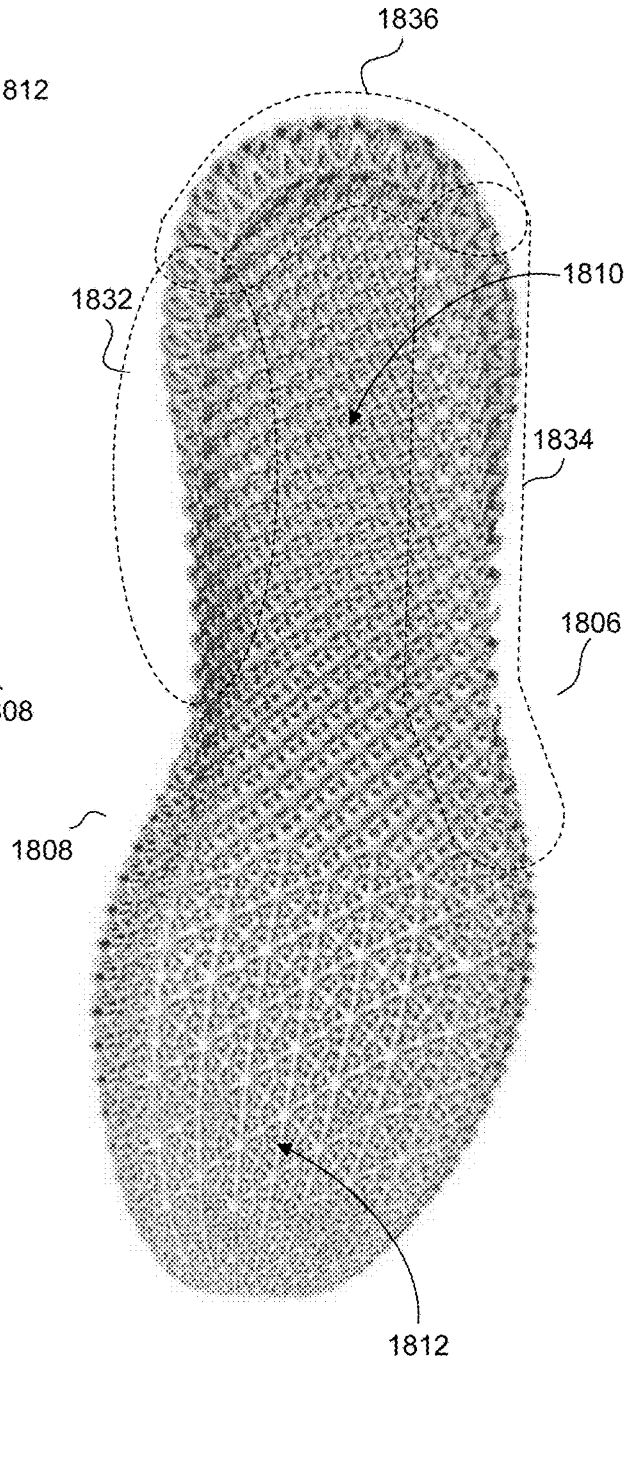
FIG. 18D is a top side view of a three-dimensional mesh customized for a rearfoot striker according to some embodiments.
Figure 18E:
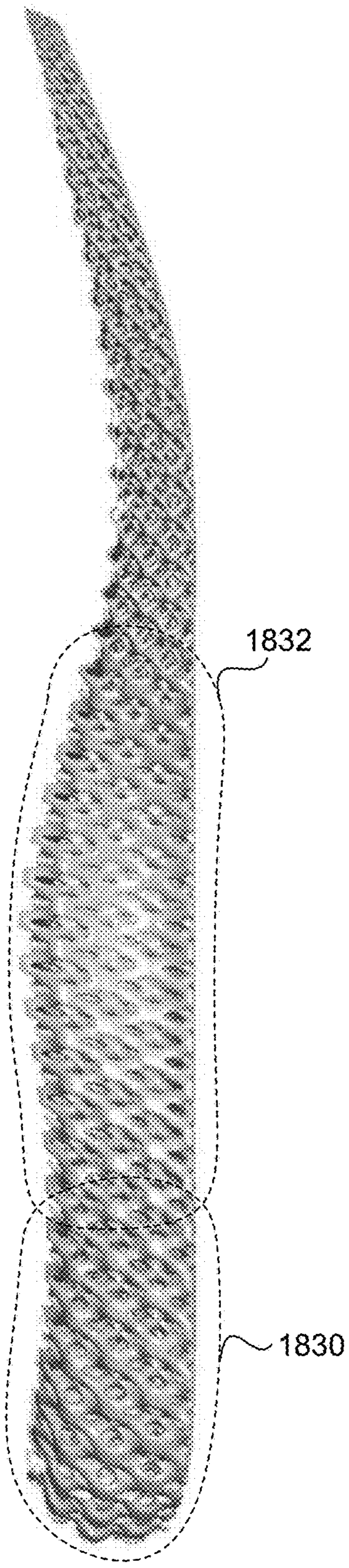
FIG. 18E is a lateral side view of a three-dimensional mesh customized for a rearfoot striker according to some embodiments.
Figure 18F:
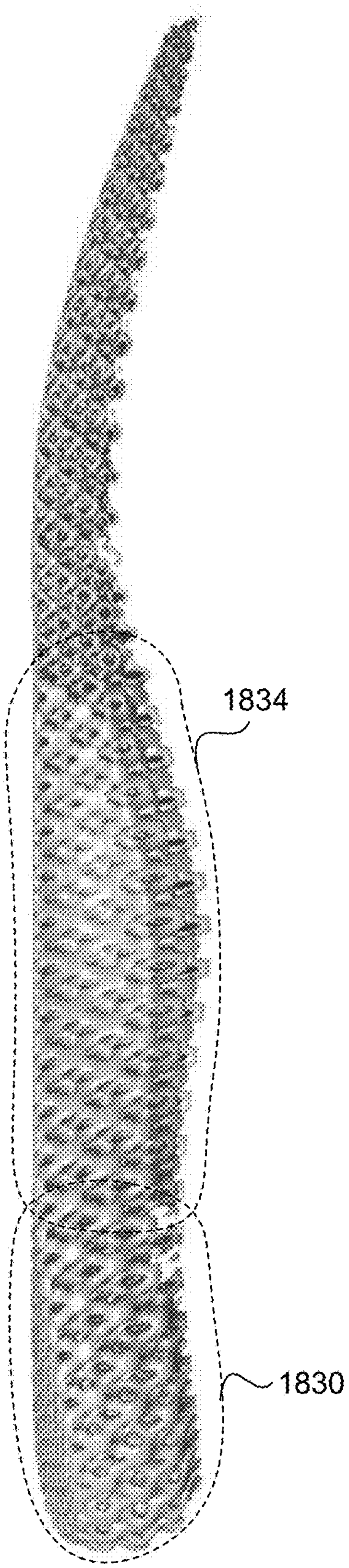
FIG. 18F is a medial side view of a three-dimensional mesh customized for a rearfoot striker according to some embodiments.

FIGS. 18A-18F show an exemplary three-dimensional mesh 1800 customized for a rearfoot striker according to some embodiments. FIG. 18A shows a medial bottom perspective view, FIG. 18B shows a lateral bottom perspective view, FIG. 18C shows a bottom side view, FIG. 18D shows a top side view, FIG. 18E shows a lateral side view, and FIG. 18F shows a medial side view of three-dimensional mesh 1800.

Three-dimensional mesh 1800 includes a forefoot end 1802, a heel end 1804, a medial side 1806, a lateral side 1808, a top side 1810, and a bottom side 1812. And three-dimensional mesh 1800 is defined by a plurality of interconnected unit cells 1820 including struts 1822 connected at nodes 1824.

As shown in FIGS. 18A-18F, three-dimensional mesh 1800 includes a first zone 1830, second zone 1832, and third zone 1834 having struts 1822 with relatively large thickness. Nodes 1824 within zones 1830, 1832, and 1834 also have a relatively large thickness. Zones 1830, 1832, and 1834 provide a high degree of support for zones of three-dimensional mesh 1800 associated with areas typically subject to large stresses for a rearfoot striker. In some embodiments, as shown for example in FIGS. 18B and 18C, bottom side 1812 of three-dimensional mesh 1800 may include a fourth zone 1836 having relatively large nodes 1724 in a heel portion and midfoot portion of three-dimensional mesh 1800 to provide additional support for a rearfoot striker.

While FIGS. 18A-18F show zones 1830, 1832, 1834, and 1836 as having struts 1822 and/or nodes 1824 within increased thickness, increased support in these zones may be alternatively or additionally be provided by relatively high valence numbers in the zones, making unit cells 1820 in these zones with a different material, increasing the unit cell density within the zone (e.g., by populating two unit cells 1820 in a single warped or unwarped lattice cell), or a combination thereof.

Figure 19A:
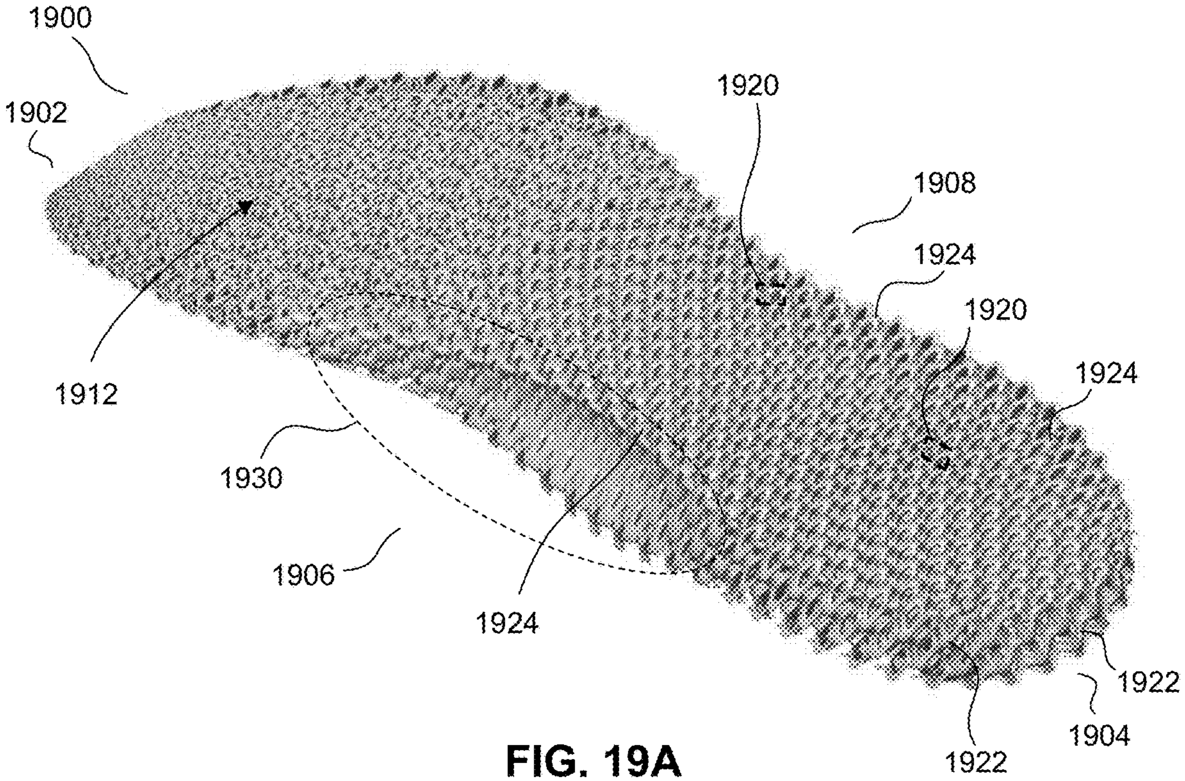
FIG. 19A is a medial perspective view of a three-dimensional mesh customized to provide arch support according to some embodiments.
Figure 19B:
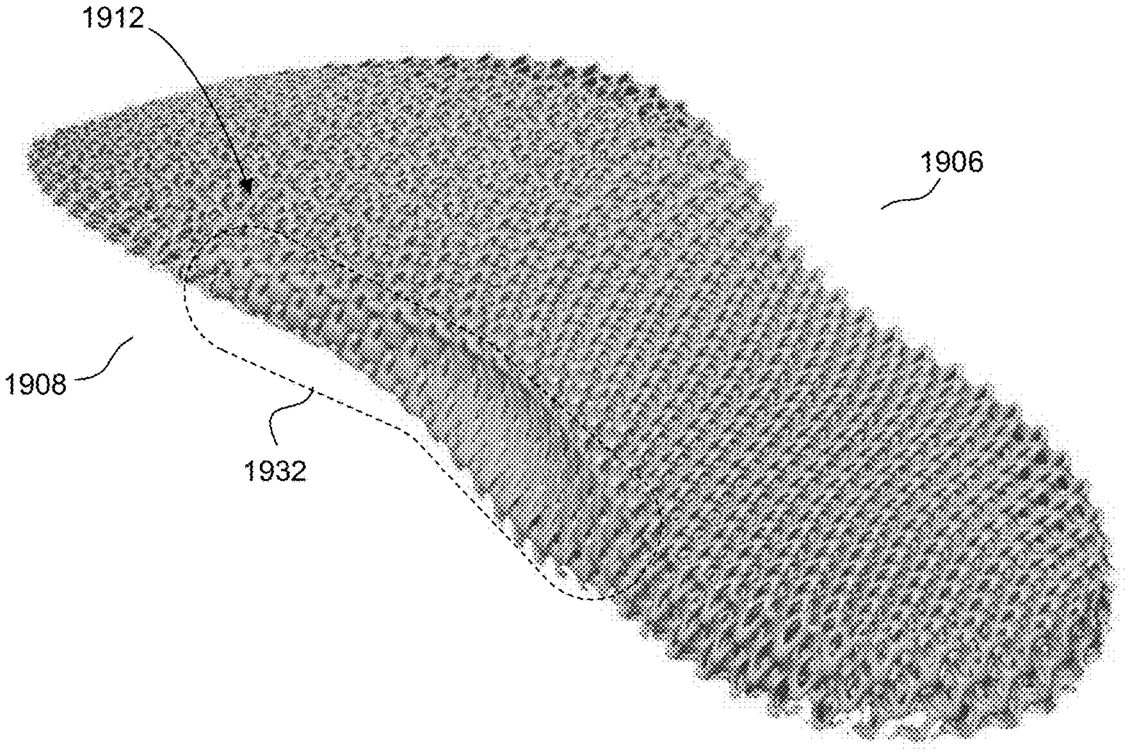
FIG. 19B is a lateral perspective view of a three-dimensional mesh customized to provide arch support according to some embodiments.
Figure 19C:
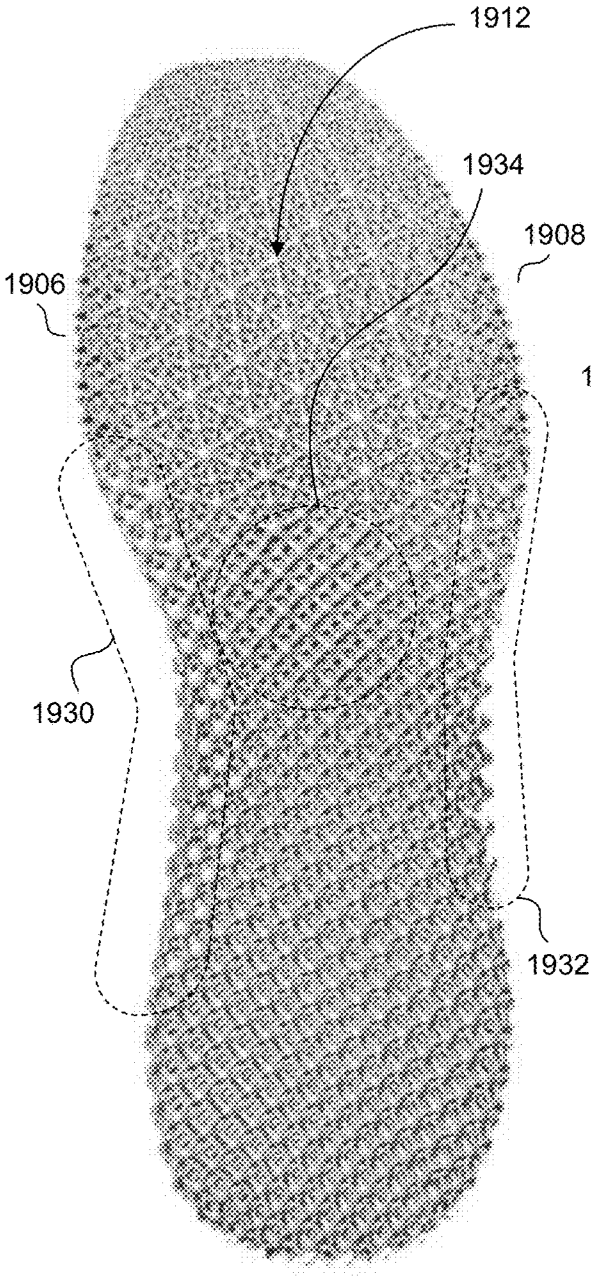
FIG. 19C is a bottom side view of a three-dimensional mesh customized to provide arch support according to some embodiments.
Figure 19D:
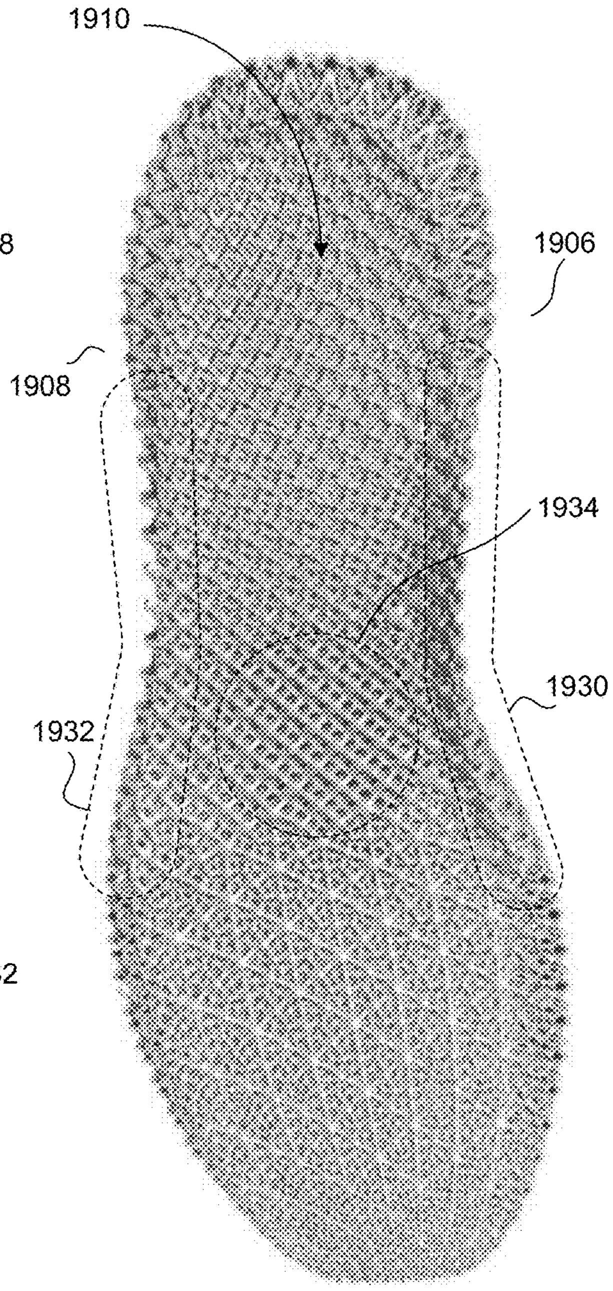
FIG. 19D is a top side view of a three-dimensional mesh customized to provide arch support according to some embodiments.
Figure 19E:
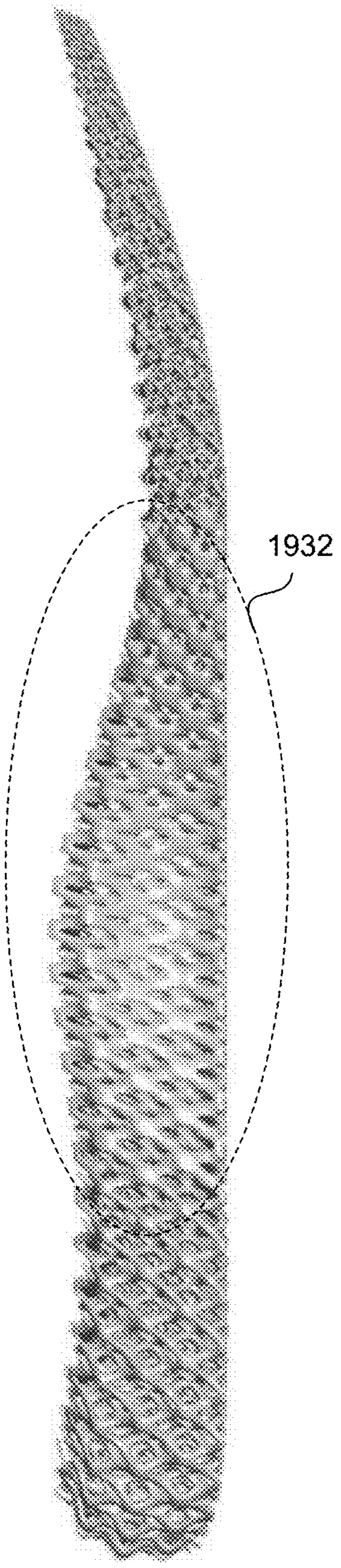
FIG. 19E is a lateral side view of a three-dimensional mesh customized to provide arch support according to some embodiments.
Figure 19F:
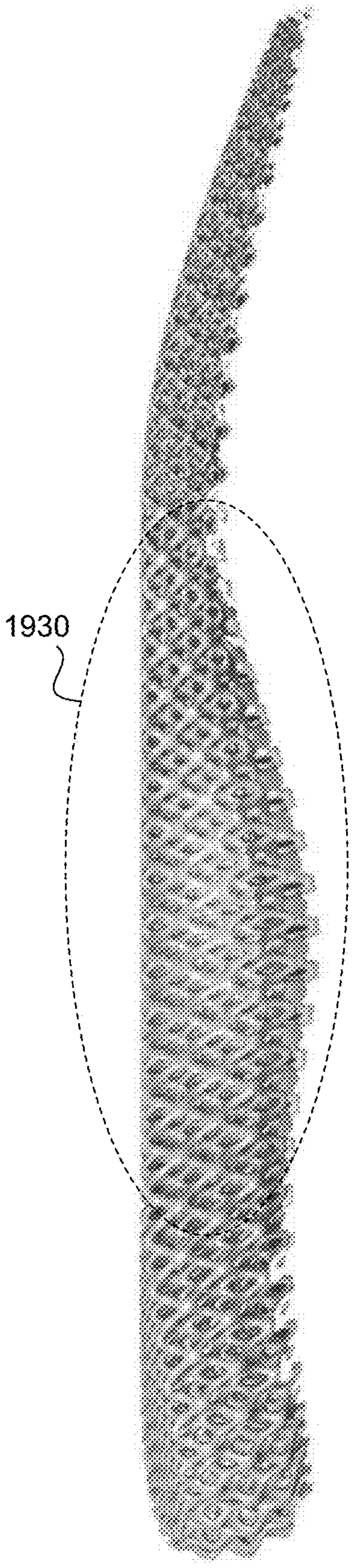
FIG. 19F is a medial side view of a three-dimensional mesh customized to provide arch support according to some embodiments.

FIGS. 19A-19F show an exemplary three-dimensional mesh 1900 customized to provide arch support according to some embodiments. FIG. 19A shows a medial bottom perspective view, FIG. 19B shows a lateral bottom perspective view, FIG. 19C shows a bottom side view, FIG. 19D shows a top side view, FIG. 19E shows a lateral side view, and FIG. 19F shows a medial side view of three-dimensional mesh 1900.

Three-dimensional mesh 1900 includes a forefoot end 1902, a heel end 1904, a medial side 1906, a lateral side 1908, a top side 1910, and a bottom side 1912. And three-dimensional mesh 1900 is defined by a plurality of interconnected unit cells 1920 including struts 1922 connected at nodes 1924.

As shown in FIGS. 19A-19F, three-dimensional mesh 1900 includes a first zone 1930 and a second zone 1932 having struts 1922 with relatively large thickness. Nodes 1924 within zones 1930 and 1932 also have a relatively large thickness. Zones 1930 and 1932 provide a high degree of support for zones of three-dimensional mesh 1900 associated with areas typically subject to large stresses for an individual having a large midfoot arch. In some embodiments, as shown for example in FIGS. 19C and 19D, a three-dimensional mesh 1900 may include a third zone 1934 having relatively thin struts 1922 and nodes 1924 located in a central midfoot area of three-dimensional mesh 1900 to provide additional cushioning for the arch of a high-arched individual.

While FIGS. 19A-19F show zones 1930, 1932, and 1934 as having struts 1922 and nodes 1924 within increased or decreased thickness, increased support/cushioning in these zones may be alternatively or additionally provided by relatively high/low valence numbers in the zones, making unit cells 1820 in these zones with a different material, increasing/decreasing the unit cell density within the zone (e.g., by populating one or two unit cells 1920 in a single warped or unwarped lattice cell), or a combination thereof.

Figure 20A:
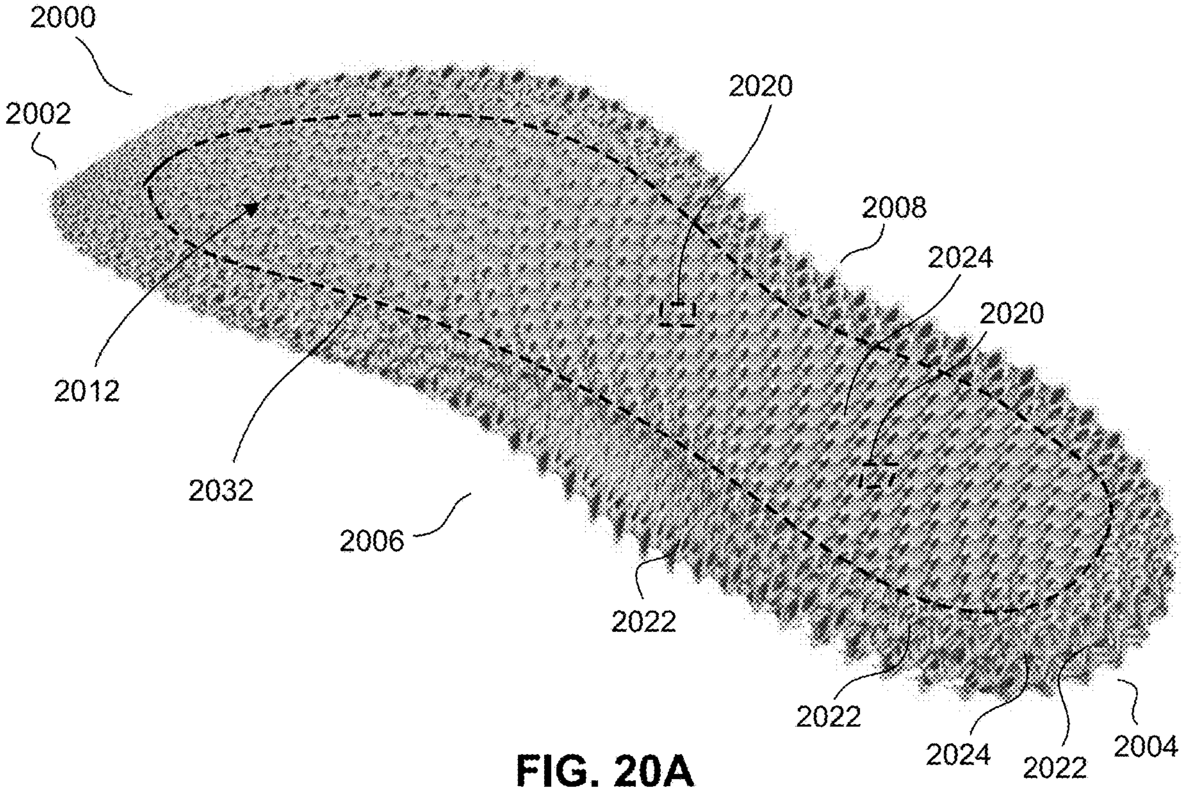
FIG. 20A is a medial perspective view of a lightweight three-dimensional mesh according to some embodiments.
Figure 20B:
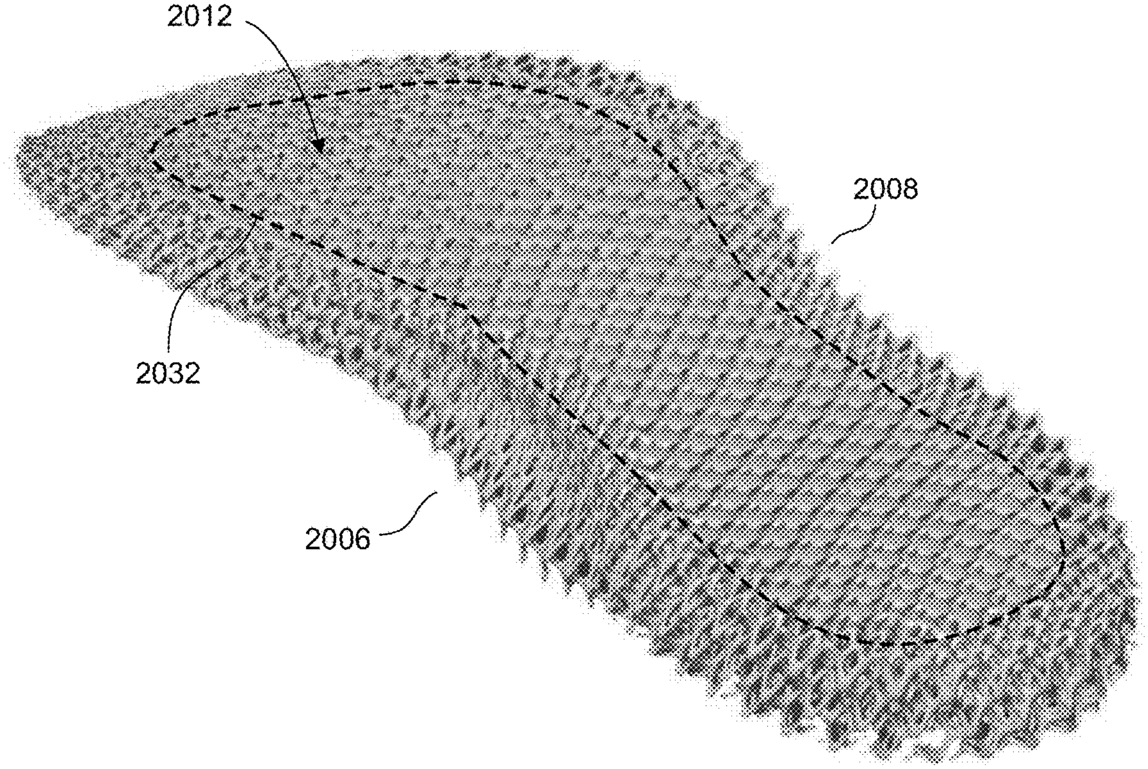
FIG. 20B is a lateral perspective view of a lightweight three-dimensional mesh according to some embodiments.
Figure 20C:
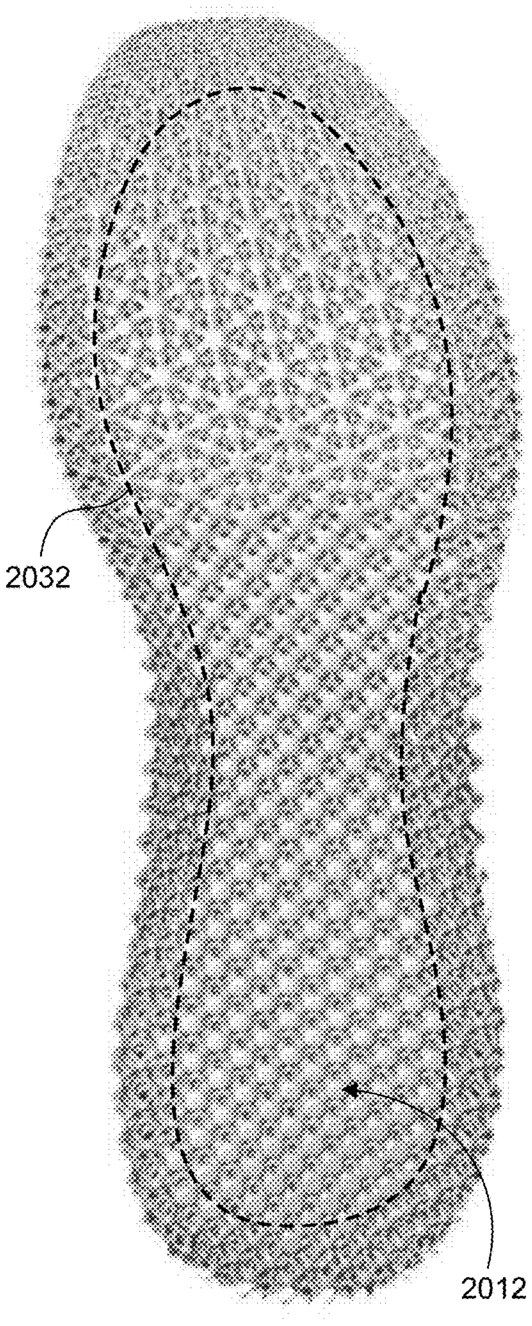
FIG. 20C is a bottom side view of a lightweight three-dimensional mesh according to some embodiments.
Figure 20D:
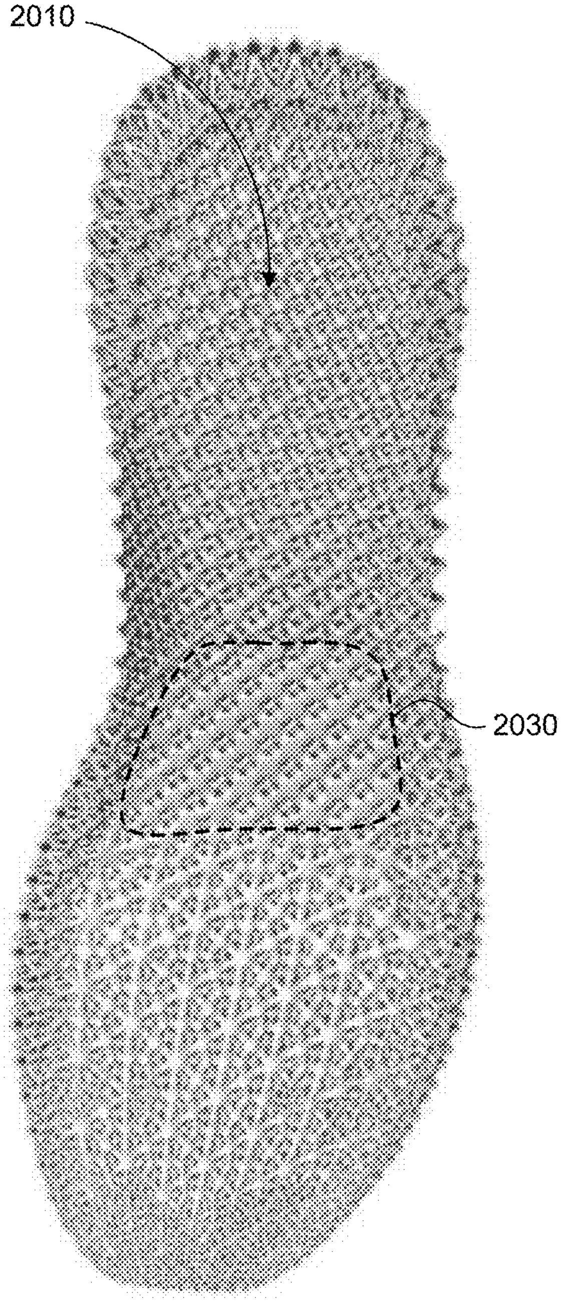
FIG. 20D is a top side view of a lightweight three-dimensional mesh according to some embodiments.
Figure 20E:
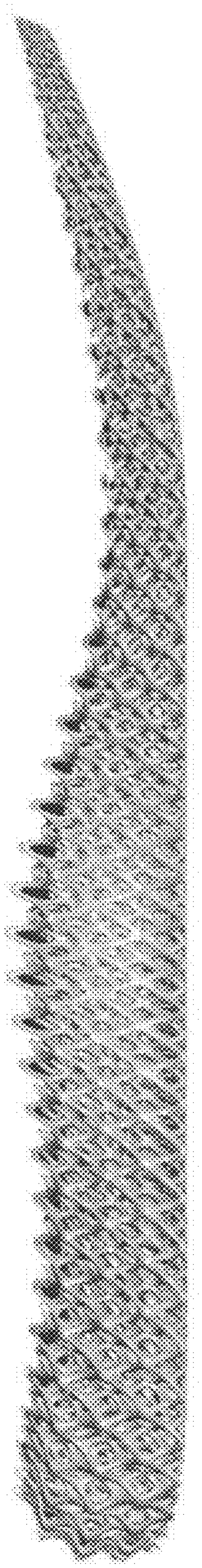
FIG. 20E is a lateral side view of a lightweight three-dimensional mesh according to some embodiments.
Figure 20F:
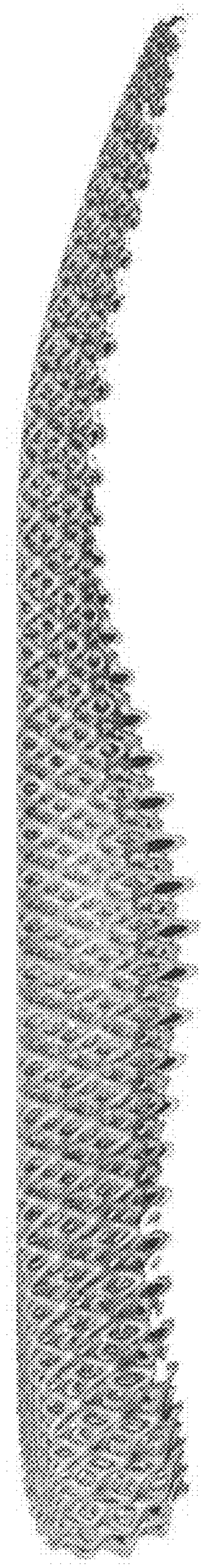
FIG. 20F is a medial side view of a lightweight three-dimensional mesh according to some embodiments.

FIGS. 20A-20F show an exemplary lightweight three-dimensional mesh 2000 according to some embodiments. FIG. 20A shows a medial bottom perspective view, FIG. 20B shows a lateral bottom perspective view, FIG. 20C shows a bottom side view, FIG. 20D shows a top side view, FIG. 20E shows a lateral side view, and FIG. 20F shows a medial side view of three-dimensional mesh 2000.

Three-dimensional mesh 2000 includes a forefoot end 2002, a heel end 2004, a medial side 2006, a lateral side 2008, a top side 2010, and a bottom side 2012. And three-dimensional mesh 2000 is defined by a plurality of interconnected unit cells 2020 including struts 2022 connected at nodes 2024.

As shown in FIGS. 20A-20F, top side 2010 and bottom side 2012 of three-dimensional mesh 2000 include zone a first zone 2030 and a second zone 2032, respectively, with nodes 1924 with a relatively large thickness. Thick nodes 2024 on top side 2010 and bottom side 2012 provide support and propulsion for three-dimensional mesh while also allowing three-dimensional mesh to be lightweight. In such embodiments, three-dimensional mesh 2000 may have a smaller vertical dimension than other three-dimensional meshes without sacrificing support and/or propulsion characteristics, and in some cases provide improved propulsion characteristics. Also, in some embodiments, three-dimensional mesh 2000 may be made with a lighter weight material than other three-dimensional meshes without sacrificing support and/or propulsion characteristics, and in some cases provide improved support and/or propulsion characteristics.

While FIGS. 20A-20F show top side 2010 and bottom side 2012 having nodes 1724 with increased thickness, the weight of three-dimensional mesh 2000 may be alternatively or additionally be tailored by tailoring the valence numbers on top side 2010 and/or bottom side 2012, making unit cells 2020 on top side 2010 and/or bottom side 2012 with a different material, increasing/decreasing the unit cell density on top side 2010 and/or bottom side 2012 (e.g., by populating one or two unit cells 2020 in a single warped or unwarped lattice cell), or a combination thereof.

Figure 21:
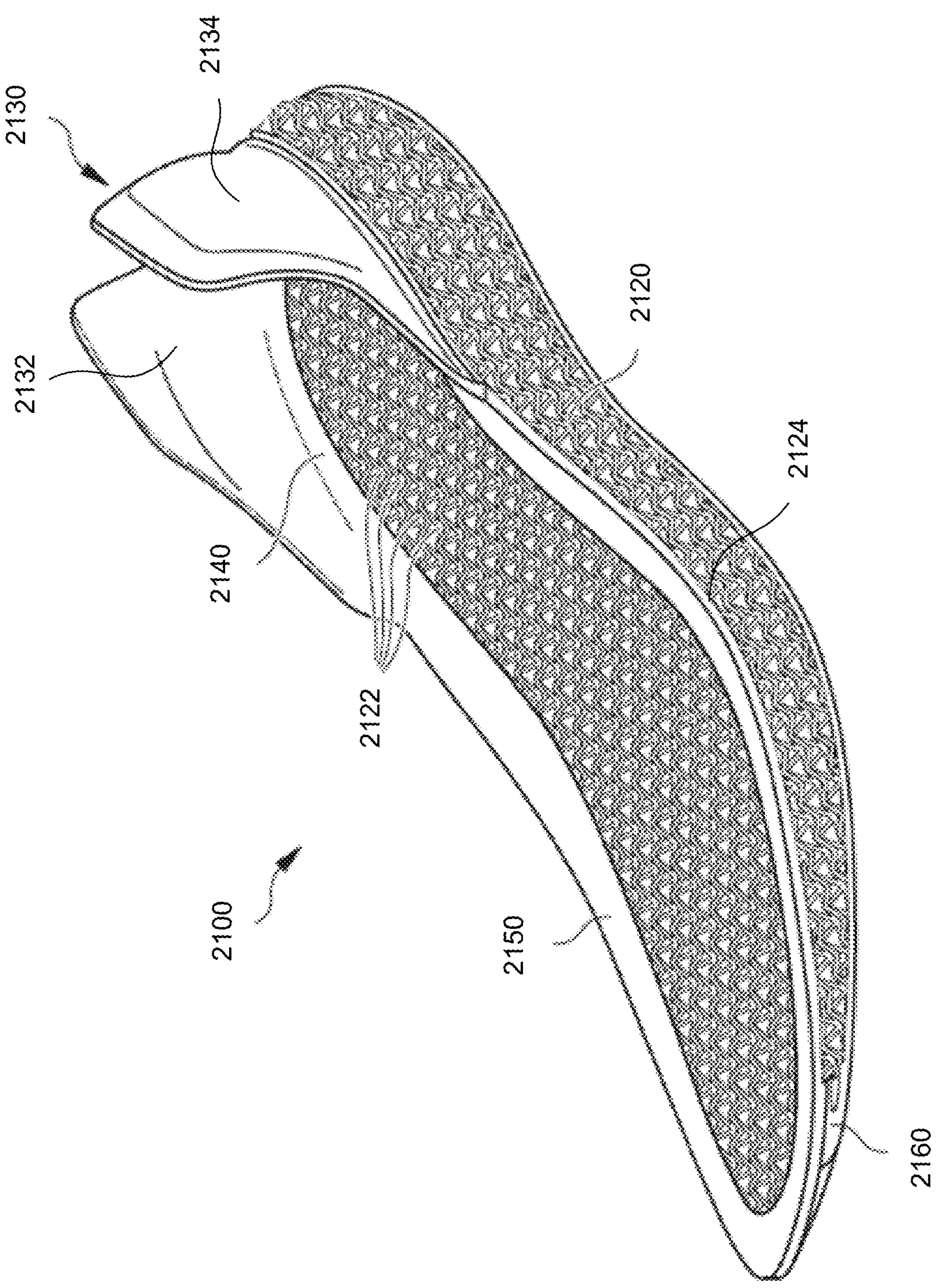
FIG. 21 is a midsole according to some embodiments.

FIG. 21 shows a perspective view of a midsole 2100 according to some embodiments. Midsole 2100 includes a three-dimensional mesh 2120 having a plurality of unit cells 2122, a heel element 2130, which three-dimensionally encompasses a heel of a wearer, and a base portion 2140 interconnecting heel element 2130 and three-dimensional mesh 2120. In some embodiments, three-dimensional mesh 2120 may be the same as or similar to three-dimensional mesh 320.

Base portion 2140 may include an extension arranged to connect to a plurality of adjacent unit cells 2122. The plurality of unit cells 2122 includes a first plurality of adjacent unit cells 2122 positioned along an edge of the three-dimensional mesh 2120, as well as a second plurality of adjacent unit cells 2122 not positioned along the edge of the three-dimensional mesh 2120. The first and second pluralities of adjacent unit cells 2122 may be arranged adjacent to each other. Since base portion 2140 is connected to a plurality of adjacent unit cells 2122 not positioned at an edge of 2124 three-dimensional mesh 2120 (in addition to the plurality of adjacent unit cells 2122 positioned at edge 2124 of three-dimensional mesh 2120), forces and torques may be transferred to the three-dimensional mesh via an interface with unit cells 2122 effectively arranged in two dimensions. This may improve the transfer of forces and torques such that heel element 2130 is able to provide increased stability. It may also reduce the forces and torques that need to be transferred per unit cell 2122. Hence, the individual unit cells 2122 may be less susceptible to breaking.

Heel element 2130 may be three-dimensionally shaped such that it can be adapted to the heel of a wearer and/or the expected force profile. In some embodiments, the heel element 2130 may be tapered, e.g. as shown in FIG. 21. In some embodiments, heel element 2130 may become thicker from a top side of the heel element 2130 towards the base portion 2140 connecting it to three-dimensional mesh 2120.

In some embodiments, heel element 2130 may include two elevated portions 2132 and 2134, which are arranged at the lateral and medial sides of the heel, respectively. Elevated portions 2132 and 2134 may help to provide a large degree of stability, especially in relation to lateral movements.

In some embodiments, midsole 2100 may include a rim 2150. Rim 2150 may circulate along a rim of a top side of three-dimensional mesh 2120, e.g. extending from a medial side of base portion 2140 along the rim of the midfoot and forefoot as well as toe regions of midsole 2100 until a lateral side of base portion 2140. In some embodiments, rim 2150 may serve as a means for supporting the attachment of midsole 2100 to an upper (e.g., upper 120).

In some embodiments, midsole 2100 may include a solid front portion 2160 located at the forefoot end of midsole 2100. Solid front portion 2160 may not comprise any lattice structure. Rather, solid front portion 2160 may be implemented as a continuous element.

Figure 22:
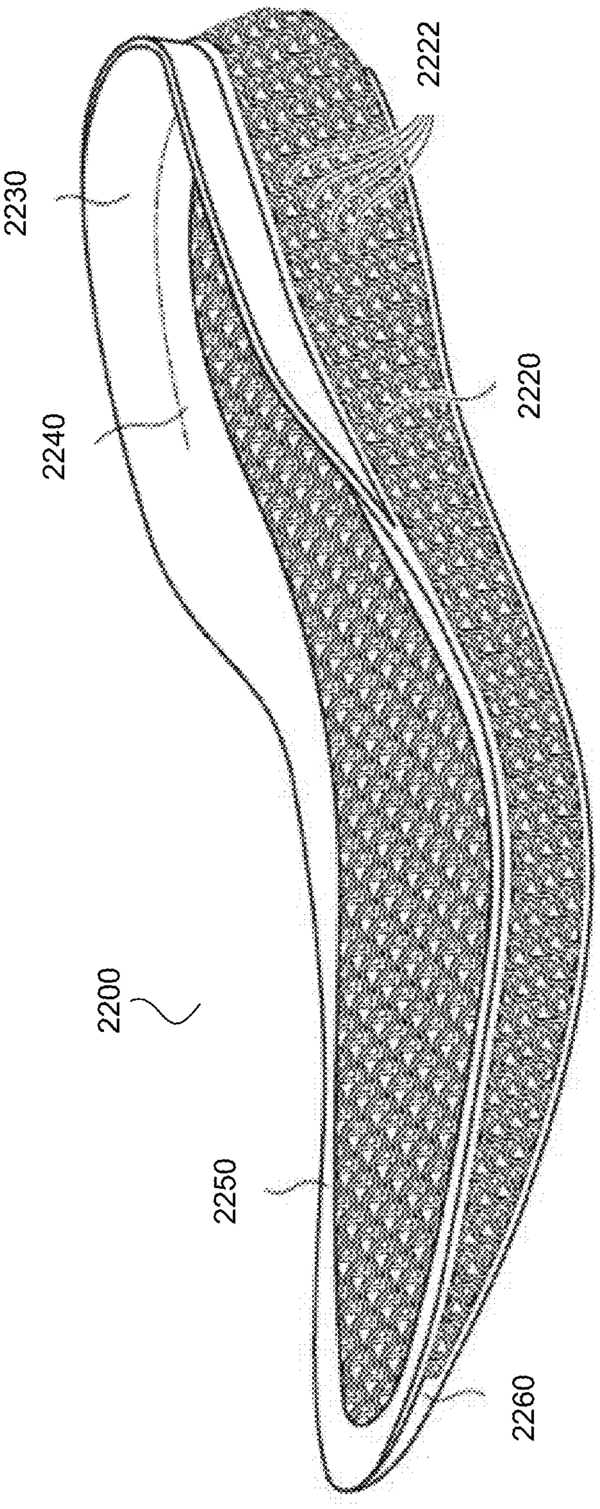
FIG. 22 is a midsole according to some embodiments.

FIG. 22 shows a perspective view of a midsole 2200 according to some embodiments. Similar to midsole 2100, midsole 2200 may include a three-dimensional mesh 2220 with a plurality of unit cells 2222, a heel element 2230, a base portion 2240, a rim 2250, and a solid front portion 2260. In some embodiments, three-dimensional mesh 2220 may be the same as or similar to three-dimensional mesh 320.

In some embodiments, heel element 2230 may have a relatively constant height at the rear side of the heel as well as at the lateral and medial sides of the heel adjacent to the rear side. The height of heel element 2230 may only be reduced at its ends, both at the medial and laterals sides. Heel element 2230 may be three-dimensionally formed and its cross-section may increase from its top towards its bottom such that a relatively thick cross-section is provided at the interface towards base portion 2240 that connects heel element 2230 to three-dimensional mesh 2220.

In some embodiments, heel elements 2130/2230, rims 2150/2250, and/or solid front portions 2160/2260 may be the same as or similar to the heel elements, rim elements, and front portions described in U.S. patent application Ser. No. 15/195,694, filed on Jun. 28, 2016, which is hereby incorporated in its entirety by reference thereto.

One or more aspects of the methods of manufacturing a midsole for an article of footwear discussed herein, or any part(s) or function(s) thereof, may be implemented using hardware, software modules, firmware, tangible computer readable media having instructions stored thereon, or a combination thereof and may be implemented in one or more computer systems or other processing systems.

Figure 23:
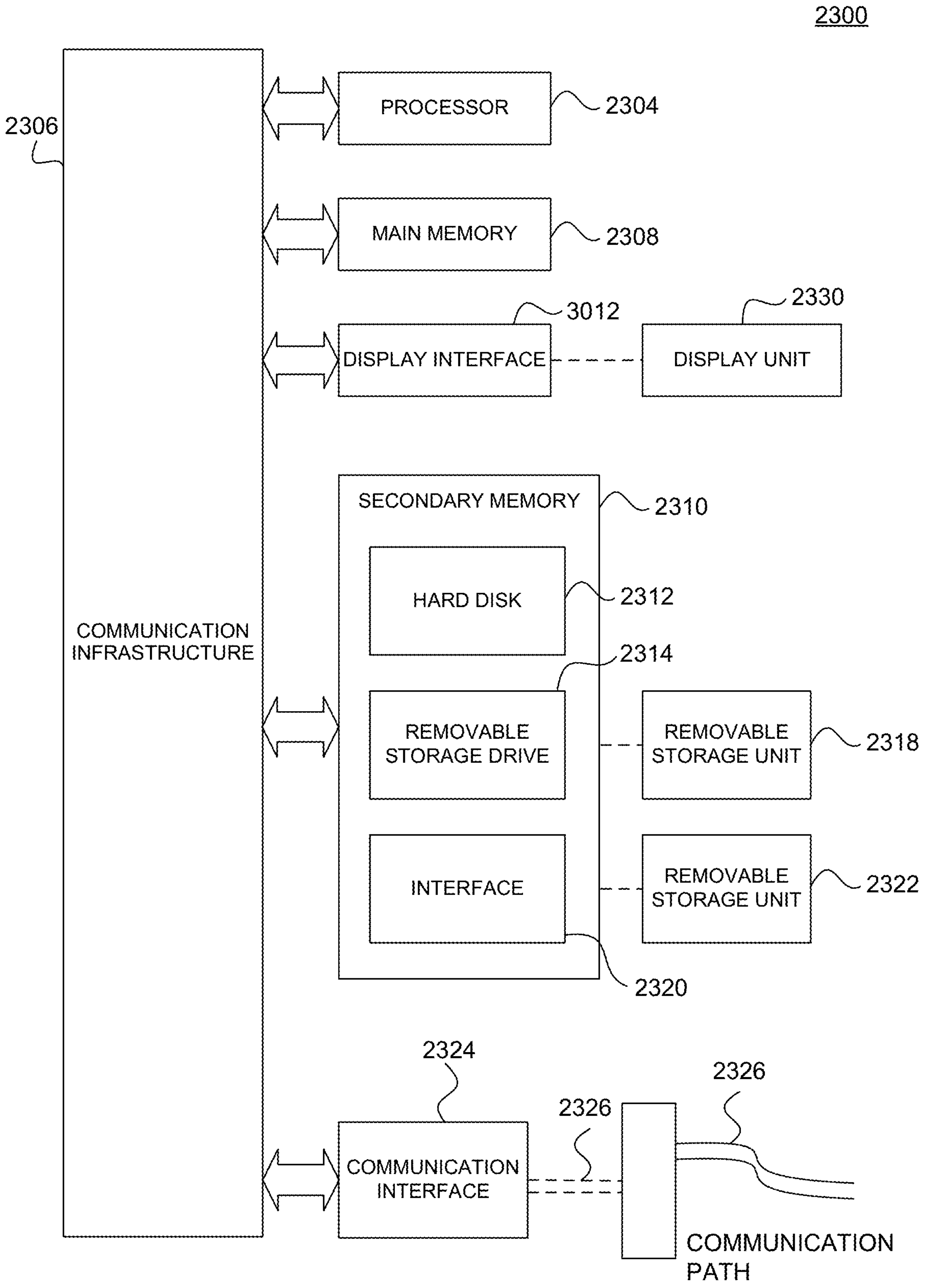
FIG. 23 is a schematic block diagram of an exemplary computer system in which embodiments may be implemented.

FIG. 23 illustrates an exemplary computer system 2300 in which embodiments, or portions thereof, may be implemented as computer-readable code. For example, aspects of the methods discussed herein that may be implemented in one or more computer systems include, but are not limited to, collecting a biometric data profile, generating a warped cubic lattice based on the biometric data profile, obtaining an already generated warped cubic lattice structure, populating lattice cells with one or more lattice unit cells, and tailoring properties of the lattice unit cells (e.g., base geometry, size, and valence) may be implemented in computer system 2300 using hardware, software, firmware, tangible computer readable media having instructions stored thereon, or a combination thereof and may be implemented in one or more computer systems or other processing systems.

If programmable logic is used, such logic may execute on a commercially available processing platform or a special purpose device. One of ordinary skill in the art may appreciate that embodiments of the disclosed subject matter can be practiced with various computer system configurations, including multi-core multiprocessor systems, minicomputers, and mainframe computers, computer linked or clustered with distributed functions, as well as pervasive or miniature computers that may be embedded into virtually any device.

For instance, at least one processor device and a memory may be used to implement the above described embodiments. A processor device may be a single processor, a plurality of processors, or combinations thereof. Processor devices may have one or more processor "cores."

Various embodiments of the inventions may be implemented in terms of this example computer system 2300. After reading this description, it will become apparent to a person skilled in the relevant art how to implement one or more of the inventions using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 2304 may be a special purpose or a general purpose processor device. As will be appreciated by persons skilled in the relevant art, processor device 2304 may also be a single processor in a multi-core/multiprocessor system, such system operating alone, or in a cluster of computing devices operating in a cluster or server farm. Processor device 2304 is connected to a communication infrastructure 2306, for example, a bus, message queue, network, or multi-core message-passing scheme.

Computer system 2300 also includes a main memory 2308, for example, random access memory (RAM), and may also include a secondary memory 2310. Secondary memory 2310 may include, for example, a hard disk drive 2312, or removable storage drive 2314. Removable storage drive 2314 may include a floppy disk drive, a magnetic tape drive, an optical disk drive, a flash memory, a Universal Serial Bus (USB) drive, or the like. The removable storage drive 2314 reads from and/or writes to a removable storage unit 2318 in a well-known manner. Removable storage unit 2318 may include a floppy disk, magnetic tape, optical disk, etc. which is read by and written to by removable storage drive 2314. As will be appreciated by persons skilled in the relevant art, removable storage unit 2318 includes a computer usable storage medium having stored therein computer software and/or data.

Computer system 2300 (optionally) includes a display interface 2302 (which can include input and output devices such as keyboards, mice, etc.) that forwards graphics, text, and other data from communication infrastructure 2306 (or from a frame buffer not shown) for display on display unit 2330.

In alternative implementations, secondary memory 2310 may include other similar means for allowing computer programs or other instructions to be loaded into computer system 2300. Such means may include, for example, a removable storage unit 2322 and an interface 2320. Examples of such means may include a program cartridge and cartridge interface (such as that found in video game devices), a removable memory chip (such as an EPROM, or PROM) and associated socket, and other removable storage units 2322 and interfaces 2320 which allow software and data to be transferred from the removable storage unit 2322 to computer system 2300.

Computer system 2300 may also include a communication interface 2324. Communication interface 2324 allows software and data to be transferred between computer system 2300 and external devices. Communication interface 2324 may include a modem, a network interface (such as an Ethernet card), a communication port, a PCMCIA slot and card, or the like. Software and data transferred via communication interface 2324 may be in the form of signals, which may be electronic, electromagnetic, optical, or other signals capable of being received by communication interface 2324. These signals may be provided to communication interface 2324 via a communication path 2326. Communication path 2326 carries signals and may be implemented using wire or cable, fiber optics, a phone line, a cellular phone link, an RF link or other communication channels.

In this document, the terms "computer program medium" and "computer usable medium" are used to generally refer to media such as removable storage unit 2318, removable storage unit 2322, and a hard disk installed in hard disk drive 2312. Computer program medium and computer usable medium may also refer to memories, such as main memory 2308 and secondary memory 2310, which may be memory semiconductors (e.g. DRAMs, etc.).

Computer programs (also called computer control logic) are stored in main memory 2308 and/or secondary memory 2310. Computer programs may also be received via communication interface 2324. Such computer programs, when executed, enable computer system 2300 to implement the embodiments as discussed herein. In particular, the computer programs, when executed, enable processor device 2304 to implement the processes of the embodiments discussed here. Accordingly, such computer programs represent controllers of the computer system 2300. Where the embodiments are implemented using software, the software may be stored in a computer program product and loaded into computer system 2300 using removable storage drive 2314, interface 2320, and hard disk drive 2312, or communication interface 2324.

Embodiments of the inventions also may be directed to computer program products comprising software stored on any computer useable medium. Such software, when executed in one or more data processing device, causes a data processing device(s) to operate as described herein. Embodiments of the inventions may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

FIGS. 24-28 show exemplary soles 2400, 2500, 2600, 2700, and 2800 having integrally formed midsoles and outsoles according to some embodiments. In some embodiments, the midsoles may include strips as discussed herein. In some embodiments, the outsoles may include one or more ground contacting portions and/or one or more perimeter portions as discussed herein. While soles 2400, 2500, 2600, 2700, and 2800 include different outsole and/or midsole constructions, one skilled in the art would understand that features of the different soles may be combined or substituted for each other in some embodiments. Further, one skilled in the art would understand that features of these soles may be incorporated into embodiments that do not include integrally formed midsoles and outsoles. The integrally formed midsoles and outsoles may be formed together as single pieces in an additive manufacturing process, such as a 3D-printing process including selective laser sintering, selective laser melting, selective heat sintering, stereo lithography, fused deposition modeling, or continuous liquid interface production. In other words, the outsoles and midsoles may be manufactured together and no bonding between the two, e.g. via adhesives, may be necessary.

Sole 2400 includes a midsole 2410 and an outsole 2420. Midsole 2410 includes a three-dimensional mesh 2412 having interconnected unit cells 2414 as discussed herein. In some embodiments, midsole 2410 may include one or more strips 2416 formed on three-dimensional mesh 2412. In such embodiments, strip(s) 2416 may define a portion of a perimeter side of sole 2400. In some embodiments, strip(s) 2416 do not define a portion of three-dimensional mesh 2414, rather strip(s) 2416 are an additional component of midsole 2410 formed on mesh 2412. Strip(s) 2416 may extend around all or a portion of a perimeter side of sole 2400. For example, strips(s) 2416 may extend from a lateral perimeter side of sole 2400, around a heel perimeter side of sole 2400, and onto a medial perimeter side of sole 2400.

Strip(s) 2416 may include any suitable cross-sectional shape, such as but not limited to a triangular shape, a square shape, a hexagonal shape, a circular shape, or an oval shape. In some embodiments, strip(s) 2416 may be solid bar-like or tube-like elements. In some embodiments, strip(s) 2416 may be hollow bar-like or tube-like elements. Strip(s) 2416 may be long, narrow elements having a length substantially larger than their thickness and/or width.

In some embodiments, strip(s) 2416 may extend between and connect adjacent nodes of unit cells 2414 on the perimeter of sole 2400. In some embodiments, strip(s) 2416 may facilitate alignment and/or attachment of additional components on sole 2400, for example, logos, textured/haptic elements, traction elements, and/or wear resistant elements. In some embodiments, textured/haptic elements, traction elements, and/or wear resistant elements may be polymeric elements (e.g., molded polymeric elements). In some embodiments, strip(s) 2416 may provide structural support, traction, and/or wear resistance for a perimeter side of sole 2400. In some embodiments, strip(s) 2416 may provide desired texture or haptic characteristics to portions of sole 2400. In some embodiments, strip(s) 2416 may be formed based a biometric data profile in a similar fashion as described herein for three-dimensional meshes. In other words, strip(s) 2416 may provide tailored footwear characteristics for an individual, or group of individuals. In some embodiments, strip(s) 2416 may not be formed based on a biometric data profile. In some embodiments, strip(s) 2416 may extend from outsole 2420, for example, from a perimeter side portion 2424 or a ground contacting portion 2422 of outsole 2420.

Outsole 2420 may include one or more portions 2422 defining ground contacting surface(s) of sole 2400 and one or more portions 2424 defining a perimeter side portion of sole 2400. In some embodiments, portion(s) 2422 and/or portion(s) 2424 may include traction elements (e.g., the same as or similar to protrusions 142 or traction elements 2826). Traction elements may be provided in a heel portion, a midfoot portion, and/or a forefoot portion of outsole 2420. In some embodiments, traction elements may be disposed continuously from a heel side to a forefoot side of outsole 2420. In some embodiments, traction elements may include cleats.

Figure 24:
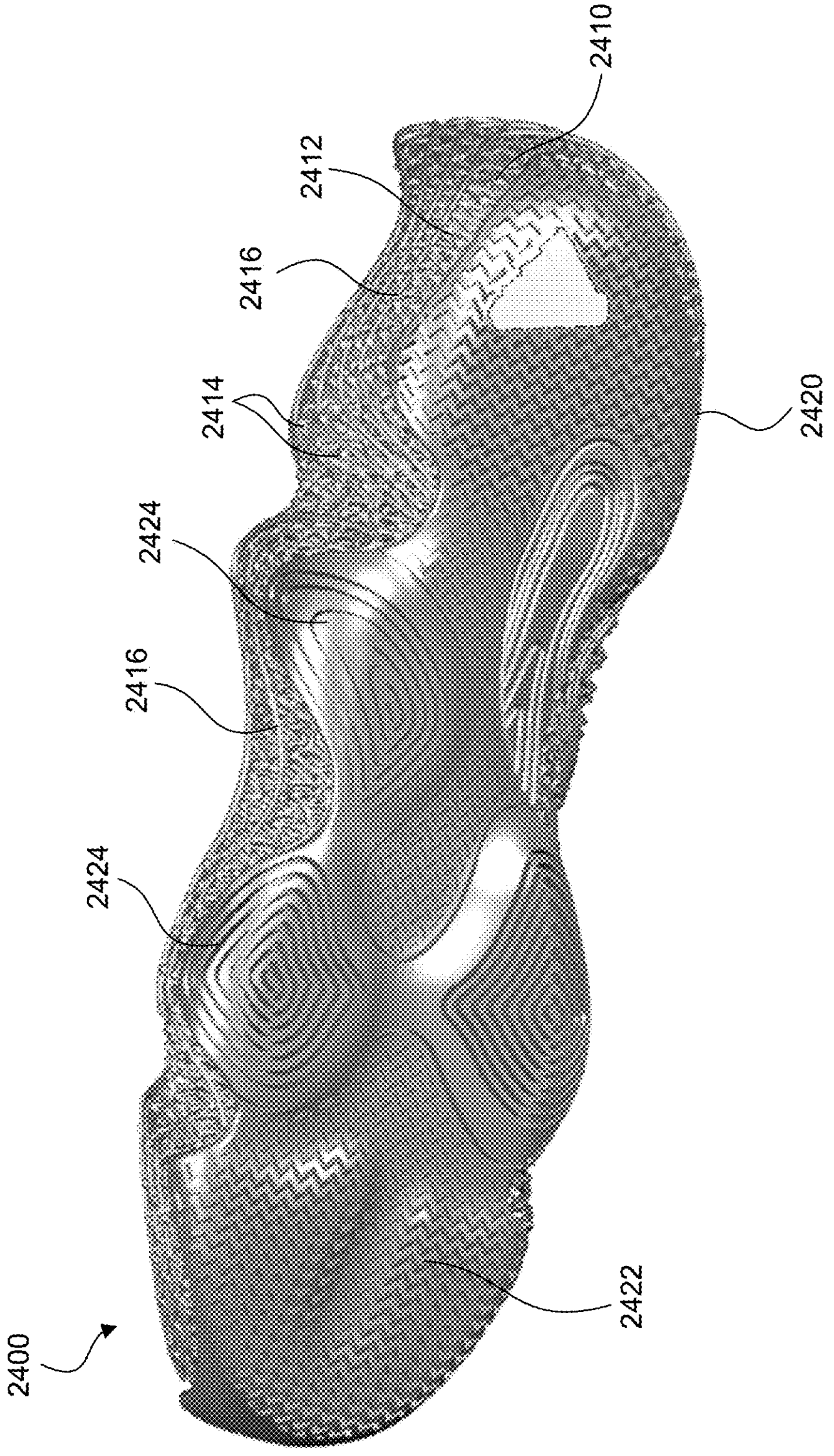
FIG. 24 is a sole according to some embodiments.
Figure 25:
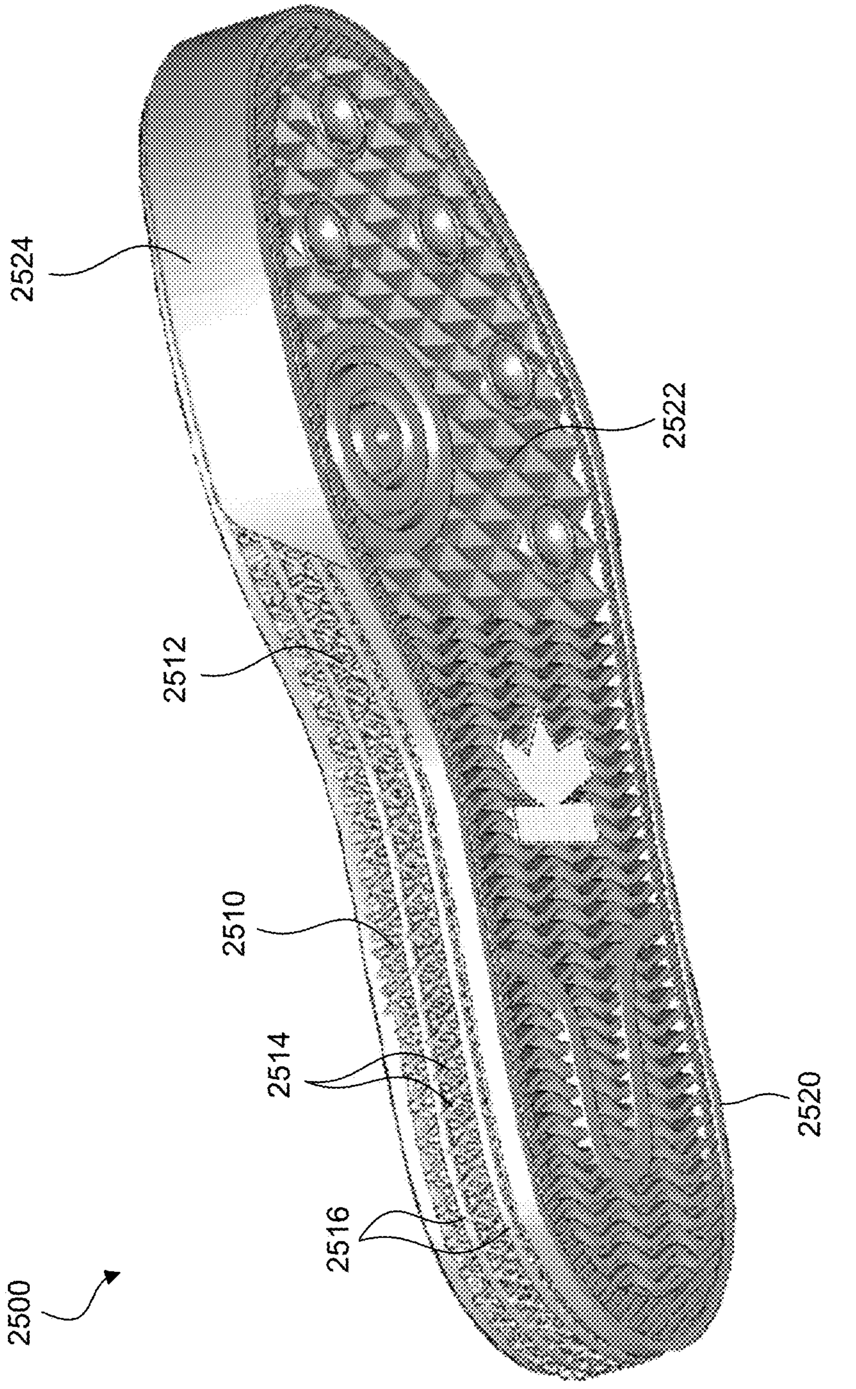
FIG. 25 is a sole according to some embodiments.

As shown in FIG. 24, portions 2424 may be formed over and cover two or more of the plurality of the interconnected unit cells 2414 of midsole 2410 at locations corresponding to portions 2424 on the perimeter side of sole 2400. In some embodiments, outsole 2420 may include a plurality of perimeter side portions 2424. In some embodiments, portion(s) 2424 may be located in a forefoot portion, a midfoot portion, and/or a heel portion of sole 2400. In some embodiments, portion(s) 2424 may be located on a heel side, a forefoot side, a medial side, and/or a lateral side of sole 2400. Perimeter side portion(s) 2424 may extend from ground contacting portion(s) 2422 and wrap around a perimeter side portion of sole 2400. Perimeter portion(s) 2424 may have any suitable shape, such as but not limited to, square shapes, rectangular shapes, rounded shapes, and curved shapes. In some embodiments, portion(s) 2424 may provide desired texture or haptic characteristics to portions of sole 2400 (e.g., a smooth texture).

Sole 2500 includes a midsole 2510 and an outsole 2520. Midsole 2510 includes a three-dimensional mesh 2512 having interconnected unit cells 2514 as discussed herein. In some embodiments, midsole 2510 may include one or more strips 2516 formed on three-dimensional mesh 2512. In such embodiments, strip(s) 2516 may define a portion of a perimeter side of sole 2500. In some embodiments, strip(s) 2516 do not define a portion of three-dimensional mesh 2514, rather strip(s) 2516 are an additional component of midsole 2510 formed on mesh 2512. Similar to strip(s) 2416, strip(s) 2516 may extend around all or a portion of a perimeter side of sole 2500. Strip(s) 2516 may have the same or similar shape and dimensions as strip(s) 2416.

In some embodiments, strip(s) 2516 may extend between and connect adjacent nodes of unit cells 2514 on the perimeter side of sole 2500. In some embodiments, strip(s) 2516 may facilitate alignment and/or attachment of additional components on sole 2500, for example, logos, textured/haptic elements, traction elements, and/or wear resistant elements. In some embodiments, textured/haptic elements, traction elements, and/or wear resistant elements may be polymeric elements (e.g., molded polymeric elements). In some embodiments, strip(s) 2516 may provide structural support, traction, and/or wear resistance for a perimeter side of sole 2500. In some embodiments, strip(s) 2516 may provide desired texture or haptic characteristics to portions of sole 2500. In some embodiments, strip(s) 2516 may be formed based a biometric data profile in a similar fashion as described herein for three-dimensional meshes. In some embodiments, strip(s) 2516 may not be formed based on a biometric data profile.

Outsole 2520 may include one or more portions 2522 defining ground contacting surface(s) of sole 2500 and one or more portions 2524 defining a perimeter side portion of sole 2500. In some embodiments, portion(s) 2522 and/or portion(s) 2524 may include traction elements (e.g., the same as or similar to protrusions 142 or traction elements 2826). Traction elements may be provided in a heel portion, a midfoot portion, and/or a forefoot portion of outsole 2520. In some embodiments, traction elements may be disposed continuously from a heel side to a forefoot side of outsole 2520. In some embodiments, traction elements may include cleats. Similar to portions 2424, portion(s) 2524 may be formed over and cover two or more of the plurality of the interconnected unit cells 2514 of midsole 2510 at locations corresponding to portion(s) 2524 on the perimeter of sole 2500. In some embodiments, portion(s) 2524 may provide desired texture or haptic characteristics to portions of sole 2500 (e.g., a smooth texture).

Sole 2600 includes a midsole 2610 and an outsole 2620. Midsole 2610 includes a three-dimensional mesh 2612 having interconnected unit cells 2614 as discussed herein. Outsole 2620 may include one or more portions 2622 defining ground contacting surface(s) of sole 2600 and one or more portions 2624 defining a perimeter side portion of sole 2600. In some embodiments, portion(s) 2622 and/or portion(s) 2624 may include traction elements (e.g., the same as or similar to protrusions 142 or traction elements 2826). Traction elements may be provided in a heel portion, a midfoot portion, and/or a forefoot portion of outsole 2620. In some embodiments, traction elements may be disposed continuously from a heel side to a forefoot side of outsole 2620. In some embodiments, traction elements may include cleats.

Figure 26:
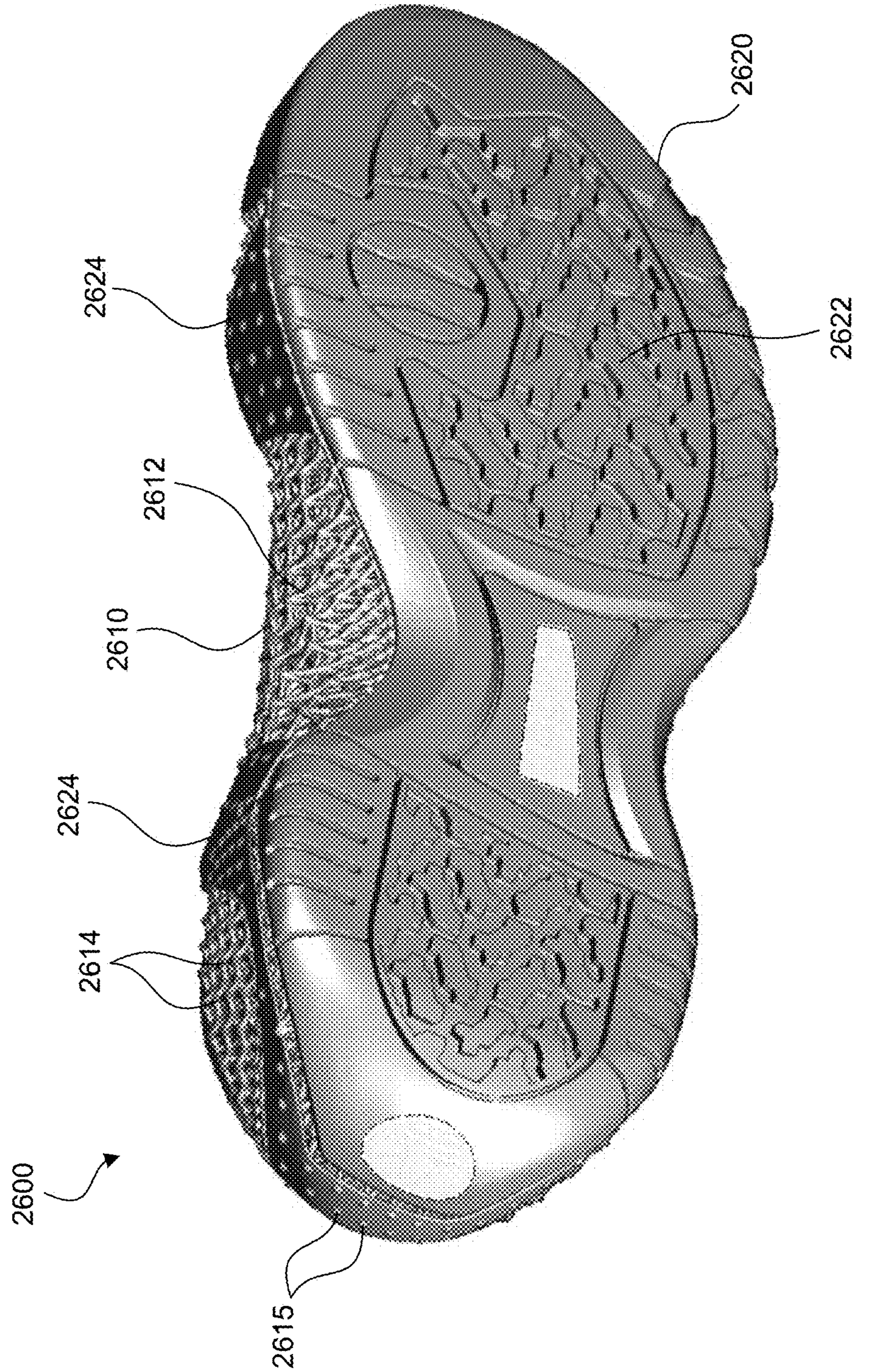
FIG. 26 is a sole according to some embodiments.
Figure 27:
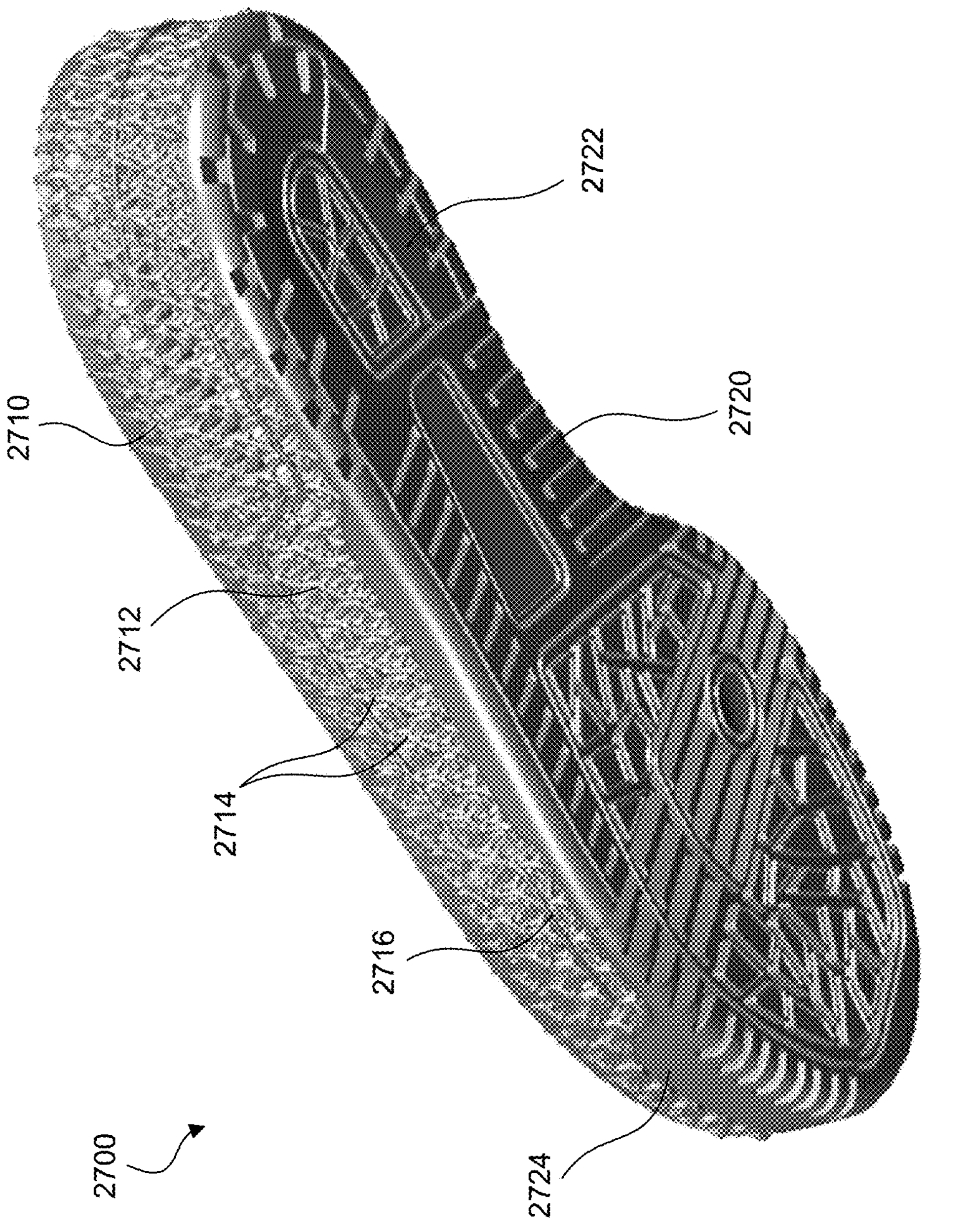
FIG. 27 is a sole according to some embodiments.
Figure 28:
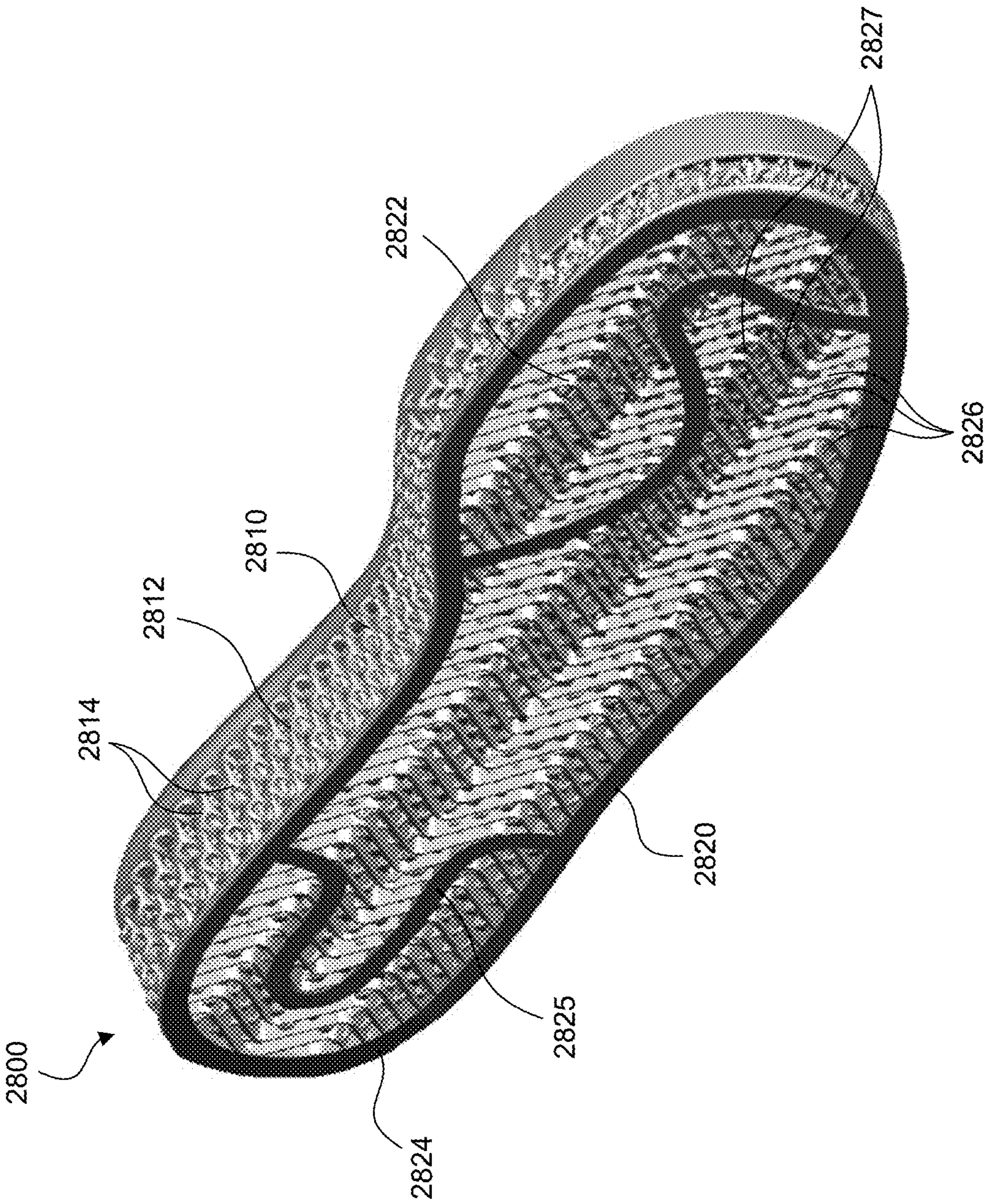
FIG. 28 is a sole according to some embodiments.

As shown in FIG. 26, portions 2624 may be formed over and cover two or more of the plurality of the interconnected unit cells 2614 of midsole 2610 at locations corresponding to portions 2624 on the perimeter of sole 2600. In some embodiments, outsole 2620 may include a plurality of perimeter side portions 2624. In some embodiments, portion(s) 2624 may be located in a forefoot portion, a midfoot portion, and/or a heel portion of sole 2600. In some embodiments, portion(s) 2624 may be located on a heel side, a forefoot side, a medial side, and/or a lateral side of sole 2600. In some embodiments, perimeter side portions 2624 may extend from ground contacting portion(s) 2622 and wrap around a perimeter side portion of sole 2600. Portions 2624 may have any suitable shape, such as but not limited to, square shapes, rectangular shapes, rounded shapes, and curved shapes.

In some embodiments, perimeter portion(s) 2624 may extend around all or a portion of a perimeter side of sole 2600. For example, portion(s) 2624 may extend from a lateral perimeter side of sole 2600, around a heel perimeter side of sole 2600, and onto a medial perimeter side of sole 2600. In some embodiments, portion(s) 2624 may facilitate alignment and/or attachment of additional components on sole 2600, for example, logos, textured/haptic elements, traction elements, and/or wear resistant elements. In some embodiments, textured/haptic elements, traction elements, and/or wear resistant elements may be polymeric elements (e.g., molded polymeric elements). In some embodiments, portion(s) 2624 may provide structural support, traction, and/or wear resistance for a perimeter side of sole 2600. In some embodiments, portion(s) 2624 may provide desired texture or haptic characteristics to portions of sole 2600 (e.g., a smooth texture). In some embodiments, nodes 2615 of interconnected unit cells 2614 covered by portion(s) 2624 may protrude from portion(s) 2624. In such embodiments, nodes 2615 may provide traction and/or wear resistance for a perimeter side of sole 2600.

Sole 2700 includes a midsole 2710 and an outsole 2720. Midsole 2710 includes a three-dimensional mesh 2712 having interconnected unit cells 2714 as discussed herein. In some embodiments, midsole 2710 may include one or more strips 2716 formed on three-dimensional mesh 2712. In such embodiments, strip(s) 2716 may be the same as or similar to strip(s) 2416. Outsole 2720 may include one or more portions 2722 defining ground contacting surface(s) of sole 2700 and one or more portions 2724 defining a perimeter side portion of sole 2700. Ground contacting portion(s) 2722 and perimeter portion(s) 2724 may be the same as or similar to ground contacting portion(s) 2422 and perimeter portion(s) 2424, respectively.

Sole 2800 includes a midsole 2810 and an outsole 2820. Midsole 2810 includes a three-dimensional mesh 2812 having interconnected unit cells 2814 as discussed herein. Outsole 2820 includes a portion 2822 defining ground contacting surface(s) of sole 2800. In some embodiments, ground contacting portion 2822 may include traction elements 2826. In some embodiments, traction elements 2826 may be disposed within an outsole frame 2824. Traction elements may be provided in a heel portion, a midfoot portion, and/or a forefoot portion of outsole 2820. In some embodiments, traction elements may be disposed continuously from a heel side to a forefoot side of outsole 2820. In some embodiments, traction elements may include cleats.

In some embodiments, traction elements 2826 may be spaced-apart protrusions or ribs. In some embodiments, traction elements 2826 may be spaced apart such that they define openings 2827 in ground contacting portion 2822. In such embodiments, openings 2827 may be through holes and three-dimensional mesh 2812 may be visible through openings 2827. In some embodiments, ground contacting portion 2822 may include one or more crossbars 2825 extending from outsole frame 2824. Crossbars 2825 may extend between opposite sides of frame 2824 (e.g., between a medial side and a lateral side of frame 2824 or between a heel side and a forefoot side of frame 2824). Crossbars 2825 may provide traction and/or structural support for outsole 2820. In some embodiments, crossbars 2825 may be curved or rounded. In some embodiments, crossbars 2825 may be straight.

Some embodiments may include a midsole for an article of footwear, the midsole including a three-dimensional mesh including a plurality of interconnected unit cells, each interconnected unit cell including a plurality of struts defining a three-dimensional shape and a plurality of nodes at which one or more struts are connected, where each node includes a valence number defined by the number of struts that are connected at that node and the valence number of the nodes varies in a longitudinal direction along the length of the midsole between a forefoot end of the midsole and a heel end of the midsole.

In any of the various embodiments discussed herein, the valence number of nodes in a midsole may vary in a transverse direction along the width of the midsole between a lateral side of the midsole and a medial side of the midsole.

In any of the various embodiments discussed herein, the average value for the valence numbers of nodes in a forefoot portion of a midsole may be greater than the average value for the valence numbers of nodes in a heel portion of the midsole.

In any of the various embodiments discussed herein, the size of the unit cells in a midsole may vary in the midsole.

In any of the various embodiments discussed herein, the average size of the unit cells positioned in a forefoot portion of a midsole may be less than the average size of the unit cells positioned in a heel portion of the midsole.

In any of the various embodiments discussed herein, the size of the unit cells in a midsole may vary in the longitudinal direction along the length of the midsole between a forefoot end of the midsole and a heel end of the midsole.

In any of the various embodiments discussed herein, the average size of the unit cells in a midsole may increase in the longitudinal direction along the length of the midsole from the forefoot end of the midsole to the heel end of the midsole.

In any of the various embodiments discussed herein, the size of the unit cells in a midsole may vary in a vertical direction between a top side of the midsole and a bottom side of the midsole.

In any of the various embodiments discussed herein, the average size of the unit cells in a midsole may increase in a vertical direction from the bottom side of the midsole to the top side of the midsole.

In any of the various embodiments discussed herein, each unit cell in a midsole may have the same base geometry.

In any of the various embodiments discussed herein, the unit cells in a midsole may have a valence number in the range of 1 to 12.

In any of the various embodiments discussed herein, a midsole may include a plurality of unit cells having a first base geometry and a plurality unit cells having a second base geometry different from the first base geometry. In some embodiments, a plurality of unit cells having the first base geometry may be located in a forefoot portion of the midsole and a plurality of unit cells having the second base geometry may be located in a heel portion of the midsole. In some embodiments, a midfoot portion of the midsole may include a plurality of unit cells having the first base geometry and a plurality of unit cells having the second base geometry.

In any of the various embodiment discussed herein, 90% or more of all the unit cells in a midsole may be a complete unit cell.

In any of the various embodiments discussed herein, the variation in the valence number in the longitudinal direction along the length of a midsole may be based on a biometric data profile collected for an individual. In some embodiments, the biometric data profile may include information about the individual's gait collected from motion sensors coupled to the individual's foot during a test procedure.

In any of the various embodiments discussed herein, variation in the size of the unit cells in a midsole may be based on a biometric data profile collected for an individual.

In any of the various embodiments discussed herein, the location of a plurality of unit cells having a first base geometry and the location of a plurality of unit cells having a second base geometry may be based on a biometric data profile collected for an individual.

Some embodiments may include a midsole for an article of footwear, the midsole including a three-dimensional mesh including a plurality of interconnected unit cells organized in a warped cubic lattice structure that defines a volume of the midsole, each interconnected unit cell including a plurality of struts defining a three-dimensional shape, and the warped cubic lattice structure including a plurality of warped cubic lattice cells having different volumes and cubic geometries, where the warped cubic lattice structure defines a plurality of nodes at which one or more struts are connected and the warped cubic lattice structure is warped in a longitudinal direction along the length of the midsole, in a transverse direction along the width of the midsole, and in a vertical direction along the height of the midsole.

In any of the various embodiments discussed herein, the size of the unit cells in a midsole may vary based on the volume of the cubic cell in which a unit cell is positioned.

In any of the various embodiments discussed herein, the geometry of the unit cells in a midsole may vary based on the geometry of the cubic cell in which a unit cell is positioned.

In any of the various embodiments discussed herein, two or more interconnected unit cells may be positioned in a single warped cubic lattice cell. In some embodiments, the two or more interconnected unit cells positioned in a single warped cubic lattice cell may be unit cells having different base geometries.

In any of the various embodiments discussed herein, the volume and cubic geometry of the warped cubic lattice cells in a warped cubic lattice structure may be based on a biometric data profile collected for an individual.

Some embodiments may include a sole for an article of footwear, the sole including a 3-D printed outsole having a portion defining a ground contacting surface of the sole and a portion defining a perimeter side portion of the sole, and a 3-D printed midsole integrally formed with the outsole and having a three-dimensional mesh including a plurality of interconnected unit cells, each interconnected unit cell including a plurality of struts defining a three-dimensional shape, and a plurality of nodes at which one or more struts are connected, where each node includes a valence number defined by the number of struts that are connected at that node, the valence number of the nodes varies in a longitudinal direction along the length of the midsole between a forefoot end of the midsole and a heel end of the midsole, and the perimeter side portion of the sole defined by the outsole is formed over and covers two or more of the plurality of the interconnected unit cells at the perimeter side portion.

Some embodiments may include a sole for an article of footwear, the sole including a 3-D printed outsole having a portion defining a ground contacting surface of the sole and a portion defining a perimeter side portion of the sole, and a 3-D printed midsole integrally formed with the outsole and having a three-dimensional mesh including a plurality of interconnected unit cells organized in a warped cubic lattice structure that defines a volume of the midsole, each interconnected unit cell including a plurality of struts defining a three-dimensional shape, and the warped cubic lattice structure including a plurality of warped cubic lattice cells having different volumes and cubic geometries, where the warped cubic lattice structure defines a plurality of nodes at which one or more struts are connected, the warped cubic lattice structure is warped in a longitudinal direction along the length of the midsole, in a transverse direction along the width of the midsole, and in a vertical direction along the height of the midsole, and where the perimeter side portion of the sole defined by the outsole is formed over and covers two or more of the plurality of the interconnected unit cells at the perimeter side portion.

Some embodiments may include a method of making a midsole for an article of footwear, the method including generating a warped cubic lattice structure based on a biometric data profile collected for an individual, the warped cubic lattice structure: defining a volume of the midsole, including a plurality of cubic lattice cells having different volumes and cubic geometries, and defining a plurality of nodes; populating each cubic lattice cell with one or more partial lattice unit cells based on the biometric data profile, the partial lattice unit cells forming a cell lattice including lattice unit cells connected to each other at one or more of the nodes; and forming a three-dimensional mesh based on the biometric data profile, the three-dimensional mesh including a plurality of interconnected unit cells, each unit cell including a plurality of struts defining a three-dimensional shape corresponding to the shape of a respective lattice unit cell, thereby forming the midsole.

In any of the various embodiments discussed herein, a biometric data profile may include information about the individual's gait collected from motion sensors coupled to the individual's foot during a testing procedure. In some embodiments, the motion sensors may include at least one of: acceleration sensors and magnetic field sensors. In some embodiments, the information about the individual's gait may include information about how the individual's foot rolls when it contacts the ground and information about how the individual's foot strikes the ground.

In any of the various embodiments discussed herein, forming a three-dimensional mesh may include an additive manufacturing process.

In any of the various embodiments discussed herein, forming a three-dimensional mesh may include a continuous liquid interface production process.

Some embodiments include a method of making a sole for an article of footwear, the method including generating a warped cubic lattice structure based on a biometric data profile collected for an individual, the warped cubic lattice structure: defining a volume of a midsole for the sole, including a plurality of cubic lattice cells having different volumes and cubic geometries, and defining a plurality of nodes; populating each cubic lattice cell with one or more partial lattice unit cells based on the biometric data profile, the partial lattice unit cells forming a cell lattice including lattice unit cells connected to each other at one or more of the nodes; printing a three-dimensional mesh based on the biometric data profile, the three-dimensional mesh including a plurality of interconnected unit cells, each unit cell including a plurality of struts defining a three-dimensional shape corresponding to the shape of a respective lattice unit cell, thereby forming the midsole; and printing an outsole with the midsole, the outsole including a portion defining a ground contacting surface of the sole and a portion defining a perimeter side portion of the sole, where the perimeter side portion of the sole defined by the outsole is formed over and covers two or more of the plurality of the interconnected unit cells at the perimeter side portion.

In any of the various embodiments discussed herein, printing the three-dimensional mesh and the outsole may include a continuous liquid interface production process.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention(s) and the appended claims in any way.

The present invention(s) have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention(s) that others can, by applying knowledge within the skill of the art, readily modify and/or adapt for various applications such specific embodiments, without undue experimentation, without departing from the general concept of the present invention(s). Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention(s) should not be limited by any of the above-described exemplary embodiments, but should be defined only in accordance with the following claims and their equivalents.

What is claimed is:

1. A method of making a sole for an article of footwear, the method comprising:

generating a lattice structure, the lattice structure: defining a volume of at least a portion of a midsole for the sole, comprising a plurality of lattice cells, and defining a plurality of nodes;

populating each one of the plurality of lattice cells with a lattice unit cell, the lattice unit cells defining a cell lattice comprising the lattice unit cells connected to each other at one or more of the nodes, and the lattice unit cells comprising a first plurality of lattice unit cells comprising a first base geometry and a second plurality of lattice unit cells comprising a second base geometry different than the first base geometry, wherein populating each one of the plurality of lattice cells comprises populating each one of the plurality of lattice cells with two or more individual partial lattice unit cells, the two or more individual partial lattice unit cells defining a respective lattice unit cell in the cell lattice; and forming a three-dimensional mesh for the midsole, the three-dimensional mesh comprising a plurality of interconnected unit cells, wherein a first plurality of the interconnected unit cells each comprise a plurality of struts defining a three-dimensional shape corresponding to the first base geometry, and wherein a second plurality of the interconnected unit cells each comprise a plurality of struts defining a three-dimensional shape corresponding to the second base geometry, wherein the first plurality of lattice unit cells comprising the first base geometry is populated at a first unit cell density and the second plurality of lattice unit cells comprising the second base geometry is populated at a second unit cell density different than the first unit cell density.

2. The method of claim 1, wherein the three-dimensional mesh comprises a first region comprising the first plurality of interconnected unit cells and a second region comprising the second plurality of interconnected unit cells.

3. The method of claim 2, further comprising a transition region between the first region and the second region, the transition region comprising unit cells comprising the first base geometry interspersed with unit cells comprising the second base geometry.

4. The method of claim 2, wherein a forefoot portion of the midsole comprises the first region and a heel portion of the midsole comprises the second region.

5. The method of claim 1, wherein the three-dimensional mesh comprises a third region comprising a third plurality of interconnected unit cells comprising a third base geometry different than the first base geometry and the second base geometry.

6. The method of claim 1, wherein the lattice structure comprises a cubic lattice structure.

7. The method of claim 1, wherein the lattice structure comprises a plurality of warped lattice cells and a plurality of unwarped lattice cells.

8. The method of claim 7, wherein the first plurality of lattice unit cells comprises: lattice unit cells comprising the first base geometry populated in unwarped lattice cells of the lattice structure, and lattice unit cells comprising a warped version of the first base geometry populated in warped lattice cells of the lattice structure, and wherein the first plurality of the interconnected unit cells comprises unit cells comprising the first base geometry, and unit cells comprising a warped version of the first base geometry.

9. The method of claim 8, wherein the second plurality of lattice unit cells comprises: lattice unit cells comprising the second base geometry populated in unwarped lattice cells of the lattice structure, and lattice unit cells comprising a warped version of the second base geometry populated in warped lattice cells of the lattice structure, and wherein the second plurality of the interconnected unit cells comprises unit cells comprising the second base geometry, and unit cells comprising a warped version of the second base geometry.

10. The method of claim 1, wherein the plurality of lattice cells of the lattice structure comprises lattice cells with different volumes.

11. The method of claim 10, wherein an average size of the lattice cells increases in a longitudinal direction along a length of the midsole.

12. The method of claim 11, wherein an average size of the interconnected unit cells increases in the longitudinal direction.

13. The method of claim 1, wherein the lattice structure is based on a biometric data profile collected for an individual, and wherein the lattice cells are populated with the lattice unit cells based on the biometric data profile.

14. The method of claim 13, wherein the biometric data profile comprises information about the individual's gait collected from motion sensors coupled to the individual's foot during a testing procedure.

15. The method of claim 13, wherein the biometric data profile comprises a standard biometric data profile for a group of individuals comprising the individual.

16. The method of claim 13, wherein the biometric data profile comprises information about how the individual's foot rolls when it contacts the ground and information about how the individual's foot strikes the ground.

17. The method of claim 1, wherein the lattice cells are populated with lattice unit cells and the three-dimensional mesh is formed based on a lattice map comprising a plurality of lattice zones, and wherein each of the plurality of lattice zones designates:

the first base geometry or the second base geometry, and at least one of the following features for the three-dimensional mesh: (1) strut stiffness for interconnected unit cells in the zone, (ii) a number of interconnected unit cells per unit volume in the zone, (iii) a valence number of nodes in the zone, or (iv) a material used to form interconnected unit cells in the zone.

18. The method of claim 1, wherein forming the three-dimensional mesh comprises an additive manufacturing process.

* * * * *